US010864101B2

(12) United States Patent
Ito et al.

(10) Patent No.: US 10,864,101 B2
(45) Date of Patent: Dec. 15, 2020

(54) GARMENT PROVIDED WITH JOINT SUPPORTER SECTION, AND KNEE SUPPORTER

(71) Applicant: MITSUI CHEMICALS, INC., Tokyo (JP)

(72) Inventors: Tomoaki Ito, Ichihara (JP); Kenji Iida, Ichihara (JP); Motoyasu Yasui, Chiba (JP); Shiori Ito, Tsuchiura (JP); Kazuoki Nakai, Ichihara (JP); Fumiaki Saikawa, Ashikita-gun (JP)

(73) Assignee: MITSUI CHEMICALS, INC., Tokyo (JP)

( * ) Notice: Subject to any disclaimer, the term of this patent is extended or adjusted under 35 U.S.C. 154(b) by 491 days.

(21) Appl. No.: 15/567,344

(22) PCT Filed: Apr. 22, 2016

(86) PCT No.: PCT/JP2016/062827
§ 371 (c)(1),
(2) Date: Oct. 17, 2017

(87) PCT Pub. No.: WO2016/171272
PCT Pub. Date: Oct. 27, 2016

(65) Prior Publication Data
US 2018/0133045 A1 May 17, 2018

(30) Foreign Application Priority Data

Apr. 22, 2015 (JP) .................................. 2015-087593
Feb. 4, 2016 (JP) .................................. 2016-020145

(51) Int. Cl.
*A61F 5/01* (2006.01)
*A41D 13/06* (2006.01)
(Continued)

(52) U.S. Cl.
CPC ............ *A61F 5/0123* (2013.01); *A41D 13/06* (2013.01); *A61F 5/01* (2013.01); *A61F 5/0109* (2013.01); *A61F 5/02* (2013.01); *A61F 13/06* (2013.01)

(58) Field of Classification Search
CPC ........ A61F 5/0123; A61F 5/0109; A61F 5/01; A61F 13/06; A61F 5/02; A61F 5/0106;
(Continued)

(56) References Cited

U.S. PATENT DOCUMENTS 4,908,037 A 3/1990 Ross
2012/0078151 A1* 3/2012 Cropper .................... A61F 5/34
602/26
(Continued)

FOREIGN PATENT DOCUMENTS

EP 2 526 791 A1 11/2012
JP 3018988 U 12/1995
(Continued)

OTHER PUBLICATIONS

Oct. 30, 2018 extended European Search Report issued in European Patent Application No. 16783293.0.
(Continued)

*Primary Examiner* — Tarla R Patel
(74) *Attorney, Agent, or Firm* — Oliff PLC

(57) ABSTRACT

A garment, containing a tubular joint supporter section, the section including: a central region in an axial direction of the tubular joint supporter section, which includes a wear pressure applying region for applying wear pressure to a joint site of a body, a one-end side region positioned at one end, and an other-end side region positioned at another end side, in which the wear pressure of the wear pressure applying region is higher than an average wear pressure of the one-end and other-end side regions, and regions other than
(Continued)

the wear pressure applying region in the section include a concave-convex structure region formed from a concave-convex structure; and a knee supporter, in which an average wear pressure A of the knee support section is higher than an average wear pressure B of the thigh side support section and the shin side support section.

6 Claims, 14 Drawing Sheets

(51) Int. Cl.
*A61F 5/02* (2006.01)
*A61F 13/06* (2006.01)

(58) Field of Classification Search
CPC .... A41D 13/06; A61B 17/56; A61B 71/1225; B43L 15/00
USPC .......................................................... 602/26
See application file for complete search history.

(56) References Cited

U.S. PATENT DOCUMENTS

2012/0277649 A1* 11/2012 Matsuo ................ A41D 13/065
602/63
2012/0289875 A1* 11/2012 Matsuo ................. A61F 13/101
602/20
2014/0316312 A1 10/2014 Atmanspacher

FOREIGN PATENT DOCUMENTS

| JP | H11-200119 A | 7/1999 |
| JP | 2000-116697 A | 4/2000 |
| JP | 2007-009362 A | 1/2007 |
| JP | 2007-054126 A | 3/2007 |
| JP | 2008-054918 A | 3/2008 |
| JP | 2010-013765 A | 1/2010 |
| JP | 2011-130784 A | 7/2011 |
| JP | 2013-104138 A | 5/2013 |
| WO | 00/51537 A1 | 9/2000 |
| WO | 2011/090194 A1 | 7/2011 |
| WO | 2011/090195 A1 | 7/2011 |

OTHER PUBLICATIONS

Jul. 26, 2016 International Search Report issued in International Patent Application No. PCT/JP2016/062827.
Mar. 3, 2020 Office Action issued in Japanese Patent Application No. 2018-165097.

* cited by examiner

GARMENT PROVIDED WITH JOINT SUPPORTER SECTION, AND KNEE SUPPORTER

TECHNICAL FIELD

The present invention relates to a garment provided with a joint supporter section, and a knee supporter.

BACKGROUND ART

A variety of knee supporters are currently known.

For example, there is known a knee supporter which can be worn by an easy wearing operation, is capable of selectively compressing, fastening, warming or the like an appropriate site in response to pain, and can be produced by a simple production process, the knee supporter being provided by being knitted separately into a plurality of regions having different stretchability at a site that covers the kneecap and its periphery, and at least a portion of the site is produced into a low-stretchability region having lower stretchability compared to the other regions of the site(see, for example, the following patent document 1).

Also known is a knee supporter capable of maintaining a fitted state without being shifted even when stretching and bending of the knee are repeated, the knee supporter having main constituent parts formed from a stretchable material, characterized in that the supporter main body is composed of a supporter front surface upper part member, a supporter front surface lower part member, and a supporter back surface part member, the supporter front surface upper part member including a kneecap area, and when the elongation ratio in the longitudinal direction of the supporter front surface upper part member is designated as A1, the elongation ratio in the transverse direction of the same member is designated as B1, the elongation ratio in the longitudinal direction of the supporter back surface part member is designated as A2, and the elongation ratio in the transverse direction of the same member is designated as B2, the following relationships are satisfied: A1>B1, and A2<B2 (see, for example, the following patent document 2).

Also known is a compression supporter that compresses the patellar ligament, holds the kneecap, and favorably fixes the knee joint, the compression supporter includes a main body formed from a stretchable material and having a shape wearable at the knee, the main body being provided with a low stretchable region having lower stretchability than the main body so that the supporter supports the knee joint and the muscles and tendons through the difference in stretchability between the low stretchable region and the main body. The supporter also has, as the low stretchable region, a front face suspending region provided at the front face of the main body into an almost U-shape surrounding the lower part of the kneecap to compress the patellar ligament, and in the low-stretchable region, a low-stretchability material formed from a resin is fixed to the main body (see, for example, the following patent document 3).

Also known is a knee joint supporter that conforms to the movement of the skin near the knee joint, does not shift easily, and provides favorable wearability, in which the site within 10 cm from the center of the knee joint of the main body is formed into a sleeve form, the front surface part of the main body is formed from a highly stretchable material having a low modulus in the longitudinal direction, notches are provided at least in the front surface upper part of the site extending over 10 cm or more from the center of the knee joint of the main body, and members capable of adjusting the compressing force in the main direction of the main body are provided astride these notches (see, for example, the following patent document 4).

Also known is a knee joint supporter as a knee supporter which has appropriate wear-pressing properties, does not hurt the knee by over-fastening, and provides favorable bending and stretching performance at the knee, the knee joint supporter having a fastening section for preventing vertical slip-down; a knee joint cap section; an X-shaped section surrounding the cap section in a crossing manner; and a knitted structure section occupying the remaining portions. The knee joint cap section is formed from a knitted structure having the weakest wear-pressure, the X-shaped section surrounding the cap section in a crossing manner is formed from a knitted structure having compressibility, and the knitted structure section occupying the remaining portions is formed from a buffering knitted structure for facilitating bending and stretching of the knee joint (see, for example, the following patent document 5).

Patent Document 1: Japanese Patent Application Laid-Open (JP-A) No. 2011-130784
Patent Document 2: JP-A No. 2007-9362
Patent Document 3: JP-A No. 2010-13765
Patent Document 4: JP-A No. 2000-116697
Patent Document 5: JP-A No. 2007-54126

SUMMARY OF INVENTION

Technical Problem

However, in regard to knee supporters, it is preferable to further enhance a feeling of support and fitting comfort when a knee supporter is worn on a part including the knee of a leg.

The inventors of the present invention conducted an investigation, and thereby it was found that when a knee supporter includes a tubular-shaped supporter body including a knee support section that supports the knee; a thigh side support section that supports the thigh side with respect to the knee of a leg; a shin side support section that supports the shin side with respect to the knee of a leg, and when the average wear pressure A of the knee support section and the average wear pressure B of the thigh side support section and the shin side support section satisfy the relationship: average wear pressure A>average wear pressure B, a feeling of support and fitting comfort in particular are enhanced.

Furthermore, the inventors of the present invention conducted an investigation, and thereby when the relationship: average wear pressure A>average wear pressure B, is satisfied, a feeling of support and fitting comfort are enhanced; however, it was found that there are occasions in which the conformity of the knee supporter to the bending and stretching movement of the knee joint (hereinafter, also referred to as "movement conformity") of the knee supporter to the bending and stretching movement of the knee joint is impaired.

An object of first and second embodiments of the invention is to provide a knee supporter that provides an excellent feeling of support and excellent fitting comfort when worn on a part of the leg including the knee, and has excellent conformity to the bending and stretching movement of the knee joint (movement conformity).

An object of a third embodiment of the invention is to provide a knee supporter that provides an excellent feeling of support and excellent fitting comfort when worn on a part of the leg including the knee, and provides excellent ease of bending and stretching by the knee joint.

An object of a fourth embodiment of the invention is to provide a garment including a joint supporter section that provides an excellent feeling of support and excellent fitting comfort when worn on a joint, and alleviates stress on the skin.

Solution to Problem

Specific means for solving the above-described objects are as follows.

A first embodiment is a knee supporter according to the following item <25>.

A second embodiment is a knee supporter according to the following item <29>.

A third embodiment is a knee supporter according to the following item <33>.

A fourth embodiment is a garment including a joint supporter section according to the following item <1>.

At least two of the scope of the first embodiment, the scope of the second embodiment, the scope of the third embodiment, or the scope of the fourth embodiment may have overlapping parts. The respective features of the first to fourth embodiments can be combined as appropriate.

<1> A garment, containing a tubular joint supporter section, the tubular joint supporter section including:

a central region in an axial direction of the tubular joint supporter section, the central region including a wear pressure applying region for applying wear pressure to a joint site of a body;

a one-end side region positioned at one end side in the axial direction with respect to the central region; and an other-end side region positioned at another end side in the axial direction with respect to the central region, wherein:

the wear pressure of the wear pressure applying region is higher than an average wear pressure of the one-end side region and the other-end side region, and regions other than the wear pressure applying region in the tubular joint supporter section include a concave-convex structure region formed from a concave-convex structure.

<2> The garment according to <1>, wherein the concave-convex structure region formed from the concave-convex structure is a concave-convex knitted fabric region formed from a concave-convex knitted fabric.

<3> The garment according to <2>, wherein, elongation ratios of the wear pressure applying region and the concave-convex knitted fabric region in the axial direction measured by a tensile test under conditions of a grip width of 15 mm, a distance between grippers of 15 mm, and a tensile load of 20 N, satisfy the relationship: elongation ratio of concave-convex knitted fabric region>elongation ratio of wear pressure applying region.

<4> The garment according to <2> or <3>, wherein the concave-convex knitted fabric includes a float knitted structure.

<5> The garment according to any one of <2> to <4>, wherein, when the concave-convex knitted fabric region is stretched at an elongation ratio of 200% in one of an axial direction or a circumferential direction of the tubular supporter section, the elastic modulus in the one of the axial direction or the circumferential direction is less than 0.1 N/mm$^2$.

<6> The garment according to any one of <2> to <5>, wherein:

when the concave-convex knitted fabric region is stretched at an elongation ratio of 200% in one of an axial direction or a circumferential direction of the tubular supporter section, the elastic modulus in the one of the axial direction or the circumferential direction is less than 0.1 N/mm$^2$, and when the concave-convex knitted fabric region is stretched at an elongation ratio of 200% in the other of the axial direction or the circumferential direction of the tubular supporter section, the elastic modulus in the other of the axial direction or the circumferential direction is from 0.1 N/mm$^2$ to 0.5 N/mm$^2$.

<7> The garment according to any one of <2> to <6>, wherein, in the concave-convex knitted fabric region, elongation ratios in the axial direction of the tubular supporter section and in the circumferential direction of the tubular supporter section, both of which are measured by a tensile test under conditions of a grip width of 15 mm, a distance between grippers of 15 mm, and a tensile load of 20 N, satisfy the relationship: elongation ratio in the axial direction>elongation ratio in the circumferential direction.

<8> The garment according to any one of <2> to <7>, wherein at least one of the one-end side region or the other-end side region includes the concave-convex knitted fabric region.

<9> The garment according to <8>, wherein:

at least one of the one-end side region or the other-end side region further includes a region having a higher elastic modulus in the axial direction than the concave-convex knitted fabric region, and the concave-convex knitted fabric region, and the region having a higher elastic modulus in the axial direction than the concave-convex knitted fabric region, are disposed in the circumferential direction of the tubular supporter section.

<10> The garment according to any one of <2> to <9>, wherein, in the tubular supporter section, in a case in which a semicircular side centering on a center XX of the wear pressure applying region is disposed at a front face side, and the other semicircular side is disposed at a back face side, at least one of a back face side of the one-end side region or a back face side of the other-end side region includes the concave-convex knitted fabric region.

<11> The garment according to <10>, wherein:

in a case in which the back face side of the one-end side region includes the concave-convex knitted fabric region, elongation ratios in the axial direction measured by a tensile test under conditions of a grip width of 15 mm, a distance between grippers of 15 mm, and a tensile load of 20 N, satisfy the relationship: elongation ratio of concave-convex knitted fabric region at the back face side of the one-end side region>elongation ratio of front face side of the one-end side region, and in a case in which the back face side of the other-end side region includes the concave-convex knitted fabric region, elongation ratios in the axial direction measured by a tensile test under the conditions described above satisfy the relationship: elongation ratio of concave-convex knitted fabric region on the back face side of the other-end side region>elongation ratio of front face side of the other-end side region.

<12> The garment according to any one of <1> to <11>, wherein the central region is worn on a knee joint, an elbow joint, a finger joint, or a toe joint.

<13> The garment according to any one of <1> to <12>, wherein the central region is worn on a knee joint.

<14> The garment according to <13>, wherein an average wear pressure XA of the central region and an average wear pressure XB of the one-end side region and the other-end side region satisfy the relationship: average wear pressure XA>average wear pressure XB.

<15> The garment according to <14>, wherein the average wear pressure XA and the average wear pressure XB satisfy the relationship: average wear pressure XA−average wear pressure XB≥0.8 kPa.

<16> The garment according to any one of <2> to <15>, wherein:
the concave-convex structure region formed from a concave-convex structure is a concave-convex knitted fabric region formed from a concave-convex knitted fabric, and
in the concave-convex knitted fabric region, an elongation ratio in the axial direction measured by a tensile test under conditions of a grip width of 15 mm, a distance between grippers of 15 mm, and a tensile load of 20 N, is 150% or higher.

<17> The garment according to any one of <1> to <16>, wherein, in the tubular joint supporter section, in a case in which the semicircular side centering on the center XX of the wear pressure applying region is disposed at a front face side, and the other semicircular side is disposed at a back face side, when the central region is stretched with a force of 5 kg in a direction in which a distance will increase between the center XX of the wear pressure applying region and a center XY at a back face side of the central region, an elongation percentage of the central region is from 180% to 280%.

<18> The garment according to any one of <1> to <17>, wherein, in the tubular joint supporter section, in a case in which the semicircular side centering on the center XX of the wear pressure applying region is disposed at a front face side, and the other semicircular side is disposed at a back face side, when an elongation ratio in the circumferential direction is measured by a tensile test under conditions of a grip width of 15 mm, a distance between grippers of 15 mm, and a tensile load of 20 N, at each of three points in total, the three points being the center XX of the wear pressure applying region, the center XY at the back face side of the central region, and an intermediate position between the center XX and the center XY, the three measured values are all included in a range of from 100% to 250%, and a difference between a maximum value and a minimum value of the three measured values is from 0% to 80%.

<19> The garment according to any one of <13> to <15>, wherein an average wear pressure XA of the central region is 2.6 kPa or greater.

<20> The garment according to any one of <1> to <19>, wherein, in the tubular joint supporter section, in a case in which the semicircular side centering on the center XX of the wear pressure applying region is disposed at a front face side, and the other semicircular side is disposed at a back face side, when an elongation ratio in the circumferential direction is measured by a tensile test under conditions of a grip width of 15 mm, a distance between grippers of 15 mm, and a tensile load of 20 N, for each of: a measurement area XX1 centering on the center XX of the wear pressure applying region; a measurement area XT1 centering on a position XT, which is at the center in the axial direction of the one-end side region on an extension line extending in the axial direction from the center XY at the back face side of the central region; and a measurement area XS1 centering on a position XS, which is at the center in the axial direction of the other-end side region on an extension line extending in the axial direction from the center XY at the back face side of the central region, an elongation ratio in the circumferential direction of the measurement area XX1 is lower than an elongation ratio in the circumferential direction of the measurement area XT1 and is lower than an elongation ratio in the circumferential direction of the measurement area XS1.

<21> The garment according to any one of <1> to <20>, wherein, in the tubular joint supporter section, in a case in which the semicircular side centering on the center XX of the wear pressure applying region is disposed at a front face side, and the other semicircular side is disposed at a back face side, when an elongation ratio in the axial direction is measured by a tensile test under conditions of a grip width of 15 mm, a distance between grippers of 15 mm, and a tensile load of 20 N, for each of: a measurement area XX1 centering on the center XX of the wear pressure applying region; a measurement area XT1 centering on the position XT, which is at the center in the axial direction in the one-end side region on an extension line extending in the axial direction from the center XY at the back face side of the central region; and a measurement area XS1 centering on the position XS, which is at the center in the axial direction of the other-end side region on an extension line extending in the axial direction from the center XY at the back face side of the central region, an elongation ratio in the axial direction of the measurement area XX1 is lower than an elongation ratio in the axial direction of the measurement area XT1 and is lower than an elongation ratio in the axial direction of the measurement area XS1.

<22> The garment according to any one of <1> to <21>, wherein a total structure of the tubular joint supporter section is a seamless structure.

<23> The garment according to any one of <1> to <22>, wherein the tubular joint supporter section further includes a one-end side rib cuff section disposed at an opposite side from the central region as viewed from the one-end side region; and an other-end side rib cuff section disposed at an opposite side from the central region as viewed from the other-end side region.

<24> The garment according to any one of <1> to <23>, further including a fastening belt for fastening a portion of the tubular joint supporter section to a part of the body.

<25> A knee supporter, containing a tubular supporter body, the tubular support body including:
a knee support section that is worn on a part of the leg including a knee and that supports the knee;
a thigh side support section that supports a thigh side with respect to the knee of the leg; and
a shin side support section that supports a shin side with respect to the knee of the leg, wherein:
an average wear pressure A of the knee support section and an average wear pressure B of the thigh side support section and the shin side support section satisfy the relationship: average wear pressure A>average wear pressure B, and
an elongation ratio in an axial direction and an elongation ratio in a circumferential direction measured by a tensile test under conditions of a grip width of 15 mm, a distance between grippers of 15 mm, and a tensile load of 20 N, in at least a partial region R in the thigh side support section and the shin side support section, satisfy the relationship: elongation ratio in axial direction>elongation ratio in circumferential direction.

<26> The knee supporter according to <25>, wherein the average wear pressure A and the average wear pressure B satisfy the relationship: average wear pressure A−average wear pressure B≥0.8 kPa.

<27> The knee supporter according to <25> or <26>, wherein the average wear pressure A and the average wear pressure B satisfy the relationship: average wear pressure A−average wear pressure B≥1.0 kPa.

<28> The knee supporter according to any one of <25> to <27>, wherein the elongation ratio in the axial direction is 150% or higher.

<29> A knee supporter, containing a tubular supporter body, the tubular support body including:

a knee support section that is worn on a part of the leg including a knee and that supports the knee;

a thigh side support section that supports a thigh side with respect to the knee of the leg; and a shin side support section that supports a shin side with respect to the knee of the leg, wherein:

an average wear pressure A of the knee support section and an average wear pressure B of the thigh side support section and the shin side support section satisfy the relationship: average wear pressure A>average wear pressure B, and an elongation ratio in an axial direction measured by a tensile test under conditions of a grip width of 15 mm, a distance between grippers of 15 mm, and a tensile load of 20 N, in at least a partial region R in the thigh side support section and the shin side support section, is 150% or higher.

<30> The knee supporter according to <29>, wherein the average wear pressure A and the average wear pressure B satisfy the relationship: average wear pressure A−average wear pressure B≥0.8 kPa.

<31> The knee supporter according to <29> or <30>, wherein the average wear pressure A and the average wear pressure B satisfy the relationship: average wear pressure A−average wear pressure B≥1.0 kPa.

<32> The knee supporter according to any one of <25> to <31>, wherein the region R includes at least an area having a width of 100 mm centering on an extension line extending in the axial direction from a position Y, which corresponds to a center of a popliteal part.

<33> A knee supporter, containing a tubular supporter body, the tubular support body including:

a knee support section that is worn on a part of the leg including a knee and supports the knee;

a thigh side support section that supports a thigh side with respect to the knee of the leg; and a shin side support section that supports a shin side with respect to the knee of the leg, wherein:

an average wear pressure A of the knee support section and an average wear pressure B of the thigh side support section and the shin side support section satisfy the relationship: average wear pressure A>average wear pressure B, and when the knee support section is stretched with a force of 5 kg in a direction in which a distance will increase between a position X, which corresponds to a center of the kneecap in the knee support section, and a position Y, which corresponds to a center of a popliteal part in the knee support section, an elongation percentage of the knee support section is from 180% to 280%.

The knee supporter according to <33> is preferably any one of the knee supporter according to <25> to <32>. That is, in the knee supporter according to any one of <25> to <32> in a case in which the knee support section is stretched with a force of 5 kg in the direction in which the distance between position X corresponding to the center of the kneecap in the knee support section, and position Y corresponding to the center of the popliteal part in the knee support section, will be lengthened, the elongation percentage of the knee support section is preferably from 180% to 280%.

<34> The knee supporter according to <33>, wherein when an elongation ratio in a circumferential direction is measured by a tensile test under conditions of a grip width of 15 mm, a distance between grippers of 15 mm, and a tensile load of 20 N, at each of three points in total, the three points being: the position X corresponding to the center of a kneecap in the knee support section; the position Y corresponding to the center of the popliteal part in the knee support section; and an intermediate position between the position X and the position Y, the three measured values are all included in a range of from 100% to 250%, and a difference between a maximum value and a minimum value among the three measured values is from 0% to 80%.

<35> The knee supporter according to any one of <25> to <34>, wherein the average wear pressure B is 0.1 kPa or greater.

<36> The knee supporter according to any one of <25> to <35>, wherein the average wear pressure A is 2.6 kPa or greater.

<37> The knee supporter according to any one of <25> to <36>, wherein:

the average wear pressure A and an average wear pressure B1 of the thigh side support section satisfy the relationship: average wear pressure A>average wear pressure B1, and the average wear pressure A and an average wear pressure B2 of the shin side support section satisfy the relationship: average wear pressure A>average wear pressure B2.

<38> The knee supporter according to any one of <25> to <37>, wherein:

the average wear pressure A and the average wear pressure B1 of the thigh side support section satisfy the relationship: average wear pressure A−average wear pressure B1≥0.8 kPa, and the average wear pressure A and the average wear pressure B2 of the shin side support section satisfy the relationship: average wear pressure A−average wear pressure B2≥0.8 kPa.

<39> The knee supporter according to any one of <25> to <38>, wherein:

the average wear pressure A and the average wear pressure B1 of the thigh side support section satisfy the relationship: average wear pressure A−average wear pressure B1≥1.0 kPa, and the average wear pressure A and the average wear pressure B2 of the shin side support section satisfy the relationship: average wear pressure A−average wear pressure B2≥1.0 kPa.

<40> The knee supporter according to any one of <25> to <39>, wherein:

the knee support section has a length in the axial direction of from 60 mm to 200 mm, the thigh side support section has a length in the axial direction of from 30 mm to 200 mm, and the shin side support section has a length in the axial direction of from 30 mm to 200 mm.

<41> The knee supporter according to any one of <25> to <40>, wherein, when an elongation ratio in the circumferential direction is measured by a tensile test under conditions of a grip width of 15 mm, a distance between grippers of 15 mm, and a tensile load of 20 N, for each of: a measurement area X1 centering on a position X, which corresponds to the center of a kneecap in the knee support section; a measurement area T1 centering on a position T, which is the center in the axial direction of the thigh side support section on an extension line extending in the axial direction from a position Y corresponding to the center of a popliteal part; and a measurement area S1 centering on position S, which is the center in the axial direction of the shin side support section on the extension line extending in the axial direction from the position Y corresponding to the center of the popliteal part, an elongation ratio in the circumferential direction of the measurement area X1 is lower than an elongation ratio in the circumferential direction of the measurement area T1 and is lower than an elongation ratio in the circumferential direction of the measurement area S1.

<42> The knee supporter according to any one of <25> to <41>, wherein, when an elongation ratio in the axial direction is measured by a tensile test under conditions of a grip width of 15 mm, a distance between grippers of 15 mm, and a tensile load of 20 N, for each of: a measurement area X1 centering on a position X, which corresponds to the center of a kneecap in the knee support section; a measurement area T1 centering on a position T, which is the center in the axial direction of the thigh side support section on an extension line extending in the axial direction from a position Y corresponding to the center of a popliteal part; and a measurement area S1 centering on a position S, which is the center in the axial direction of the shin side support section on the extension line extending in the axial direction from the position Y corresponding to the center of the popliteal part, an elongation ratio in the axial direction of the measurement area X1 is lower than an elongation ratio in the axial direction of the measurement area T1 and is lower than an elongation ratio in the axial direction of the measurement area S1.

<43> The knee supporter according to any one of <25> to <42>, wherein at least the thigh side support section, the knee support section, and the shin side support section are continuously produced by circular knitting.

<44> The knee supporter according to any one of <25> to <43>, wherein an overall structure of at least the thigh side support section, the knee support section, and the shin side support section is a seamless structure.

<45> The knee supporter according to any one of <25> to <44>, wherein the tubular supporter body further includes: a thigh side rib cuff section disposed at an opposite side from the knee support section as viewed from the thigh side support section; and a shin side rib cuff section disposed at an opposite side from the knee support section as viewed from the shin side support section.

Advantageous Effects of Invention

According to the first and second embodiments of the invention, there are provided knee supporters that have an excellent feeling of support and excellent fitting comfort when worn on a part of the leg including the knee, and have excellent conformity to the bending and stretching movement of the knee joint (movement conformity).

According to the third embodiment of the invention, there is provided a knee supporter that provides an excellent feeling of support and excellent fitting comfort when worn on a part of the leg including the knee, and provides excellent ease of bending and stretching of the knee joint.

According to the fourth embodiment of the invention, there is provided a garment including a joint supporter section that provides an excellent feeling of support and excellent fitting comfort when worn on a joint area, and alleviates stress on the skin (hereinafter, also referred to as "garment").

DESCRIPTION OF EMBODIMENTS

Figure 1:
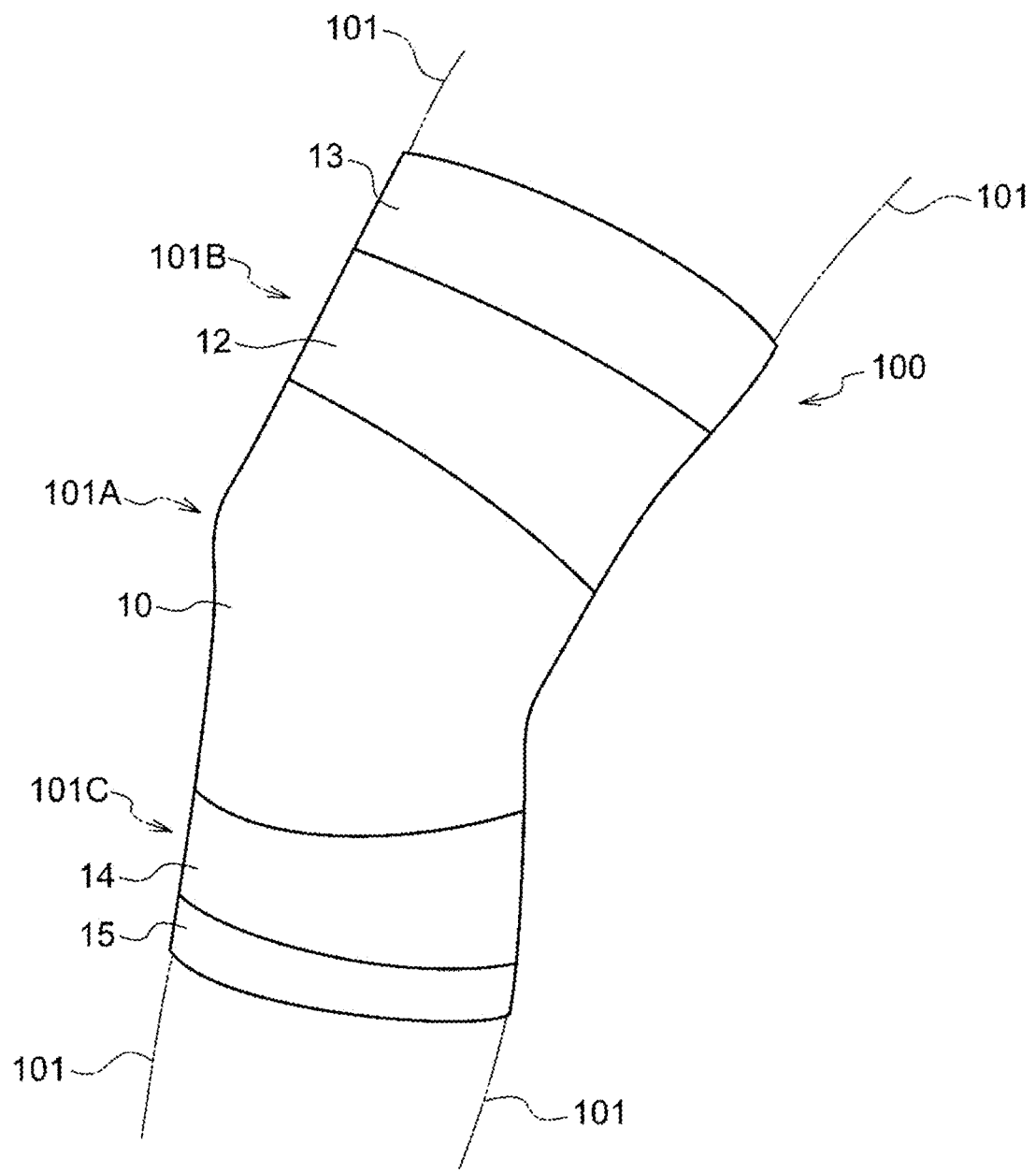
FIG. 1 is a schematic diagram, as viewed from a lateral side, illustrating a knee supporter (supporter body) according to a specific example of the first embodiment and the second embodiment in a state of being worn on a part of the leg including the knee.

Hereinafter, the first embodiment to the fourth embodiment of the invention will be explained.

In the present specification, the notation "to" expressing a numerical range indicates a range including the numerical values before and after "to", as the minimum value and the maximum value, respectively.

In the present specification, an "axial direction of the tubular supporter body" refers to the axial direction of the tubular shape when the shape of the tubular supporter body is held in a tubular shape. In the present specification, an "axial direction of the tubular supporter body" may be simply referred to as "axial direction". The "axial direction" according to the present specification is a direction which may be referred to as "longitudinal direction" in the technical field of knee supporters, and this can also be referred to as a direction in which a leg will be inserted with respect to the tubular supporter body.

In the present specification, a "circumferential direction of the tubular supporter body" refers to the circumferential direction when the shape of the tubular supporter body is held in a tubular shape. In the present specification, a "circumferential direction of the tubular supporter body" may be simply referred to as "circumferential direction". The "circumferential direction" according to the present specification is a direction that may be referred to as "transverse direction" in the technical field of knee supporters.

In the present specification, the kneecap side of a leg may be referred to as "frontal face" or "front face", and the popliteal part of the leg (so-called knee back) may be referred to as "rear face" or "back face".

In the present specification, the direction on the hip joint side as viewed from the kneecap may be referred to as "upside", and the direction on the ankle side as viewed from the kneecap may be referred to as "downside".

In the present specification, a value obtained by subtracting an average wear pressure B from an average wear pressure A (that is, the value of "average wear pressure A−average wear pressure B") may be referred to as "wear pressure difference [average wear pressure A−average wear pressure B]", a value obtained by subtracting an average wear pressure B1 from an average wear pressure A (that is, the value of "average wear pressure A−average wear pressure B1") may be referred to as "wear pressure difference [average wear pressure A−average wear pressure B1]", and a value obtained by subtracting an average wear pressure B2 from an average wear pressure A (that is, the value of "average wear pressure A−average wear pressure B2") may be referred to as "wear pressure difference [average wear pressure A−average wear pressure B2]".

First Embodiment and Second Embodiment

The knee supporter according to the first embodiment of the invention contains a tubular supporter body, the tubular support body including: a knee support section that is worn on a part of the leg including a knee and that supports the knee; a thigh side support section that supports a thigh side with respect to the knee of the leg; and a shin side support section that supports a shin side with respect to the knee of the leg, in which an average wear pressure A of the knee support section and an average wear pressure B of the thigh side support section and the shin side support section satisfy the relationship: average wear pressure A>average wear pressure B, and an elongation ratio in an axial direction and an elongation ratio in a circumferential direction measured by a tensile test under conditions of a grip width of 15 mm, a distance between grippers of 15 mm, and a tensile load of 20 N, in at least a partial region R in the thigh side support section and the shin side support section, satisfy the relationship: elongation ratio in axial direction>elongation ratio in circumferential direction.

In regard to the knee supporter according to the first embodiment, it is preferable that the elongation ratio in the axial direction is 150% or higher.

The knee supporter according to the second embodiment of the invention contains a tubular supporter body, the tubular support body including: a knee support section that is worn on a part of the leg including a knee and that supports the knee; a thigh side support section that supports a thigh side with respect to the knee of the leg; and a shin side support section that supports a shin side with respect to the knee of the leg, in which an average wear pressure A of the knee support section and an average wear pressure B of the thigh side support section and the shin side support section satisfy the relationship: average wear pressure A>average wear pressure B, and an elongation ratio in an axial direction measured by a tensile test under conditions of a grip width of 15 mm, a distance between grippers of 15 mm, and a tensile load of 20 N, in at least a partial region R in the thigh side support section and the shin side support section, is 150% or higher.

As a result of the investigation of the present inventors, it has become clear that when a knee supporter includes a tubular supporter body including a knee support section that supports the knee; a thigh side support section that supports the thigh side with respect to the knee of the leg; and a shin side support section that supports the shin side with respect to the knee of the leg, and an average wear pressure A of the knee support section and an average wear pressure B of the thigh side support section and the shin side support section satisfy the relationship: average wear pressure A>average wear pressure B (that is, in a case in which an average wear pressure A of the knee support section is higher than an average wear pressure B of the thigh side support section and the shin side support section), a feeling of support and fitting comfort for the leg as bodily sensations of the wearer are particularly enhanced.

The reason for this is not clearly known; however, it is speculated to be because when the relationship: average wear pressure A>average wear pressure B is satisfied, a wearer wearing this knee supporter feels a sensation that the knee supported by the knee support section is supported at a higher wear pressure than the actual average wear pressure A (that is, sensory illusion).

Furthermore, as a result of the investigation of the present inventors, it has also be made clear that in a case in which the relationship: average wear pressure A>average wear pressure B is satisfied, a feeling of support and fitting comfort are enhanced; however, the conformity of the knee supporter to the bending and stretching movement of the knee joint (hereinafter, also referred to as "movement conformity") may be impaired.

The present inventors further conducted an investigation, and as a result, the inventors found that even in a case in which the relationship: average wear pressure A>average wear pressure B is satisfied, when at least one of the following (1) or (2) is satisfied in at least a partial region R of the thigh side support section and the shin side support section, the movement conformity as a bodily sensation of the wearer is improved:

(1) an elongation ratio in an axial direction and an elongation ratio in a circumferential direction measured by a tensile test under conditions of a grip width of 15 mm, a distance between grippers of 15 mm, and a tensile load of 20 N satisfy the relationship: elongation ratio in axial direction>elongation ratio in circumferential direction; or (2) the elongation ratio in the axial direction measured by a tensile test under the conditions disclosed in item (1) is 150% or higher.

Therefore, the knee supporter according to the first embodiment and the second embodiment provides an excellent feeling of support and excellent fitting comfort when worn on a part of the leg including the knee, and also has excellent conformity to the bending and stretching movement of the knee joint (movement conformity).

According to the present specification, an "average wear pressure" means the average value of the wear pressure (tightening pressure exerted by the supporter body).

A specific measurement method of the average wear pressure A, the average wear pressure B, the average wear pressure B1, and the average wear pressure B2 according to the present specification will be described below.

In the knee supporter of the present embodiments (that is, the knee supporter according to the first embodiment and the second embodiment; hereinafter, the same), an average wear pressure A of the knee support section and an average wear pressure B of the thigh side support section and the shin side support section satisfy the relationship: average wear pressure A>average wear pressure B. In other words, in the knee supporter of the present embodiments, a wear pressure difference [average wear pressure A−average wear pressure B] exceeds zero (0).

The wear pressure difference [average wear pressure A−average wear pressure B] is preferably 0.8 kPa or higher, more preferably 1.0 kPa or higher, and particularly preferably 1.2 kPa or higher, from the viewpoint of further enhancing a feeling of support and fitting comfort.

Meanwhile, the wear pressure difference [average wear pressure A−average wear pressure B] is preferably 3.5 kPa or lower, more preferably 3.3 kPa or lower, even more preferably 3.0 kPa or lower, still more preferably 2.8 kPa, and particularly preferably 2.5 kPa, from the viewpoint of further enhancing comfortableness by suppressing excessive compression.

According to the present specification, unless particularly stated otherwise, the "elongation ratio" refers to an elongation ratio measured by a tensile test under conditions of a grip width of 15 mm, a distance between grips of 15 mm, and a tensile load of 20 N.

The "elongation ratio" refers to a value calculated by the following Formula (1).

Elongation ratio (%)=($L_{20}/L_0$)×100   Formula (1)

wherein in Formula (1), $L_0$ represents an initial distance between grips (that is, upon non-stretching), and specifically, $L_0$ represents 15 mm; and $L_{20}$ represents a distance between grips in a state in which a tensile load of 20 N has been applied (that is, upon stretching).

The tensile test for measuring the elongation ratio is carried out by fastening a portion of a knee supporter to a tensile testing machine at a grip width of 15 mm and a distance between grips of 15 mm, and performing the tensile test at a tensile rate of 15 mm/min.

In regard to the tensile test, in a case in which it is difficult to perform the test for a portion of the knee supporter, a specimen that measures 30 mm on each side may be cut out from the knee supporter, and the test may be carried out using the specimen thus cut out. Furthermore, in regard to the tensile test, a specimen that has the same configuration (same knitting) as the knee supporter and measures 30 mm on each side may be produced, and the tensile test may be carried out using the specimen thus produced.

The number of times of the test is set to 5 times, and an average value is determined from three measured values remaining after excluding the maximum value and the minimum value from the measured values obtained in 5 times. This average value is employed as the "elongation ratio".

Regarding the apparatus of the tensile test, a general tensile testing machine can be used; however, for example, an autograph "AGS-X 1 kN" manufactured by Shimadzu Corp. can be used.

In the region R of the knee supporter according to the first embodiment, the relationship: elongation ratio in axial direction>elongation ratio in circumferential direction is satisfied as described above. In other words, in the knee supporter according to the first embodiment, a ratio of an elongation ratio in axial direction with respect to an elongation ratio in circumferential direction (hereinafter, also referred to as "ratio [elongation ratio in axial direction/elongation ratio in circumferential direction]") is greater than 1. Thereby, the movement conformity is enhanced.

The ratio [elongation ratio in axial direction/elongation ratio in circumferential direction] is preferably 1.2 or greater, and more preferably 1.4 or greater, from the viewpoint of further enhancing the movement conformity.

Meanwhile, the ratio [elongation ratio in axial direction/elongation ratio in circumferential direction] is preferably 5.0 or lower, more preferably 3.8 or lower, and particularly preferably 3.2 or lower, from the viewpoints of a feeling of support and fitting comfort.

Furthermore, in the region R of the knee supporter according to the first embodiment, an elongation ratio in axial direction and an elongation ratio in circumferential direction satisfies the relationship: elongation ratio in axial direction>elongation ratio in circumferential direction; however, from the viewpoint of further enhancing the movement conformity, it is preferable that the relationship: elongation ratio in axial direction>elongation ratio in circumferential direction+100 is satisfied; it is more preferable that the relationship: elongation ratio in axial direction>elongation ratio in circumferential direction+200 is satisfied; and it is even more preferable that the relationship: elongation ratio in axial direction>elongation ratio in circumferential direction+250 is satisfied.

An elongation ratio in axial direction in the region R of the knee supporter according to the first embodiment and the second embodiment is more preferably 200% or higher, even more preferably 300% or higher, still more preferably 400% or higher, even more preferably 500% or higher, and still more preferably 600% or higher.

According to the present specification, when it is simply described as "elongation ratio", this means both the elongation ratio in axial direction (longitudinal direction) and the elongation ratio in circumferential direction (transverse direction).

Hereinafter, more preferred configurations of the knee supporter of the present embodiment (that is, knee supporter according to the first embodiment and the second embodiment; hereinafter, the same) will be explained.

An average wear pressure B is not particularly limited as long as the value is 0 kPa or higher; however, from the viewpoint of further enhancing a feeling of support and comfortableness, the average wear pressure B is preferably 0.1 kPa or higher.

The average wear pressure B is more preferably 0.5 kPa or higher, and even more preferably 1.0 kPa or higher.

An average wear pressure A is not particularly limited as long as the relationship: average wear pressure A>average wear pressure B is satisfied. From the viewpoint of further enhancing a feeling of support and comfortableness, the average wear pressure A is preferably 1.5 kPa or higher, more preferably 2.0 kPa or higher, and even more preferably 2.6 kPa or higher.

The upper limit of the average wear pressure A is not particularly limited; however, from the viewpoint of further enhancing comfortableness by suppressing excessive compression, the average wear pressure A is preferably 10.0 kPa or lower, and more preferably 8.0 kPa or lower.

Furthermore, in the present embodiment, from the viewpoint of further enhancing a feeling of support and fitting comfort for the leg, it is preferable that the average wear pressure A of the knee support section and the average wear pressure B1 of the thigh side support section satisfy the relationship: average wear pressure A>average wear pressure B1, it is more preferable that the relationship: average wear pressure A−average wear pressure B1≥0.8 kPa is satisfied; and it is particularly preferable that the relationship: average wear pressure A−average wear pressure B1≥1.0 kPa is satisfied.

In the present embodiment, from the viewpoint of further enhancing a feeling of support and fitting comfort for the leg, it is preferable that the average wear pressure A of the knee support section and the average wear pressure B2 of the shin side support section satisfy the relationship: average wear pressure A>average wear pressure B2; it is more preferable that the relationship: average wear pressure A−average wear pressure B2≥0.8 kPa is satisfied; and it is particularly preferable that the relationship: average wear pressure A−average wear pressure B2≥1.0 kPa is satisfied.

In the present embodiment, from the viewpoint of particularly enhancing a feeling of support and fitting comfort for the leg, it is preferable that the average wear pressure A and the average wear pressure B1 satisfy the relationship: average wear pressure A>average wear pressure B1, and the average wear pressure A and the average wear pressure B2 satisfy the relationship: average wear pressure A>average wear pressure B2;

it is more preferable that the average wear pressure A and the average wear pressure B1 satisfy the relationship: average wear pressure A−average wear pressure B1≥0.8 kPa, and the average wear pressure A and the average wear pressure B2 satisfy the relationship: average wear pressure A−average wear pressure B2≥0.8 kPa; and it is particularly preferable that the average wear pressure A and the average wear pressure B1 satisfy the relationship: average wear pressure A−average wear pressure B1≥1.0 kPa, and the average wear pressure A and the average wear pressure B2 satisfy the relationship: average wear pressure A−average wear pressure B2≥1.0 kPa.

The average wear pressure B1 is not particularly limited as long as the value is 0 kPa or greater; however, from the viewpoint of further enhancing a feeling of support and comfortableness, it is preferable that the average wear pressure B1 is 0.1 kPa or greater.

The average wear pressure B1 is more preferably 0.5 kPa or greater, and even more preferably 1.0 kPa or greater.

The average wear pressure B2 is not particularly limited as long as the value is 0 kPa or greater; however, from the viewpoint of further enhancing a feeling of support and comfortableness, it is preferable that the average wear pressure B2 is 0.1 kPa or greater.

The average wear pressure B2 is more preferably 0.5 kPa or greater, and even more preferably 1.0 kPa or greater.

The knee supporter of the present embodiment is preferably such that in a case in which the knee support section is stretched with a force of 5 kg in a direction in which a distance will increase between a position X, which corresponds to a center of the kneecap in the knee support section, and a position Y, which corresponds to a center of a popliteal part in the knee support section, an elongation percentage of the knee support section is from 180% to 280%.

When the elongation percentage of the knee support section is 180% or higher, bending and stretching of the knee joint become easier as a bodily sensation of the wearer.

When the elongation percentage of the knee support section is 280% or lower, a strong feeling of support for the knee as a bodily sensation of the wearer is maintained.

Here, the elongation percentage of the knee support section means the ratio (%) of the stretched size of the knee support section (that is, the length of the knee support section after performing the stretching operation described above) with respect to the resting size of the knee support section (that is, the length of the knee support section before performing the stretching operation described above).

Here, the resting size of the knee support section will be explained with reference to FIG. 7, and the stretched size of the knee support section will be explained with reference to FIG. 8.

Figure 7:
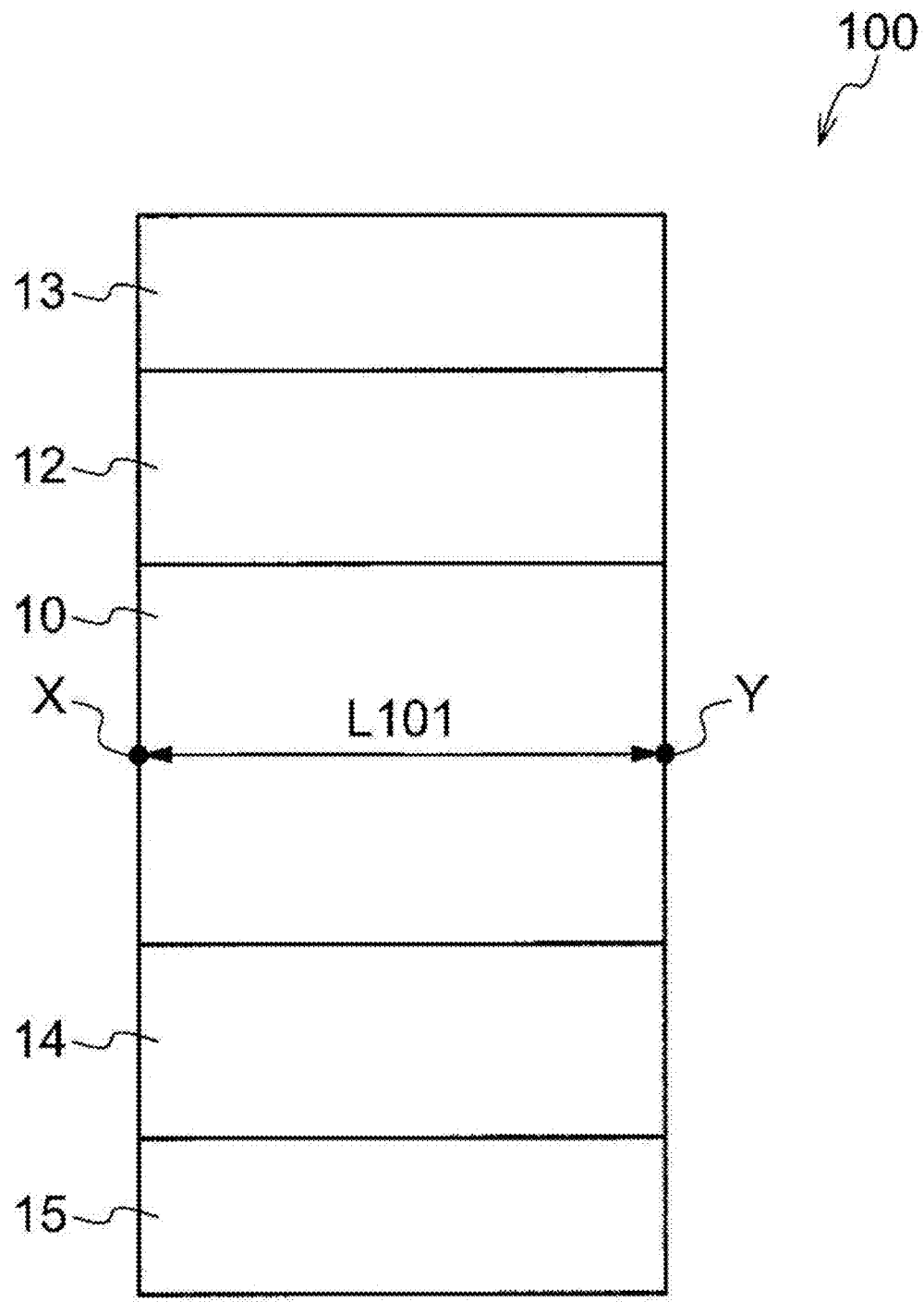
FIG. 7 is a conceptual diagram illustrating a knee supporter according to a specific example of the first embodiment and the second embodiment in a state of being placed flat such that the right side and the left side of the knee supporter overlap each other.

FIG. 7 is a conceptual diagram illustrating a state in which a knee supporter is placed flat such that the right side and the left side of the knee supporter overlap each other.

When the resting size is measured, first, as illustrated in FIG. 7, the knee supporter 100 is placed flat on a horizontal table such that the right-hand side and the left-hand side of the knee supporter 100 overlap each other, and position X and position Y are disposed at two ends. Subsequently, an acrylic plate (not shown in the diagram; for example, ACRYLITE EX-001 manufactured by Mitsubishi Chemical Corp.) having a size of 350 mm×350 mm×5 mm is mounted on the knee supporter 100, and in this state, the distance between the position X and the position Y is measured. The distance between the position X and the position Y thus measured is designated as resting size L101.

Figure 8:
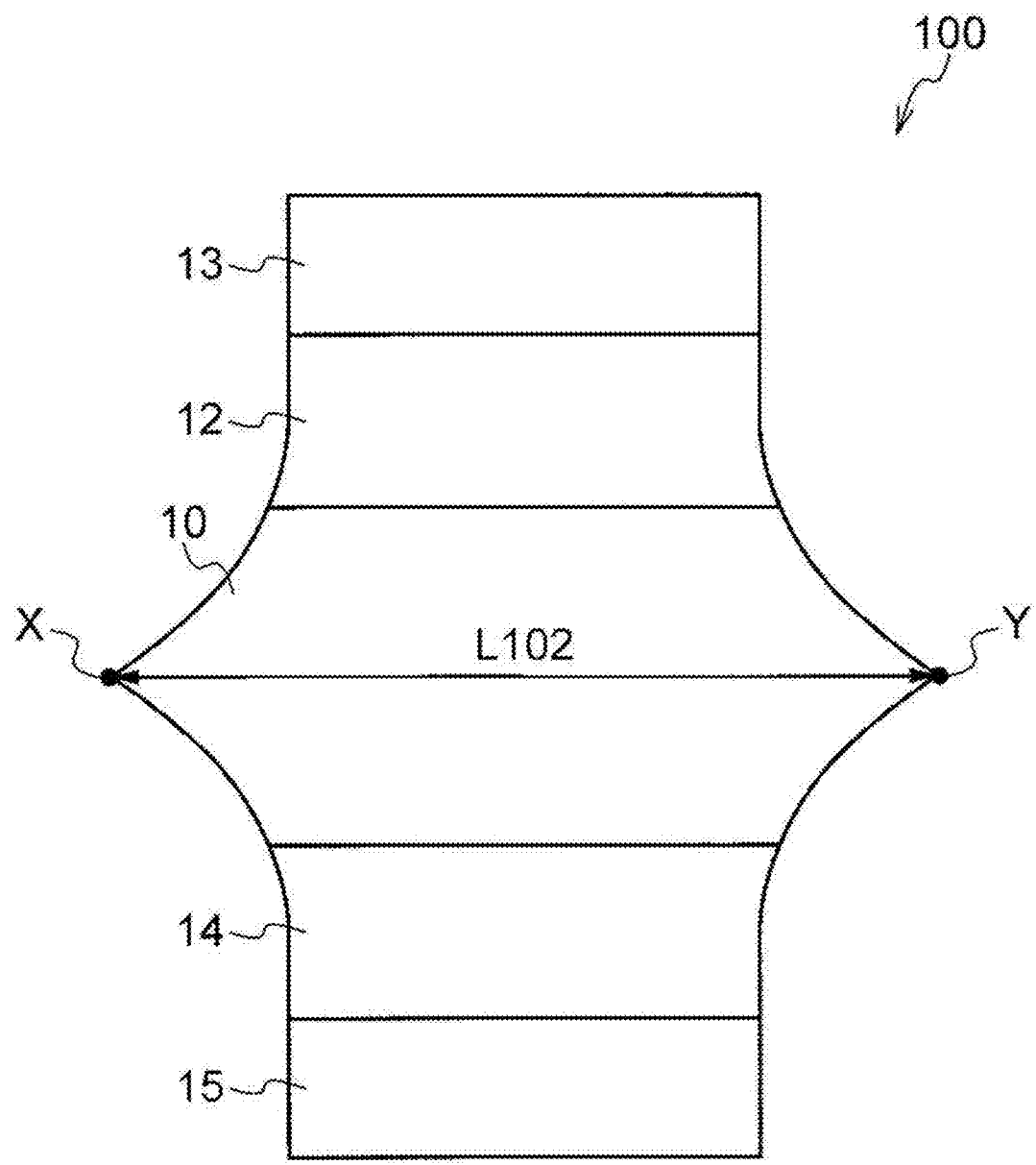
FIG. 8 is a conceptual diagram illustrating a knee supporter according to a specific example of the first embodiment and the second embodiment in a state of being stretched in a direction in which the distance between the position X and the position Y increases.

FIG. 8 is a conceptual diagram illustrating a state in which the knee supporter is stretched in a direction in which the distance between position X and position Y will increase.

When the stretched size is measured, first, a pair of L-shaped arms for measuring a stretched size, which moves relatively in a direction in which the distance between the respective arms will increase. The pair of L-shaped arms (not shown in the diagram) is inserted into the internal space of a knee supporter 100, the protrusion part of one of the L-shaped arms is disposed at position X, and the protrusion part of another one of the L-shaped arms is disposed at position Y. Subsequently, one of the L-shaped arms and another one of the L-shaped arms are moved relatively to each other in a direction in which the distance between the arms will increase, and thereby, the knee support section 10 is forcibly stretched from the interior with a force of 5 kg in the direction in which the distance between position X and position Y will increase. The distance between the position X and the position Y in a forcibly stretched state is measured, and this is designated as stretched size L102.

The details of the knee supporter 100 illustrated in FIG. 7 and FIG. 8 will be described in detail later (see FIG. 1 to FIG. 4).

The elongation percentage of the knee support section can be measured using, for example, a "new weight-type dimension measuring device (for socks)" manufactured by Ohtake Works, Ltd.

The upper limit of the elongation percentage of the knee support section is more preferably 260%, and particularly preferably 240%.

In regard to an embodiment in which the elongation percentage of the knee support section is 180% to 280%, it is preferable that when an elongation ratios in a circumferential direction is respectively measured by a tensile test under conditions of a grip width of 15 mm, a distance between grippers of 15 mm, and a tensile load of 20 N at each of three points in total, the three point being: position X, position Y, and an intermediate position between the position X and the position Y, the three measured values are all included in a range of from 100% to 250%, and a difference between a maximum value and a minimum value among the three measured values is from 0% to 80%.

The method of measuring an elongation ratio in a circumferential direction is as described above.

Thereby, a balance is more effectively achieved between the ease of bending and stretching of the knee joint and a high feeling of support for the knee.

An "elongation ratio in a circumferential direction" as used herein is an elongation ratio of a portion in the knee support section, and is an elongation ratio of one sheet of cloth.

In contrast, an "elongation percentage of the knee support section" described above is an elongation percentage of the knee support section as a whole, and is an elongation percentage of two sheets of cloth (right-hand side and left-hand side).

The knee supporter is worn on a part of the leg including the knee (that is, lower limb).

Regarding the length in the axial direction of the knee supporter, a length such that upon wearing, the upper end of the knee supporter is positioned lower than the hip joint, while the lower end of the knee supporter is positioned upper than the ankle, is suitable.

In the following description, preferred ranges of the respective lengths of the knee support section, the thigh side support section, and the shin side support section as viewed from the viewpoint of more effectively manifesting the effects of enhancement of a feeling of support, enhancement of fitting comfort, and enhancement of movement conformity, will be explained.

The length in the axial direction of the knee support section (for example, length in the axial direction L10 in FIG. 3 and FIG. 4 that will be described below) can be set as appropriate; however, from the viewpoint of more effectively manifesting the effects of a feeling of support, fitting comfort, and movement conformity, the length in the axial direction is preferably from 60 mm to 200 mm.

The length in the axial direction of the thigh side support section (for example, length in the axial direction L12 in FIG. 3 and FIG. 4 that will be described below) can be set as appropriate; however, from the viewpoint of more effectively manifesting the effects of a feeling of support, fitting comfort, and movement conformity, the length in the axial direction is preferably from 30 mm to 200 mm.

The length in the axial direction of the shin side support section (for example, length in the axial direction L14 in FIG. 3 and FIG. 4 that will be described below) can be set as appropriate; however, from the viewpoint of more effectively manifesting the effects of a feeling of support, fitting comfort, and movement conformity, the length in the axial direction is preferably from 30 mm to 200 mm.

The length in the axial direction according to the present specification means the length in the axial direction in an unstretched state.

The knee supporter of the present embodiment includes region R as described above.

Region R is at least a partial region in the thigh side support section and the shin side support section, and is a region that satisfies at least one of the following item (1) or (2):

(1) an elongation ratio in axial direction and an elongation ratio in circumferential direction that are measured by a tensile test under conditions of a grip width of 15 mm, a distance between grippers of 15 mm, and a tensile load of 20 N satisfy the relationship: elongation ratio in the axial direction>elongation ratio in the circumferential direction; or (2) an elongation ratio in axial direction measured by a tensile test under conditions disclosed in item (1) is 150% or higher.

The region R may be a partial region in the thigh side support section and the shin side support section, or may be the whole region (entirety) of the thigh side support section and the shin side support section.

When the region R is a partial region in the thigh side support section and the shin side support section, the region R may be at least a partial region in the thigh side support section, may be at least a partial region in the shin side support section, or may be a combination of at least a partial region in the thigh side support section and at least a partial region in the shin side support section (provided that a case in which the region R is the whole region of the thigh side support section and the shin side support section).

When the region R is partial region in the thigh side support section and the shin side support region, it is preferable that the region R is a partial region in a case in which the thigh side support section and the shin side support section are respectively divided into a plurality of regions having different elongation ratios. The "division" as used herein may be division in circumferential direction (that is, division that produces two or more strip-like portions), or may be division in axial direction (that is, division that produces two or more tubular-shaped portions); however, the division is preferably division in circumferential direction.

When the region R is a partial region in the thigh side support section and the shin side support section, it is preferable that the region R includes an extension line extending in the axial direction from position Y, which corresponds to the center of the popliteal part.

It is preferable that the region R includes at least an area having a width of 100 mm centering on the extension line extending in the axial direction from the position Y, which corresponds to the center of the popliteal part (for example, area Y1 and area Y2 in FIG. 4 that will be described below). Thereby, the movement conformity is further enhanced.

The knee supporter is preferably such that when an elongation ratio in the circumferential direction is measured by a tensile test under conditions of a grip width of 15 mm, a distance between grippers of 15 mm, and a tensile load of 20 N, for each of: a measurement area X1 centering on a position X (for example, position X in FIG. 3 that will be described below), which corresponds to the center of a kneecap in the knee support section; a measurement area T1 centering on a position T (for example, position T in FIG. 4 that will be described below), which is the center in the axial direction of the thigh side support section on an extension line extending in the axial direction from a position Y corresponding to the center of a popliteal part; and a measurement area S1 centering on position S (for example, position S in FIG. 4 that will be described below), which is the center in the axial direction of the shin side support section on the extension line extending in the axial direction from the position Y corresponding to the center of the popliteal part, an elongation ratio in the circumferential direction of the measurement area X1 is lower than an elongation ratio in the circumferential direction of the measurement area T1 and is lower than an elongation ratio in the circumferential direction of the measurement area S1. Thereby, the relationship: average wear pressure A>average wear pressure B can be satisfied more easily.

The knee supporter is preferably such that, when an elongation ratio in the axial direction is measured by a tensile test under conditions described above, for each of: a measurement area X1; a measurement area T1; and a measurement area S1, an elongation ratio in the axial direction of the measurement area X1 is lower than an elongation ratio in the axial direction of the measurement area T1 and is lower than an elongation ratio in the axial direction of the measurement area S1. Thereby, the relationship: average wear pressure A>average wear pressure B can be satisfied more easily.

It is preferable that at least the thigh side support section, the knee support section, and the shin side support section are continuously produced by circular knitting. Thereby, an effect that the fitting comfort at the time of wearing is further enhanced, without causing any discomfort caused by the protrusion parts formed by the seam line, compared to a case in which the thigh side support section, the knee support section, and the shin side support section are separately produced, and then these are sewed together. Furthermore, when the thigh side support section, the knee support section, and the shin side support section are continuously produced by circular knitting, an effect that the elongation ratio can be easily secured is also provided.

The shape of the tubular supporter body may be any tubular shape having at least two openings, and besides this, there are no particular limitations.

The shape as viewed in a planar view in a case in which the tubular supporter body is flattened and squashed into an approximately flat shape, may be symmetric or asymmetric about the axial direction, or may be symmetric or asymmetric about the circumferential direction. The shape as viewed in a planar view may be an approximately rectangular shape, or may also be a shape with a portion being curved.

The boundary lines of the thigh side support section, the knee support section, and the shin side support section included in the tubular supporter body may have a straight line shape, or may have a curved or wavy shape.

The knitted structure of the thigh side support section, the knee support section, and the shin side support section may be integrally knitted, or may be knitted non-integrally.

The tubular supporter body may further have holes or slits in some part of the knitted structure.

Furthermore, when attention is focused on at least the overall structure of the thigh side support section, the knee support section, and the shin side support section, from the viewpoint of securing the fitting comfort at the time of wearing and the elongation ratio described above, it is preferable that the overall structure is a seamless structure.

Here, a seamless structure means an integral structure having neither any seams in axial direction (for example, seams for forming a tubular shape by sewing) nor any seams in circumferential direction (for example, seams for sewing various sections).

The entirety of the thigh side support section, the knee support section, and the shin side support section having a seamless structure can be formed by, for example, continuously producing the thigh side support section, the knee support section, and the shin side support section by circular knitting.

The tubular supporter body (preferably, at least one of the thigh side support section or the shin side support section) may include the concave-convex structure region according to a fourth embodiment that will be described below. In regard to a preferred embodiment of the concave-convex structure region in a case in which the tubular supporter body includes a concave-convex region, the fourth embodiment can be referred to.

It is also preferable that the tubular supporter body further includes a thigh side rib cuff section disposed at an opposite side from the knee support section as viewed from the thigh side support section, and a shin side rib cuff section disposed at an opposite side from the knee support section as viewed from the shin side support section. Thereby, slippage upon wearing (for example, slipping down) or rolling up of the supporter body is more effectively suppressed.

In a case in which the tubular supporter body includes a thigh side rib cuff section and a shin side rib cuff section, the thigh side rib cuff section and the shin side rib cuff section may be connected to the thigh side support section and the shin side support section, respectively, by sewing together, or may be continuously produced together with the thigh side support section and the shin side support section by circular knitting.

From the viewpoint of securing the fitting comfort and the elongation ratio at the time of wearing as described above, it is preferable that the thigh side rib cuff section and the shin side rib cuff section are continuously produced together with the thigh side support section and the shin side support section, respectively, by circular knitting.

Also, from the same viewpoint, it is preferable that the overall structure of the thigh side rib cuff section, the thigh side support section, the knee support section, the shin side support section, and the shin side rib cuff section is a seamless structure.

It is also preferable that at least a portion of the back surface of the thigh side rib cuff section (that is, the surface facing the leg; hereinafter, the same) is provided with a resin layer (for example, a silicon rubber layer), from the viewpoint of suppressing slipping down of the knee supporter. The resin layer can be formed by, for example, printing. It is also acceptable that the resin layer is provided on the back surface of the shin side rib cuff section.

Furthermore, the knee supporter may also include other members in addition to the supporter body.

Examples of the other members include a rod-shaped supporting member (stay), which is provided at a position corresponding to the flank of the knee and protects the knee by controlling the movement of the knee as appropriate; a fastening belt for fastening the supporter body to the leg or for enhancing a feeling of support; a pocket, and a tag. These may be disposed separately from the supporter body, or may be disposed integrally by being sewed on the supporter sections. The disposition of the other members on the supporter body is not particularly limited.

Among these, particularly when a fastening belt is provided on the surface of the thigh side rib cuff section (surface on the opposite side with respect to the surface facing the leg), slipping down of the knee supporter can be suppressed more effectively. It is preferable that the fastening belt includes a member that adjusts the clamping capacity to the leg (for example, a hook-and-loop fastener, a buckle, a side release buckle, or a wire adjuster).

As one of the other members, a resin may be attached to the surface of the knitted structure of the supporter body. Examples of the method of attaching a resin include spraying, transfer (for example, thermal transfer), resin impregnation, gravure printing, screen printing, rotary printing, thermocompression bonding, and adhesion. Regarding the resin, an elastic resin (for example, a urethane resin) is preferred.

The knee supporter may be worn alone, or after a poultice or a bandage is attached, the knee supporter may be worn over the poultice or bandage.

Specific Example of First Embodiment and Second Embodiment

Next, a specific example of the present embodiments (first embodiment and second embodiment) will be explained with reference to the drawings. However, the present embodiments are not intended to be limited to the following specific example.

In the present specification, an element that appears in common in various drawings will be assigned with the same reference numeral, and any redundant description will not be provided herein.

FIG. 1 is a schematic diagram, as viewed from a lateral side, illustrating a knee supporter according to the specific example in a state of being worn on a part of the leg including the knee.

Figure 2:
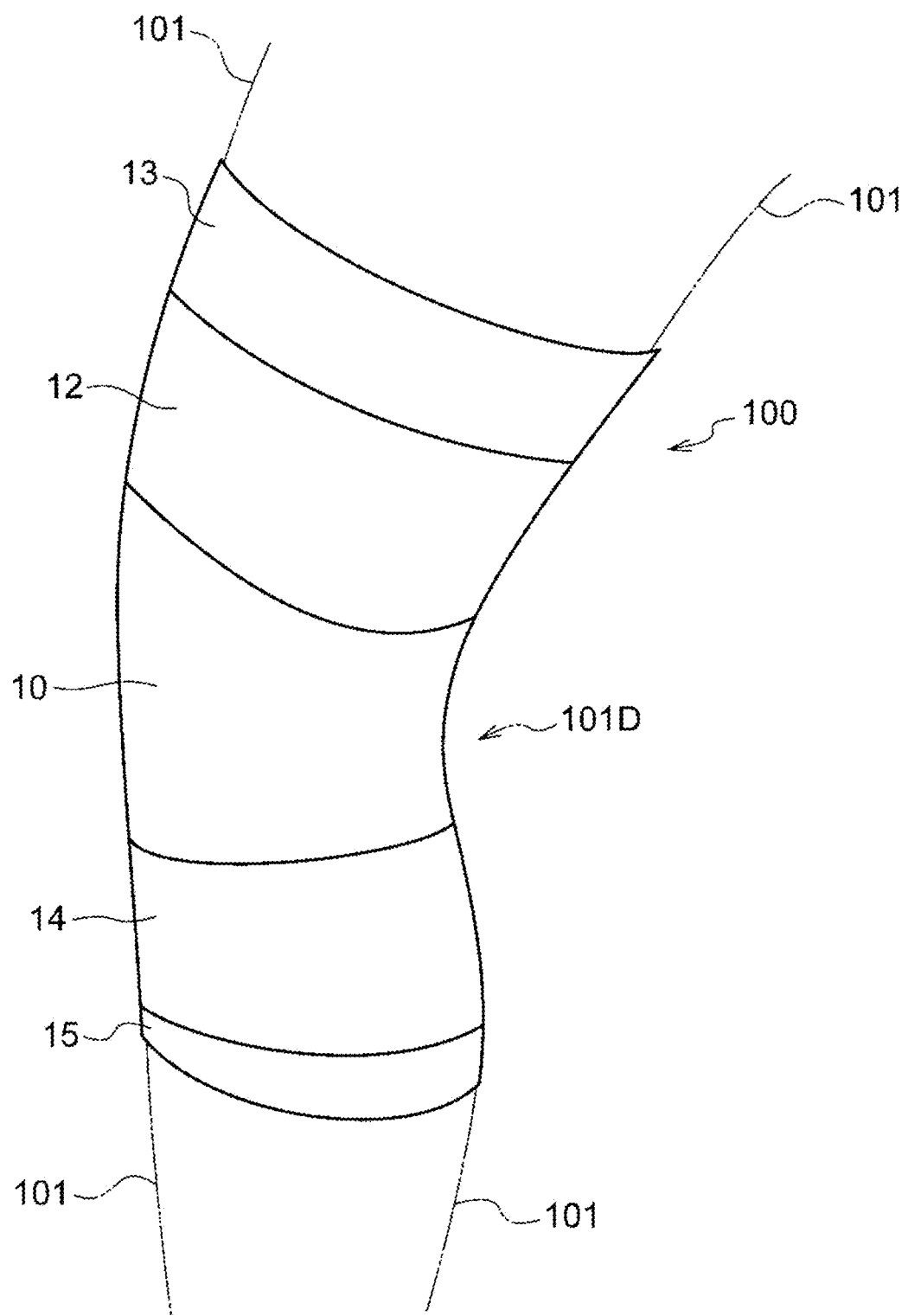
FIG. 2 is a schematic diagram, as viewed from the popliteal side, illustrating a knee supporter (supporter body) according to a specific example of the first embodiment and the second embodiment in a state of being worn on a part of the leg including the knee.

FIG. 2 is a schematic diagram, as viewed from the popliteal side, illustrating a knee supporter according to the specific example in a state of being worn on a part of the leg including the knee.

As illustrated in FIG. 1 and FIG. 2, the knee supporter according to the present specific example includes a tubular supporter body 100, and is used by being worn on a part of the leg 101 including the knee 101A.

The supporter body 100 includes a knee support section 10, a thigh side support section 12, and a shin side support section 14.

The supporter body 100 further includes a thigh side rib cuff section 13 that is disposed at the opposite side from the knee support section 10 as viewed from the thigh side support section 12; and a shin side rib cuff section 15 that is disposed at the opposite side from the knee support section 10 as viewed from the shin side support section 14.

The knee support section 10, the thigh side support section 12, the shin side support section 14, the thigh side rib cuff section 13, and the shin side rib cuff section 15 respectively have a tubular shape, and these are integrated to form the tubular-shaped supporter body 100.

The knee support section 10 is a section that supports the knee 101A and the back of the knee 101D, the thigh side support section 12 is a section that supports a part 101B on the thigh side with respect to the knee 101A of the leg 101, and the shin side support section 14 is a section that supports a part 101C on the shin side with respect to the knee 101A of the leg 101.

The thigh side rib cuff section 13 is a section that is positioned on the opposite side from the knee support section 10 as viewed from the thigh side support section 12 (more particularly, the end on the thigh side of the supporter body 100), and the shin side rib cuff section 15 is a section that is positioned on the opposite side from the knee support section 10 as viewed from the shin side support section 14 (more particularly, the end on the shin side of the supporter body 100).

The thigh side rib cuff section 13 and the shin side rib cuff section 15 have a function of preventing slipping down and rolling up of the supporter body 100 at the time of wearing.

In regard to the supporter body 100, it is not necessarily essential that the boundary lines of the various sections are clearly defined in the external appearance. Even in a case in which the boundary lines of the various sections are not clearly defined in the external appearance, the boundary lines of the various sections can be distinguished by the differences in the elongation ratio of the various sections.

In the supporter body 100, the thigh side rib cuff section 13, the thigh side support section 12, the knee support section 10, the shin side support section 14, and the shin side rib cuff section 15 are continuously produced by circular knitting, and the overall structure of these becomes a seamless structure. Thereby, especially excellent fitting comfort at the time of wearing is obtained.

However, the supporter body 100 may also be produced by sewing the thigh side rib cuff section 13 with the thigh side support section 12, and sewing the shin side rib cuff section 15 with the shin side support section 14.

The present embodiment is not limited to this example, and it is also acceptable that the supporter body is produced by separately producing the various sections as single members, and then sewing together the various sections.

In the supporter body 100, the average wear pressure A of the knee support section 10 and the average wear pressure B of the thigh side support section 12 and the shin side support section 14 satisfy the relationship: wear pressure difference [average wear pressure A–average wear pressure B]>0 kPa.

Furthermore, in the supporter body 100, the average wear pressure A of the knee support section 10 and the average wear pressure B1 of the thigh side support section 12 satisfy the relationship: wear pressure difference [average wear pressure A–average wear pressure B1]>0 kPa.

In the supporter body 100, the average wear pressure A of the knee support section 10 and the average wear pressure B2 of the shin side support section 14 satisfy the relationship: wear pressure difference [average wear pressure A–average wear pressure B2]>0 kPa.

The respective preferred ranges of the wear pressure difference [average wear pressure A–average wear pressure B], the wear pressure difference [average wear pressure A–average wear pressure B1], the wear pressure difference [average wear pressure A–average wear pressure B2], the average wear pressure A, the average wear pressure B, the average wear pressure B1, and the average wear pressure B2 are as described above.

In the supporter body 100, an elongation ratio in circumferential direction of the knee support section 10 is smaller than an elongation ratio in circumferential direction of the thigh side support section 12 and is smaller than an elongation ratio in circumferential direction of the shin side support section 14.

In the supporter body 100, an elongation ratio in axial direction of the knee support section 10 is smaller than an elongation ratio in axial direction of the thigh side support section 12 and is smaller than an elongation ratio in the axial direction of the shin side support section 14.

—Method of Measuring Average Wear Pressure A, Average Wear Pressure B, Average Wear Pressure B1, and Average Wear Pressure B2—

The average wear pressure A, the average wear pressure B, the average wear pressure B1, and the average wear pressure B2 according to the present specification are measured as follows.

First, sensors for measuring wear pressure are attached to 10 sites (positions P1 to P10) of a leg of a mannequin M1 that will be described below.

Figure 5:
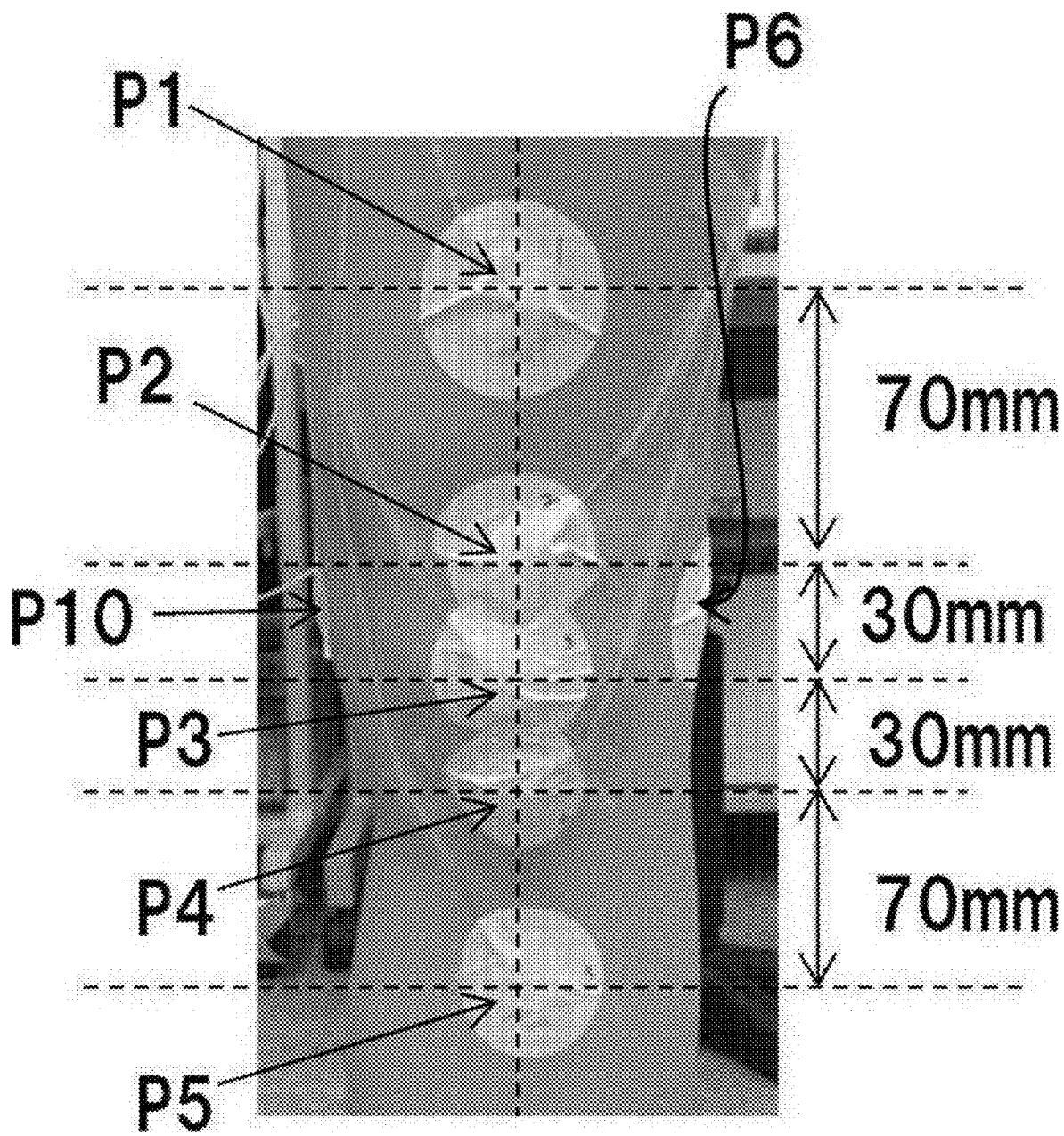
FIG. 5 is a photograph showing the mounting position of a sensor on a mannequin in Test Example 1, the photograph having been taken from the front surface (kneecap side).
Figure 6:
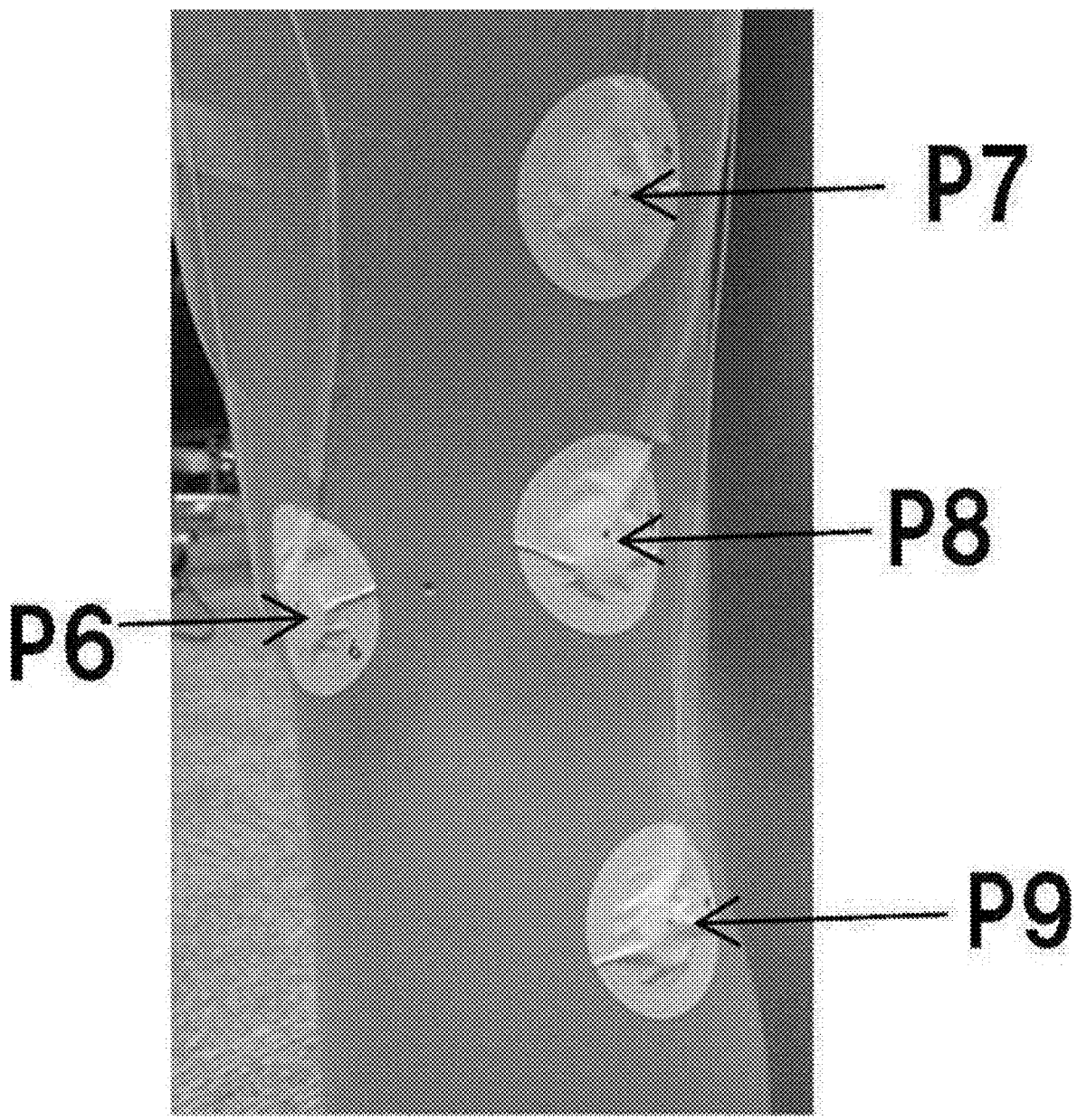
FIG. 6 is a photograph showing the mounting position of a sensor on a mannequin in Test Example 1, the photograph having been taken from the diagonally rear side of a leg of the mannequin.

FIG. 5 and FIG. 6 are photographs showing the positions for sensor attachment to the mannequin M1.

FIG. 5 is a photograph of a leg (left leg) of the mannequin M1 taken from the frontal face (lateral side of the knee), and FIG. 6 is a photograph taken from the diagonally rear side of the leg.

Positions P1 to P10 are particularly the following positions.

Position P1: position at 70 mm to the thigh side on the basis of the position P2 (that is, position at 100 mm to the thigh side on the basis of the position P3)

Position P2: position at 30 mm to the thigh side on the basis of the position P3

Position P3: center of the knee (kneecap)

Position P4: position at 30 mm to the shin side on the basis of the position P3

Position P5: position at 70 mm to the shin side on the basis of the position P4 (that is, position at 100 mm to the shin side on the basis of the position P3)

Positions P6 and P10: transverse side of the leg in the range of from the position P2 to the position P4, respectively Position P7: rear side of the leg with respect to the position P1

Position P8: popliteal side in the range of from the position P2 to the position P4

Position P9: rear side of the leg with respect to the position P5

Regarding the mannequin M1, use is made of a mannequin made of fiber-reinforced plastics (FRP) (for example, manufactured by Nanasai Co., Ltd., product name "MD-20$_A$") having
a circumferential length at the position P1 of 405 mm,
a circumferential length at the position P2 of 370 mm,
a circumferential length at the position P3 of 360 mm,
a circumferential length at the position P4 of 346 mm, and
a circumferential length at the position P5 of 367 mm.

The knee supporter of the present embodiment is worn on a part of the leg including the knee in the mannequin M1, such that the knee support section covers the positions P2, P3, P4, P6, P8, and P10, the thigh side support section covers the positions P1 and P7, and the shin side support section covers the positions P5 and P9.

Next, the wear pressures at the positions P1 to P10 are measured by the sensors for measuring wear pressure mounted at the various positions.

An average value obtained by determining the average values of various measured values for the positions P1, P5, P7, and P9 is designated as average wear pressure B.

An average value obtained by determining the average values of various measured values for the positions P1 and P7 is designated as average wear pressure B1.

An average value obtained by determining the average values of various measured values for the positions P5 and P9 is designated as average wear pressure B2.

An average value obtained by determining the average values of various measured values for the positions P2, P3, P4, P6, P8, and P10 is designated as average wear pressure A.

Furthermore, in the thigh side support section 12 and the shin side support section 14, the relationship: elongation ratio in the axial direction>elongation ratio in the circumferential direction, and the condition of an elongation ratio in the axial direction of 150% or higher are both satisfied.

However, the present embodiment is not limited to this example, and it is acceptable that at least one of the relationship: elongation ratio in the axial direction>elongation ratio in the circumferential direction, or the condition of an elongation ratio in the axial direction of 150% or higher is satisfied in at least a partial region in the thigh side support section and the shin side support section.

Examples of the material of the supporter body 100 include chemical fibers of a polyester, polypropylene, a polyurethane, a polyolefin, a polyolefin-based elastomer, a polyamide, rayon, acrylic, CUPRA, an acetate, PRO-MIX, aramid, and a silicone; natural fibers of cotton, wool, silk, hemp, and rayon; natural rubber; and polyvinyl chloride.

Among them, a polyester, a polyurethane, a polyamide, a polyolefin, a polyolefin-based elastomer, a silicone, or natural rubber is preferred, and from the viewpoint of long-term durability, a polyester, a polyurethane, a polyamide, a polyolefin, or a polyolefin-based elastomer is more preferred.

Examples of the yarn for the supporter body 100 include a monofilament a multifilament, a SCY (Single Covering Yarn) coated with urethane or rubber; and a DCY (Double Covering Yarn) coated with urethane or rubber.

Examples of the knitted structure of the supporter body 100 include a spiral tuck knitted structure, a mesh knitted structure, a three-dimensionally knitted structure, a tricot knitted structure, a plain knitted structure, a ribbing knitted structure, a lace knitted structure, an inlay knitted structure, a cut boss knitted structure, a moss stitch knitted structure, a rib knitted structure, an interlock knitted structure, a float knitted structure, a non-run knitted structure, and a knitted structure formed by combining two or more kinds of knitting methods that form these knitted structures.

Regarding the knitted structure for the knee support section 10 having a high average wear pressure, a spiral tuck knitted structure, a mesh knitted structure, a tricot knitted structure, a plain knitted structure, a ribbing knitted structure, an inlay knitted structure, a cut boss knitted structure, a moss stitch knitted structure, a rib knitted structure, an interlock knitted structure, or a knitted structure formed by combining two or more kinds of knitting methods that form these knitted structures is preferred.

Regarding the knitted structure for the thigh side support section 12 and the shin side support section 14 having a low average wear pressure, a spiral tuck knitted structure, a mesh knitted structure, a three-dimensional knitted structure, a honeycomb wave knitted structure, a plain knitted structure, a ribbing knitted structure, a non-run knitted structure, a lace knitted structure, or a knitted structure formed by combining two or more kinds of knitting methods that form these knitted structures is preferred.

Regarding the knitted structure for the thigh side rib cuff section 13 and the shin side rib cuff section 15, a ribbing knitted structure or a non-run knitted structure is preferred.

A resin may be attached to the surface of the knitted structure of the supporter body 100.

Examples of the method of attaching a resin include spraying, transfer (for example, thermal transfer), resin impregnation, gravure printing, screen printing, rotary printing, thermocompression bonding, and adhesion. The resin is preferably an elastic resin.

The supporter body 100 may also include other structures in addition to knitted structures.

Examples of the other structures include a structure including neoprene rubber, and a structure including a neoprene rubber laminate.

In regard to the material, yarn, and knitted structure of the supporter body 100, for example, the known materials, yarn, and knitted structures described in JP-A No. 2011-130784, JP-A No. 2007-9362, JP-A No. 2010-13765, JP-A No. 2000-116697, and JP-A No. 2007-54126 may be referred to.

Next, an example of the size of the supporter body 100 and a preferred embodiment of the elongation ratio of the supporter body 100 will be explained with reference to FIG. 3 and FIG. 4.

Figure 3:
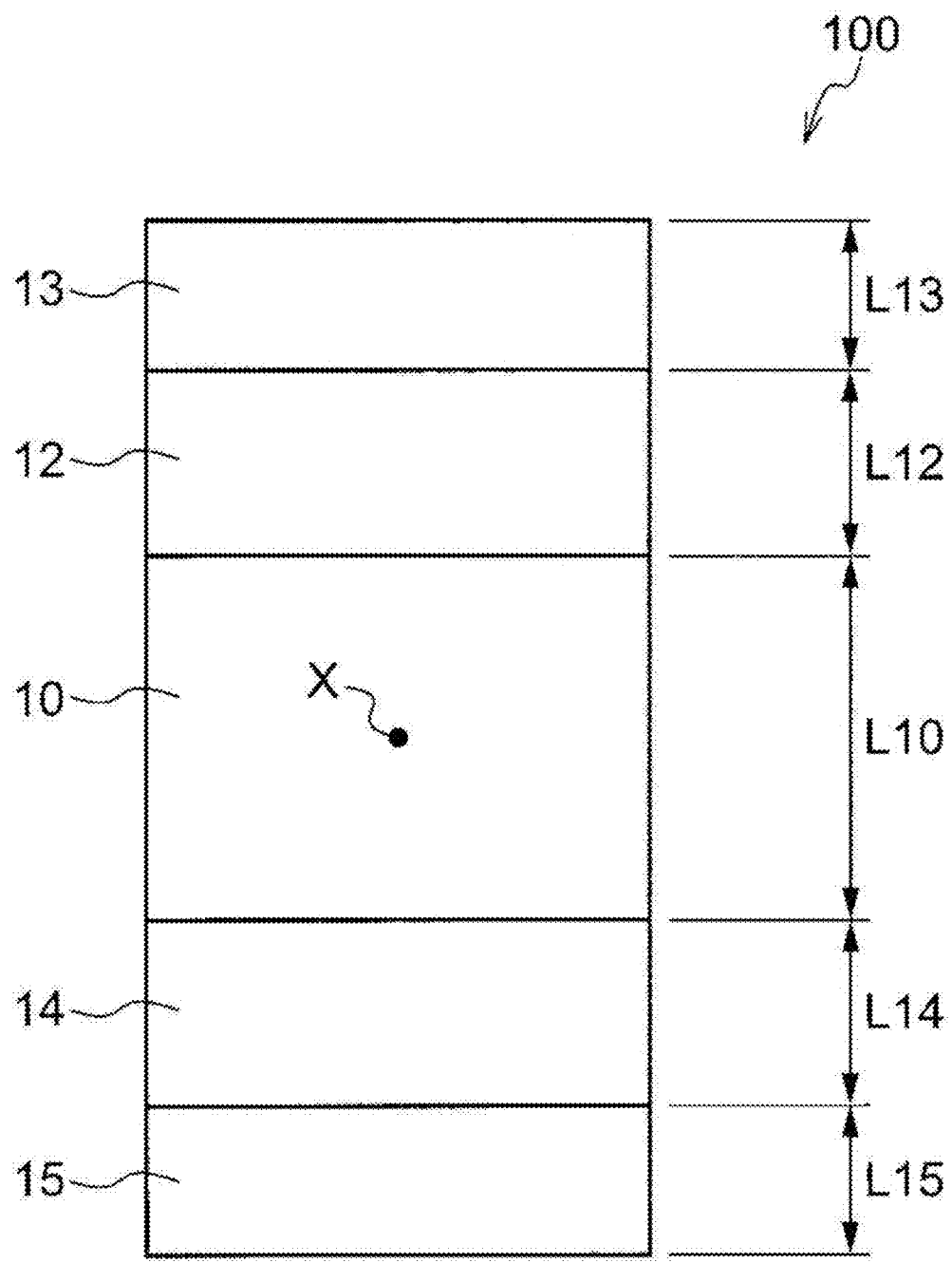
FIG. 3 is a frontal view diagram illustrating a knee supporter (supporter body) according to a specific example of the first embodiment and the second embodiment in a state of not being worn on the leg.
Figure 4:
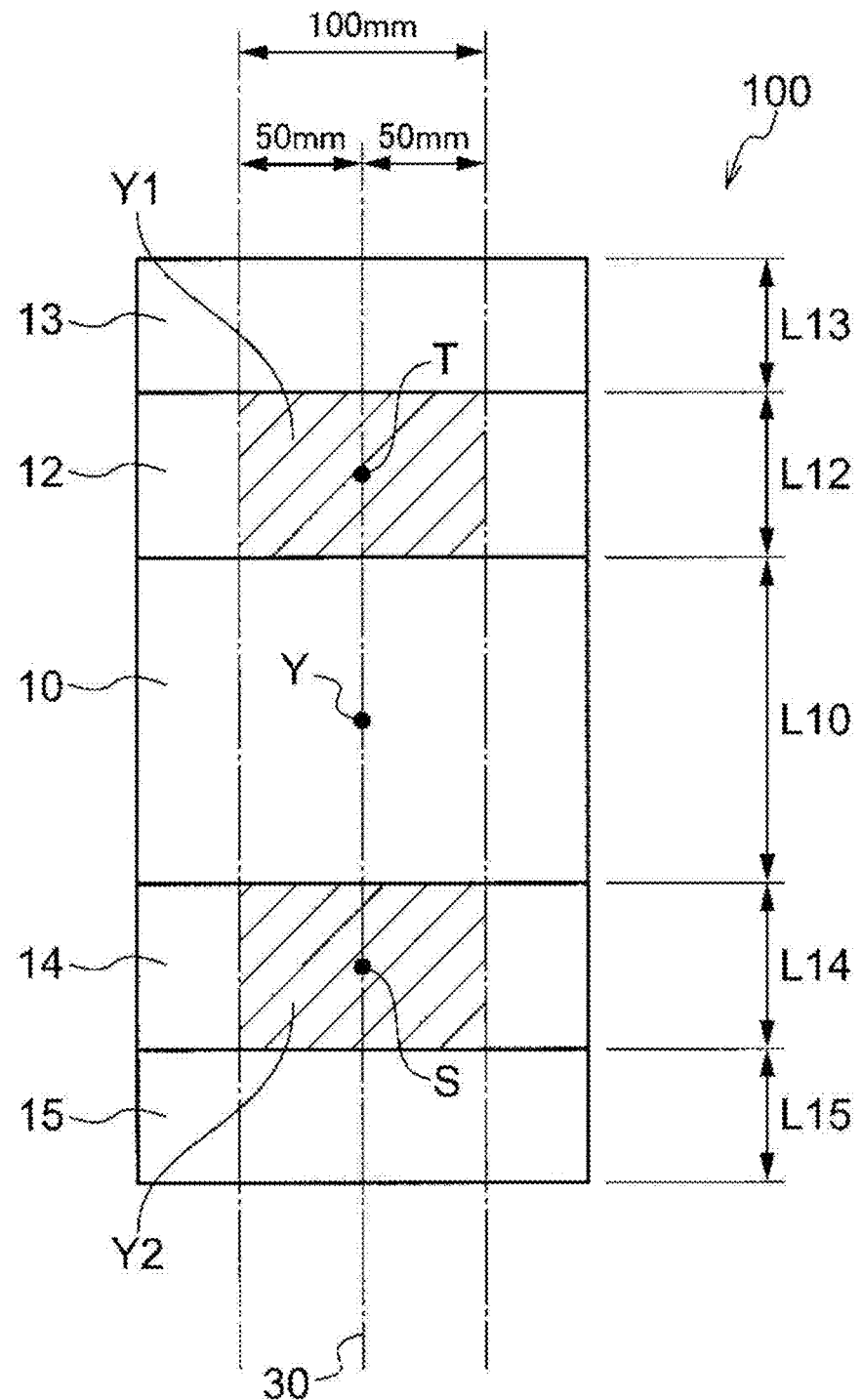
FIG. 4 is a rear view illustrating a knee supporter (supporter body) according to a specific example of the first embodiment and the second embodiment in a state of not being worn on the leg.

FIG. 3 is a frontal view illustrating a knee supporter (supporter body) according to a specific example in a state of not being worn on the leg, and FIG. 4 is a rear view illustrating a knee supporter (supporter body) according to a specific example in a state of not being worn on the leg.

More particularly, FIG. 3 is a frontal view (diagram illustrating the front face side, that is, the kneecap side) at the time of making the shape of the supporter body into an approximately flat shape by overlapping the front face side and the back face side of the supporter body according to a specific example, and FIG. 4 is a rear view (diagram illustrating the back face side, that is, the popliteal side) in this case.

The length in the axial direction L10 of the knee support section 10 is preferably from 60 mm to 200 mm as described above, and more preferably from 80 mm to 180 mm.

The length in the axial direction L12 of the thigh side support section 12 is preferably from 30 mm to 200 mm as described above, and more preferably from 30 mm to 150 mm.

The length in the axial direction L14 of the shin side support section 14 is preferably from 30 mm to 200 mm as described above, and more preferably from 30 mm to 150 mm.

The length in the axial direction L13 of the thigh side rib cuff section 13 is preferably from 10 mm to 80 mm, and more preferably from 20 mm to 70 mm.

The length in the axial direction L15 of the shin side rib cuff section 15 is preferably from 10 mm to 80 mm, and more preferably from 10 mm to 60 mm.

The length in the axial direction of the supporter body 100 (entirety) is preferably from 140 mm to 760 mm, and more preferably from 180 mm to 620 mm.

The average circumferential length of the knee support section 10 is preferably from 100 mm to 300 mm, and more preferably from 150 mm to 280 mm.

The average circumferential length of the thigh side support section 12 is preferably from 100 mm to 400 mm, and more preferably from 150 mm to 350 mm.

The average circumferential length of the shin side support section 14 is preferably from 100 mm to 350 mm, and more preferably from 100 mm to 300 mm.

The average circumferential length of the thigh side rib cuff section 13 is preferably from 180 mm to 350 mm, and more preferably from 200 mm to 320 mm.

The average circumferential length of the shin side rib cuff section 15 is preferably from 100 mm to 350 mm, and more preferably from 120 mm to 300 mm.

Here, the length in the axial direction and the average circumferential length are values represented by the following formulae:

Length in axial direction=(maximum length in axial direction+minimum length in axial direction)/2

Average circumferential length=(maximum circumferential length+minimum circumferential length)/2

Furthermore, in regard to the thigh side support section 12 and the shin side support section 14, it is preferable that the region R that satisfies at least one of the relationship: elongation ratio in axial direction>elongation ratio in circumferential direction, or condition of an elongation ratio in axial direction of 150% or higher, includes at least an area having a width of 100 mm (area Y1 and area Y2 in FIG. 4) centering on an extension line 30 extending in the axial direction from a position Y (position Y in FIG. 4), which corresponds to a center of a popliteal part of the knee support section 10. It is particularly preferable that the entirety of the thigh side support section 12 and the shin side support section 14 satisfies at least one of the relationship: elongation ratio in axial direction>elongation ratio in circumferential direction, or condition of an elongation ratio in axial direction of 150% or higher.

Furthermore, in regard to the supporter body 100, it is preferable that when an elongation ratio in the circumferential direction is measured by a tensile test under conditions of a grip width of 15 mm, a distance between grippers of 15 mm, and a tensile load of 20 N, for each of: a measurement area X1 (measurement area X1 is not shown in the diagram) centering on a position X, which corresponds to the center of a kneecap in the knee support section 10; a measurement area T1 (measurement area T1 is not shown in the diagram) centering on a position T, which is the center in the axial direction of the thigh side support section 12 on an extension line 30 extending in the axial direction from a position Y corresponding to the center of a popliteal part; and a measurement area S1 (measurement area S1 is not shown in the diagram) centering on position S, which is the center in the axial direction of the shin side support section on the extension line 30 extending in the axial direction from the position Y corresponding to the center of the popliteal part, an elongation ratio in the circumferential direction of the measurement area X1 is lower than an elongation ratio in the circumferential direction of the measurement area T1 and is lower than an elongation ratio in the circumferential direction of the measurement area S1. Thereby, the relationship: average wear pressure A>average wear pressure B can be satisfied more easily.

In regard to the supporter body 100, it is preferable that when the elongation ratio in the axial direction is measured by a tensile test under conditions described above for each of a measurement area X1, a measurement area T1, and a measurement area S1, an elongation ratio in the axial direction of the measurement area X1 is lower than an elongation ratio in the axial direction of the measurement area T1 and is lower than an elongation ratio in the axial direction of the measurement area S1. Thereby, the relationship: average wear pressure A>average wear pressure B can be satisfied more easily.

Furthermore, the supporter body 100 (preferably, at least one of the thigh side support section 12 or the shin side support section 14) may include a concave-convex structure region according to the fourth embodiment that will be described below. In regard to a preferred embodiment of the concave-convex structure region in a case in which the supporter body 100 includes a concave-convex structure region, the fourth embodiment may be referred to.

Third Embodiment

The knee supporter according to the present third embodiment includes a tubular supporter body, the tubular support body including a knee support section that is worn on a part of the leg including a knee and supports the knee, a thigh side support section that supports a thigh side with respect to the knee of the leg, and a shin side support section that supports a shin side with respect to the knee of the leg, in which an average wear pressure A of the knee support section and an average wear pressure B of the thigh side support section and the shin side support section satisfy the relationship: average wear pressure A>average wear pressure B, and when the knee support section is stretched with a force of 5 kg in a direction in which a distance will increase between a position X, which corresponds to a center of the kneecap in the knee support section, and a position Y, which corresponds to a center of a popliteal part in the knee support section, an elongation percentage of the knee support section is from 180% to 280%.

When the elongation percentage of the knee support section is 180% or higher, as a bodily sensation of the wearer, bending and stretching of the knee joint can be performed easily.

When the elongation percentage of the knee support section is 280% or lower, as a bodily sensation of the wearer, a superior feeling of support for the knee is maintained.

The knee supporter of the third embodiment is a knee supporter similar to the knee supporter of the first embodiment or the second embodiment, except that the elongation percentage of the knee support section is limited to be from 180% to 280%, the knee supporter is not limited by the condition that the "relationship: elongation ratio in axial direction>elongation ratio in circumferential direction" described above is satisfied, and the knee supporter is not limited by the condition that the elongation ratio in axial direction is 150% or higher".

A preferred configuration of the knee supporter of the third embodiment is also similar to the preferred configurations of the knee supporter of the first embodiment or the second embodiment.

The method of measuring the elongation percentage and preferred ranges for the knee support section described above are also as explained in the sections for the first embodiment and the second embodiment.

In regard to the knee supporter of the third embodiment, it is preferable that when an elongation ratio in a circumferential direction is measured by a tensile test under conditions of a grip width of 15 mm, a distance between grippers of 15 mm, and a tensile load of 20 N, at each of three points in total, the three points being: the position X; the position Y; and an intermediate position between the position X and the position Y, the three measured values are all included in a range of from 100% to 250%, and a difference between a maximum value and a minimum value among the three measured values is from 0% to 80%. The method of measuring the elongation ratio in the circumferential direction is as explained in the sections for the first embodiment and the second embodiment.

Thereby, a balance is more effectively achieved between the ease of bending and stretching of the knee joint, and a superior feeling of support for the knee.

Fourth Embodiment

A garment according to the fourth embodiment is a garment including a tubular joint supporter section, the tubular joint supporter section including, a central region in an axial direction of the tubular joint supporter section, the central region including a wear pressure applying region for applying wear pressure to a joint site of a body, a one-end side region positioned at one end side in the axial direction with respect to the central region, and an other-end side region positioned at another end side in the axial direction with respect to the central region, in which the wear pressure of the wear pressure applying region is higher than an average wear pressure of the one-end side region and the other-end side region, and regions other than the wear pressure applying region in the tubular joint supporter section include a concave-convex structure region formed from a concave-convex structure.

According to the fourth embodiment, a joint area of the body refers to an area positioned on the outer side of a joint when the joint is bent, and the term refers to an area that covers at least a portion or the entirety of tendons and ligaments.

According to the garment including a tubular joint supporter section (hereinafter, also referred to as "supporter section") of the fourth embodiment, the wear pressure applying region of the supporter section is worn on a joint area. As bodily sensations of the wearer who wears this garment, an excellent feeling of support and excellent fitting comfort can be obtained at the joint area that is in contact with the wear pressure applying region.

The reason for this is not clearly understood; however, it is speculated to be because, since the wear pressure of the wear pressure applying region is higher than the average wear pressure of the one-end side region and the other-end side region, a sensation as if the joint area supported by the wear pressure applying region is supported at a higher wear pressure than the actual wear pressure of the wear pressure applying region, due to sensory illusion. Furthermore, (a portion of) the supporter section can be adhered to an area of the joint by providing a wear pressure difference in the wear pressures between the wear pressure applying region and the one-end side region as well as the other-end side region, and thus fitting comfort can be enhanced.

Generally, as the wear pressure of the supporter section is higher, the stress on the skin tends to become stronger. Here, the stress on the skin refers to intrinsic stress and extrinsic stress exerted on the skin.

In a case in which a wear pressure is applied to the entirety of the supporter section, the wear pressure that is applied becomes an extrinsic stimulus, and the wearer feels stress on the skin in the entire region wearing the supporter section. Therefore, particularly, in the case of wearing the supporter for a long time period, alleviation of stress on the skin is requested. However, when the wear pressure applying region is disposed only in a portion of the supporter section, the stress on the skin in the regions having low average wear pressures (for example, the one-end side region and the other-end side region) is alleviated.

The supporter section in the garment of the fourth embodiment may include a concave-convex structure region formed from a concave-convex structure, in regions other than the wear pressure applying region. Thereby, stress on the skin is alleviated. The effect of alleviating the stress on the skin is considered as an effect attributed to the softness (for example, softness in the thickness direction) of the concave-convex structure. Particularly, the periphery of the joint area (part to which the regions other than the wear pressure applying region are applied) has a soft skin tissue compared to the joint area, and is sensitive to the stress on the skin. It is effective to apply the concave-convex structure region to at least a portion of this periphery of the joint area, for alleviating the stress on the skin.

As discussed above, when the garment of the fourth embodiment is used, a balance between the enhancement of the feeling of support and fitting comfort and the alleviation of stress on the skin is achieved, while it has been conventionally difficult to achieve a balance therebetween.

According to the fourth embodiment, the wear pressure applying region may be the entirety of the central region, or may be a portion thereof.

In a case in which the wear pressure applying region is a portion of the central region, the size of the wear pressure applying region can be appropriately adjusted according to the region in which it is wished to enhance the feeling of support.

It is preferable that the wear pressure applying region is a region including a region covering at least a portion or the entirety of tendons and ligaments positioned on the outer side of the joint when the joint is bent (joint area).

The length in the circumferential direction of the wear pressure applying region is preferably a length equal to ⅓ or more of the total circumferential length of the central region (more particularly, the total circumferential length of the part including the wear pressure applying region).

The length in the axial direction of the wear pressure applying region is preferably a length equal to ⅓ or more of the length in the axial direction of the central region.

The shape of the wear pressure applying region is not particularly limited as long as the region can cover at least the joint area, and the wear pressure applying region can be designed as appropriate according to the shape of the joint area. Examples of the shape include an approximately circular shape, an approximately elliptical shape, and an approximately rectangular shape. The shape of the boundary lines of the wear pressure applying region is also not particularly limited, and the boundary lines may have a straight line shape, or may have a curved or wavy shape. Furthermore, a hemmed structure may also be provided around the boundary lines.

According to the fourth embodiment, in a case in which the wear pressure applying region is a portion of the central region, it is preferable that the wear pressure applying region has a high elongation ratio in the axial direction, compared to the regions other than the wear pressure applying region within the central region.

According to the fourth embodiment, the concave-convex structure region is a region including a concave-convex structure, which is a structure having a concave-convex shape.

Examples of the concave-convex structure that is included in the concave-convex structure region include a knit fabric structure (hereinafter, also referred to as "knit fabric"), a woven fabric structure (hereinafter, also referred to as "woven fabric"), and a resin sheet (for example, a film). Among these, as the concave-convex structure, it is preferable to use a knit fabric or a woven fabric, and it is more preferable to use a knit fabric. In the concave-convex structure region, a single concave-convex structure may be used, or a combination of a plurality of concave-convex structures may also be used.

Among these, as the concave-convex structure region including a concave-convex structure, a concave-convex knitted fabric region including a concave-convex knitted fabric, a concave-convex woven fabric region including a concave-convex woven fabric, or a concave-convex structure region including a concave-convex knitted fabric and a concave-convex woven fabric is preferred, and a concave-convex knitted fabric region including a concave-convex knitted fabric is more preferred.

Preferred embodiments of the concave-convex structure region including a concave-convex structure (for example, size, disposition in the supporter section, and various physical properties) are similarly to the preferred embodiments of the concave-convex knitted fabric region including the concave-convex knitted fabric that will be described below, and a combination of preferred embodiments can be used as appropriate.

A concave-convex knitted fabric region is a region including a concave-convex knitted fabric, which is a knitted fabric having a concave-convex shape. The concave-convex knitted fabric region may be disposed in the entirety of the regions other than the wear pressure applying region, or may be disposed in a portion thereof. Furthermore, the concave-convex knitted fabric included in the concave-convex knitted fabric region may be a single concave-convex knitted fabric, or may include two or more kinds of concave-convex knitted fabrics.

In a case in which the concave-convex knitted fabric region is disposed in a portion of the regions other than the wear pressure applying region, the size of the concave-convex knitted fabric region is preferably a size to the extent that the concave-convex knitted fabric being in touch with the skin can be felt.

Specifically, regarding the area of the concave-convex knitted fabric region, the area of the concave-convex knitted fabric region in a state of being stretched upon wearing is preferably 4 $cm^2$ or more, and more preferably 6 $cm^2$ or more.

Furthermore, the length in the circumferential direction of the concave-convex knitted fabric region is preferably a length equal to ⅙ or more, and more preferably a length equal to ⅓ or more, of the total circumferential length of the supporter section (more particularly, length of the whole circumference that traverses the concave-convex knitted fabric region).

Here, the length in the circumferential direction of the concave-convex knitted fabric region means, in a case in which the concave-convex knitted fabric region is disposed dividedly in the circumferential direction, the total length in the circumferential direction in the case of gathering the concave-convex knitted fabric regions without overlapping in the circumferential direction.

The concave-convex knitted fabric region may be such that a plurality of such regions is disposed in the regions other than the wear pressure applying region. In a case in which a plurality of concave-convex knitted fabric regions is disposed in the regions other than the wear pressure applying region, the disposition thereof is not particularly limited.

The shape of the concave-convex knitted fabric region and the shape of the boundary lines between the concave-convex knitted fabric region and the adjacent regions are not particularly limited. These can be designed as appropriate, from the viewpoint of design characteristics.

According to the fourth embodiment, the supporter section includes a wear pressure applying region and a concave-convex fabric region (for example, concave-convex knitted fabric region). The supporter section may also include a region other than the wear pressure applying region and the concave-convex fabric region (another region).

In a case in which another region is included in addition to the wear pressure applying region and the concave-convex fabric region, the other region can be constructed from a woven fabric, a resin sheet, a knitted fabric different from the wear pressure applying region and the concave-convex fabric region, or the like. Above all, from the viewpoint of alleviating stress on the skin, a knitted fabric or a woven fabric is preferred, and a knitted fabric using elastic yarn is more preferred. However, the fabric of the other region is selected as appropriate such that the average wear pressure in the one-end side region and the other-end side region is lower than the wear pressure of the wear pressure applying region.

The garment of the fourth embodiment may be a garment composed only of a joint supporter section (that is, a supporter), or may be a garment including a joint supporter section as a portion of the garment.

Here, examples of the garment including a joint supporter section as a portion of the garment include bottoms (for example, bottoms for sport applications or innerwear) such as spats, tights (for example, sport tights, compression tights, or medical tights), girdles, panty hoses, leggings, stirrup pants, and leg warmers; tops such as underwear, shirts, and compression shirts; socks; gloves; fingerstalls; and bandages.

Examples of the joint for the joint area include a knee joint, an elbow joint, a metacarpal phalangeal joint, an interphalangeal joint, a proximal interphalangeal joint, a distal interphalangeal joint, a wrist joint, a talocrural joint, a subtalar joint, a neck joint, a shoulder joint, and a hip joint.

The joint on which the central region of the supporter section is worn is preferably a knee joint, an elbow joint, or a wrist joint, and more preferably a knee joint, from the viewpoint of alleviating pain. The articular knee joint, elbow joint, and wrist joint have a common feature that the joint is composed of three or more bones.

When a joint area is compressed by applying a wear pressure by the wear pressure applying region, the disposition of bones at the joint is optimized, and areas other than the joint area, which are positioned around the joint, can be controlled to move easily. This gives an effect of alleviating pain.

The articular knee joint, elbow joint, and wrist joint are joints having wider ranges of movability compared to other joints. Since these articular knee joint, elbow joint, and wrist joint are subject to easy destruction of the disposition of bones as a result of weakening of the muscles, it is particularly useful to impart a feeling of support by wearing a supporter on these joints.

Particularly, since the knee joint supports the weight of the human body during walking, the knee joint is likely to be subjected to a large burden, and the disposition of bones is likely to be destroyed. Therefore, the effects of the fourth embodiment are particularly effectively provided in a case in which the central region of the supporter section is worn on the knee joint.

In regard to the garment of the fourth embodiment, it is preferable that elongation ratios of the wear pressure applying region and the concave-convex knitted fabric region in the axial direction measured by a tensile test under conditions of a grip width of 15 mm, a distance between grippers of 15 mm, and a tensile load of 20 N, satisfy the relationship: elongation ratio of concave-convex knitted fabric region>elongation ratio of wear pressure applying region. Thereby, the movement conformity is further enhanced.

It is considered that this effect of enhancing the movement conformity is an effect attributed to the fact that slippage upon wearing of the supporter section is prevented by applying a wear pressure to the wear pressure applying region and thereby closely adhering the supporter section to the joint area, and to the fact that the concave-convex knitted fabric region undergoes expansion and contraction more easily compared to the wear pressure applying region.

Generally, during the movement of bending and stretching of a joint, the shape of the skin that is positioned above and below the joint changes along with the movement of the muscles, and due to the change of the shape, twisting or sagging caused by the supporter section occurs. The wearer feels stress on the skin due to the poor feeling of wearing attributed to twisting or sagging of the supporter section.

However, in the garment of the fourth embodiment, since the supporter section includes a wear pressure applying region, the supporter section can be stably worn on the joint site, and slippage upon wearing of the supporter section can be prevented.

Furthermore, in the garment of the fourth embodiment, deformation strain of the supporter section resulting from a change in the shape of the skin can be reduced by making the elasticity in the axial direction of the concave-convex knitted fabric region included in the regions other than the wear pressure applying region, higher than the elasticity in the axial direction of the wear pressure applying region. As a result, twisting or sagging of the supporter section is ameliorated, and the stress on the skin can be reduced. Particularly, in a case in which big movements such as bending and stretching of joints are performed, excellent effects are provided.

The elongation ratio according to the fourth embodiment is measured similarly to the elongation ratio according to the first embodiment.

It is preferable that the concave-convex knitted fabric in the concave-convex knitted fabric region includes a float knitted structure. The float knitted structure in a concave-convex knitted fabric can easily undergo expansion and contraction compared to knitted fabrics other than the float knitted structure. The reason why a concave-convex knitted fabric including a float knitted structure is soft is considered that even in a case in which the concave-convex knitted fabric region expands during wearing, there remains room for expansion (that is, concavities and convexities) in the float knitted structure in the concave-convex knitted fabric. When this room for expansion is brought into contact with the skin, the concave-convex knitted structure gives a soft feel to touch. Also, from the viewpoint of ease of production of the concave-convex knitted fabric, it is preferable to form the concave-convex knitted fabric by disposing a float knitted structure. Regarding the knitted structure that serves as a base of the concave-convex knitted fabric, the knitted structure according to the first embodiment can be used, and an embodiment of including a float knitted structure into such a knitted structure is a preferred embodiment.

Furthermore, it is preferable that the concave-convex knitted fabric in the concave-convex knitted fabric region is knitted with elastic yarn, and it is more preferable that the concave-convex knitted fabric is a concave-convex knitted fabric including a float knitted structure using elastic yarn. By using elastic yarn, the concave-convex knitted fabric can be made softer.

Examples of the elastic yarn include a polyurethane, a polyolefin-based elastomer, natural rubber, and a silicone. Among these, from the viewpoint of having superior elasticity, a polyurethane, a polyolefin-based elastomer, and natural rubber are preferred. Here, a preferred material for the elastic yarn has the same meaning as the preferred material according to the first embodiment. Furthermore, the yarn according to the first embodiment can also be used as the elastic yarn.

From the viewpoint of having excellent production suitability when the supporter section is integrally produced by circular knitting, it is preferable to dispose a float knitted structure in the axial direction.

Furthermore, it is preferable that the concave-convex knitted fabric region has long-shaped concavities.

It is needless to say that the long shape as used herein is the shape of a concavity in a planar view.

In the concave-convex knitted fabric region, particularly the bottom parts of concavities have a property of being easily stretchable. Accordingly, a concave-convex knitted fabric region having long-shaped concavities has a property of being easily stretchable in the width direction of these concavities. Therefore, when the concave-convex knitted fabric region has long-shaped concavities, the entire concave-convex knitted fabric region can be easily stretched, the movement conformity is further enhanced.

It is preferable that the concave-convex knitted fabric region has a plurality of long-shaped concavities.

It is preferable that the concave-convex knitted fabric region has a plurality of long-shaped concavities, and for each of this plurality of concavities, the length direction is approximately parallel to the circumferential direction of the tubular supporter section.

In this case, the width direction of the long-shaped concavity corresponds to the axial direction of the supporter section. Accordingly, the concave-convex knitted fabric region can be easily stretched in the axial direction of the supporter section, and therefore, the movement conformity is further enhanced.

Furthermore, it is advantageous that the concave-convex knitted fabric region has a plurality of long-shaped concavities having the length direction described above, from the viewpoint of having excellent production suitability at the time of producing the supporter section by circular knitting. More particularly, when the supporter section is produced by circular knitting, the long-shaped concavities described above (that is, long-shaped concavities whose length direction is approximately parallel to the circumferential direction of the supporter section) can be easily produced by knitting by skipping one or more stitches in the circumferential direction by float knitting.

The concave-convex knitted fabric region is preferably such that when the concave-convex knitted fabric region is stretched at an elongation ratio of 200% in one of an axial direction or a circumferential direction of the tubular supporter section, the elastic modulus in the one of the axial direction or the circumferential direction is less than 0.1 $N/mm^2$.

When the elastic modulus in the one direction is less than 0.1 $N/mm^2$, the concave-convex knitted fabric region has superior softness, and as a result, the stress on the skin is further alleviated.

Here, the elastic modulus is an index representing the difficulty of deformation, and is a constant of proportionality between the stress and strain in elastic deformation. The value of the elastic modulus can be obtained by the measurement method described below. When the value of the elastic modulus is small, it means that in a case in which the concave-convex knitted fabric region is stretched at the time of wearing, the stress at which the concave-convex knitted fabric tends to return to the shape before stretching is small. Thus, it can be said that the burden on the skin is small.

From the viewpoint of having excellent production suitability when the supporter section is produced by circular knitting, it is preferable that the elastic modulus in the axial direction is less than 0.1 $N/mm^2$.

The concave-convex knitted fabric region is preferably such that when the concave-convex knitted fabric region is stretched at an elongation ratio of 200% in one of an axial direction or a circumferential direction of the tubular supporter section, the elastic modulus in the one of the axial direction or the circumferential direction is less than 0.1 $N/mm^2$, and when the concave-convex knitted fabric region is stretched at an elongation ratio of 200% in the other of the axial direction or the circumferential direction of the tubular supporter section, the elastic modulus in the other of the axial direction or the circumferential direction is from 0.1 $N/mm^2$ to 0.5 $N/mm^2$.

The stress on the skin can be reduced by setting the value of the elastic modulus in the above-described one direction to be less than 0.1 $N/mm^2$. Then, when the elastic modulus of the other direction is 0.1 $N/mm^2$ or more, fitting comfort is further enhanced. Furthermore, when the elastic modulus of the other direction is 0.1 $N/mm^2$ or more, slippage upon wearing of the supporter section can be suppressed. Furthermore, when the elastic modulus of the other direction is 0.5 $N/mm^2$ or less, stress on the skin can be further reduced.

A knitted fabric having an elastic modulus in the axial direction and an elastic modulus in the circumferential direction that are different from each other can be produced by appropriately adjusting the number of skipping stitches in the float knitting.

According to the present specification, the elastic modulus in the axial direction means a value measured in an area having a measurement width (that is, length in the circumferential direction) of 15 mm, in which the measurement center is at a central position (that is, a position that is at the center in the circumferential direction and at the center in the axial direction) of the region as an object of measurement (for example, concave-convex knitted fabric region).

According to the present specification, the elastic modulus in the axial direction is measured by a tensile test under the conditions of a grip width of 15 mm, a distance between grippers of 15 mm, and a tensile load of 20 N. Here, the direction of the tensile load is the axial direction of the supporter section.

In regard to the measurement of the elastic modulus in the axial direction, a portion of the concave-convex knitted fabric region is fixed to a tensile testing machine at a grip width of 15 mm and a distance between grippers of 15 mm, and the knitted fabric region is stretched by pulling at a tensile rate of 15 mm/min. The elastic modulus at a time point of having the knitted fabric region stretched 200% is read, and the value is designated as the measured value.

The tensile test may also be carried out, in a case in which it is difficult to perform the test for a portion of the concave-convex knitted fabric region, by cutting out a specimen that measures 30 mm on each side from the concave-convex knitted fabric region, and performing the test using the cut specimen. Furthermore, the tensile test may also be carried out by producing a specimen that measures 30 mm on each side from a concave-convex knitted fabric having the same knitting as the concave-convex knitted fabric region, and performing the test using the specimen thus produced.

The number of times of performing the test is set to 5 times, an average value is determined from three measured values remaining after excluding the maximum value and the minimum value from the measured values obtained in 5 times, and this average value is employed as the "elastic modulus in the axial direction when stretched 200% in the axial direction".

Regarding the apparatus for the tensile test, any general tensile testing machine can be used; however, for example, an autograph "AGS-X 1 kN" manufactured by Shimadzu Corp. can be used.

According to the present specification, the elastic modulus in the circumferential direction means a value measured in the same manner as in the case of the elastic modulus in the axial direction, except that the direction of the tensile load is set to the circumferential direction of the supporter section.

The bending and stretching movement of a joint extends the skin around the joint. Thus, when a knitted fabric having high elasticity in the direction of extension of the skin around the joint is used, the movement conformity is further enhanced.

For example, in a case in which the extent of extension of the skin around the joint is larger in the axial direction than in the circumferential direction, it is preferable that the concave-convex knitted fabric region satisfies the relationship: elongation ratio in axial direction>elongation ratio in circumferential direction.

Meanwhile, in a case in which the extent of extension of the skin around the joint is larger in the circumferential direction than in the axial direction, it is preferable that the concave-convex knitted fabric region satisfies the relationship: elongation ratio in circumferential direction>elongation ratio in axial direction.

Here, the elongation ratio in axial direction and the elongation ratio in circumferential direction are each an elongation ratio measured by a tensile test under conditions of a grip width of 15 mm, a distance between grippers of 15 mm, and a tensile load of 20 N.

The preferred range of the ratio [elongation ratio in the axial direction/elongation ratio in the circumferential direction] of the concave-convex knitted fabric region according to the fourth embodiment is similar to the preferred range of the ratio [elongation ratio in the axial direction/elongation ratio in the circumferential direction] of the region R according to the first embodiment.

The preferred range of the elongation ratio in the axial direction of the concave-convex knitted fabric region according to the fourth embodiment is similar to the preferred range of the elongation ratio in the axial direction of the region R according to the first embodiment.

In regard to the garment of the fourth embodiment, from the viewpoint of further reducing stress on the skin, it is preferable that at least one of the one-end side region or the other-end side region includes a concave-convex knitted fabric region; it is more preferable that the one-end side region and the other-end side region (that is, both of them) include a concave-convex knitted fabric region; and it is particularly preferable that the one-end side region and the other end-side region include a concave-convex knitted fabric region on the same semicircular side.

Even more preferably, at least one of the back face side of the one-end side region or the back face side of the other-end side region in the tubular supporter section includes a concave-convex knitted fabric region, and still more preferably, the back face side of the one-end side region and the back face side of the other-end side region respectively include a concave-convex knitted fabric region.

Here, the front face side refers to the semicircular side centering on a center XX of the wear pressure applying region in the tubular supporter section (outer side of a joint supporter when a joint is bent and stretched; in the case of a knee supporter, the kneecap side), and the back face side refers to the other semicircular side in the tubular supporter section (inner side of a joint supporter when a joint is bent and stretched; in the case of a knee supporter, the kneecap side). Hereinafter, the same applies throughout.

In regard to the garment of the fourth embodiment, a configuration in which at least one of the one-end side region or the other-end side region (preferably, both) includes a concave-convex knitted fabric region and a region having a higher elastic modulus in the axial direction than the concave-convex knitted fabric region (hereinafter, also referred to as "region M"), and the concave-convex knitted fabric region and the region M are disposed in the circumferential direction, is preferred.

Thereby, a balance is achieved between a reduction of stress on the skin by the concave-convex knitted fabric region and an enhancement of the feeling of stability upon wearing (more particularly, an increase in the wear pressure to a certain extent) caused by the region M, in at least one (preferably, both) of the one-end side region or the other-end side region.

It is more preferable from the viewpoint of reducing stress on the skin that the concave-convex knitted fabric region and the region M are both formed from knitted fabrics produced by knitting elastic yarn.

In regard to the tubular supporter section, an embodiment in which the concave-convex knitted fabric region is on the back face side, while the region M is on the front face side, is a preferred embodiment. In at least one of the regions on the back face side of the one-end side region or the back face side of the other-end side region, the extent of extension and contraction of the skin caused by bending and stretching of the joint is larger compared to the respective front face sides (not including the joint site). Therefore, applying a concave-convex knitted fabric region including a concave-convex knitted fabric, which is a knitted fabric having higher stretchability, to the back face side is effective for ameliorating slippage upon wearing. Also, when the region M is disposed at the respective front face sides, the feeling of stability during wearing can be effectively enhanced.

Also in regard to the above-described configuration in which at least one of the one-end side region or the other-end side region includes a concave-convex knitted fabric region and the region M, preferred configurations with regard to the area, the length in the circumferential direction, disposition, and shape of the concave-convex knitted fabric region can be applied.

From the viewpoint of imparting a feeling of stability during wearing, it is more preferable that the length in the circumferential direction of the region M is a length equal to ⅓ or more of the total circumferential length of the supporter section (more particularly, the total circumferential length that traverses the region M).

Here, the length in the circumferential direction of the region M means, in a case in which the region M is disposed dividedly along the circumferential direction, the total length in the circumferential direction in the case of gathering the divisions of the region M without overlapping in the circumferential direction.

Furthermore, it is preferable that the length in the axial direction of the region M occupies ⅓ or more of the region of the length in the axial direction of the one-end side region and the other-end side region.

Here, the length in the axial direction of the region M means, in a case in which the region M is disposed dividedly along the axial direction, the total length in the axial direction in the case of gathering the divisions of the region M without overlapping in the axial direction.

Regarding the region M, a plurality of regions may be disposed in at least one of the one-end side region or the other-end side region. In a case in which a plurality of regions M is disposed in at least one of the above-described regions, the disposition is not particularly limited. The shape of the region M, and the shape of the boundary lines between the region M and the adjacent regions are not particularly limited.

In the above-described configuration in which at least one of the one-end side region or the other-end side region includes a concave-convex knitted fabric region and a region M, the supporter section includes a wear pressure applying region, the concave-convex knitted fabric region, and the region M. In regard to this configuration, the supporter section may include a region other than the wear pressure applying region, the concave-convex knitted fabric region, and the region M (another region).

In a case in which the supporter section includes another region in addition to the wear pressure applying region, the concave-convex knitted fabric region, and the region M, the other region can be constructed from a woven fabric; a resin sheet; a knitted fabric different from the knitted fabrics of the wear pressure applying region, the concave-convex knitted fabric region, and the region M; or the like.

Among them, from the viewpoint of reducing stress on the skin, a knitted fabric or a woven fabric is preferred, and a knitted fabric obtained by using elastic yarn is more preferred. However, the fabric of the other region is selected as appropriate such that the average wear pressure in the one-end side region and the other-end side region is lower than the wear pressure of the wear pressure applying region.

In the fourth embodiment, from the viewpoint of further reducing stress on the skin, the embodiments listed below are also preferable.

In a case in which the extent of extension of the skin around the joint is larger in the axial direction than in the circumferential direction, and in which the back face side of the one-end side region includes the concave-convex knitted fabric region, it is preferable that elongation ratios in the axial direction satisfy the relationship: elongation ratio of concave-convex knitted fabric region at the back face side of the one-end side region>elongation ratio of front face side of the one-end side region.

In a case in which the extent of extension of the skin around the joint is larger in the axial direction than in the circumferential direction, and in which the back face side of the other-end side region includes the concave-convex knitted fabric region, it is preferable that elongation ratios in the axial direction satisfy the relationship: elongation ratio of concave-convex knitted fabric region on the back face side of the other-end side region>elongation ratio of front face side of the other-end side region.

In a case in which the extent of extension of the skin around the joint is larger in the axial direction than in the circumferential direction, and in which the back face side of the one-end side region and the back face side of the other-end side region include the concave-convex knitted fabric region, it is preferable that elongation ratios in the axial direction satisfy the relationship: elongation ratio of concave-convex knitted fabric region at the back face side of the one-end side region>elongation ratio of front face side of the one-end side region, and that elongation ratios in the axial direction satisfy the relationship: elongation ratio of concave-convex knitted fabric region on the back face side of the other-end side region>elongation ratio of front face side of the other-end side region.

In a case in which the extent of extension of the skin around the joint is larger in the circumferential direction than in the axial direction, and in which the back face side of the one-end side region includes the concave-convex knitted fabric region, it is preferable that elongation ratios in the circumferential direction satisfy the relationship: elongation ratio of concave-convex knitted fabric region at the back face side of the one-end side region>elongation ratio of front face side of the one-end side region.

Furthermore, in a case in which the extent of extension of the skin around the joint is larger in the circumferential direction than in the axial direction, and in which the back face side of the other-end side region includes the concave-convex knitted fabric region, it is preferable that elongation ratios in the circumferential direction satisfy the relationship: elongation ratio of concave-convex knitted fabric region on the back face side of the other-end side region>elongation ratio of front face side of the other-end side region.

In a case in which the extent of extension of the skin around the joint is larger in the circumferential direction than in the axial direction, and in which the back face side of the one-end side region and the back face side of the other-end side region include the concave-convex knitted fabric region, it is preferable that elongation ratios in the circumferential direction satisfy the relationship: elongation ratio of concave-convex knitted fabric region at the back face side of the one-end side region>elongation ratio of front face side of the one-end side region, and that elongation ratios in the circumferential direction satisfy the relationship: elongation ratio of concave-convex knitted fabric region on the back face side of the other-end side region>elongation ratio of front face side of the other-end side region.

The preferred embodiments can be applied as appropriate depending on the type of the joint.

Here, the elongation ratio in the axial direction and the elongation ratio in the circumferential direction are each an elongation ratio measured by a tensile test under conditions of a grip width of 15 mm, a distance between grippers of 15 mm, and a tensile load of 20 N.

Preferred configurations of the support sections in the garment of the fourth embodiment are similar to the preferred configurations of the knee supporter according to the first embodiment.

The one-end side region, the central region, and the other-end side region according to the fourth embodiment correspond to the thigh side support section, the knee support section, and the shin side support section, respectively, according to the first embodiment.

Furthermore, the front face side according to the fourth embodiment corresponds to the kneecap side according to the first embodiment, and the back face side according to the fourth embodiment corresponds to the popliteal side according to the first embodiment.

For example, in a case in which the central region according to the fourth embodiment is worn on the knee joint (that is, in a case in which the supporter section according to the fourth embodiment is a knee supporter), from the viewpoint of further enhancing the feeling of support and fitting comfort, it is preferable that an average wear pressure XA of the central region and an average wear pressure XB of the one-end side region and the other-end side region satisfy the relationship: average wear pressure XA>average wear pressure XB; it is more preferable that the relationship: average wear pressure XA−average wear pressure XB≥0.8 kPa is satisfied; and it is particularly preferable that the relationship: average wear pressure XA—average wear pressure XB≥1.0 kPa is satisfied.

According to the fourth embodiment, from the viewpoint of further enhancing the feeling of support and fitting comfort, it is preferable that an average wear pressure XA of the central region and an average wear pressure XB1 of the one-end side region satisfy the relationship: average wear pressure XA>average wear pressure XB1; it is more preferable that the relationship: average wear pressure XA−average wear pressure XB1≥0.8 kPa is satisfied; and it is particularly preferable that the relationship: average wear pressure XA−average wear pressure XB1≥1.0 kPa is satisfied.

Furthermore, according to the fourth embodiment, from the viewpoint of further enhancing the feeling of support and fitting comfort, it is preferable that an average wear pressure XA of the central region and an average wear pressure XB2 of the other-end side region satisfy the relationship: average wear pressure XA>average wear pressure XB2; it is more preferable that the relationship: average wear pressure XA−average wear pressure XB2≥0.8 kPa is satisfied; and it is particularly preferable that the relationship: average wear pressure XA−average wear pressure XB2≥1.0 kPa is satisfied.

Preferred ranges of the average wear pressure XA, the average wear pressure XB, the average wear pressure XB1, and the average wear pressure XB2 are similar to the preferred ranges of the average wear pressure A, the average wear pressure B, the average wear pressure B1, and the average wear pressure B2, respectively, according to the first embodiment.

Furthermore, according to the fourth embodiment, from the viewpoint of further enhancing the movement conformity, it is preferable that the elongation ratio in the axial direction of the concave-convex knitted fabric region is 150% or higher.

It is preferable that when the central region is stretched with a force of 5 kg in a direction in which a distance will increase between the center XX of the wear pressure applying region and a center XY at a back face side of the central region, an elongation percentage of the central region is from 180% to 280%.

When the elongation percentage of the central region is 180% or higher, as a bodily sensation of the wearer, bending and stretching of the joint can be easily performed.

When the elongation percentage of the central region is 280% or lower, as a bodily sensation of the wearer, a high feeling of support is maintained.

The elongation percentage is as explained in regard to the first embodiment. A more preferred range of the elongation percentage of the central region according to the fourth embodiment is similar to the preferred range of the elongation percentage of the knee support section according to the first embodiment.

Furthermore, when an elongation ratio in the circumferential direction is measured by a tensile test under conditions of a grip width of 15 mm, a distance between grippers of 15 mm, and a tensile load of 20 N, at each of three points in total, the three points being the center XX of the wear pressure applying region, the center XY at the back face side of the central region, and an intermediate position between the center XX and the center XY, the three measured values are all included in a range of from 100% to 250%, and a difference between a maximum value and a minimum value of the three measured values is from 0% to 80%.

Thereby, a balance is achieved more effectively between the ease of bending and stretching of the joint and the feeling of support.

Furthermore, it is preferable that when an elongation ratio in the circumferential direction is measured by a tensile test under conditions of a grip width of 15 mm, a distance between grippers of 15 mm, and a tensile load of 20 N, for each of: a measurement area XX1 centering on the center XX of the wear pressure applying region; a measurement area XT1 centering on a position XT, which is at the center in the axial direction of the one-end side region on an extension line extending in the axial direction from the center XY at the back face side of the central region; and a measurement area XS1 centering on a position XS, which is at the center in the axial direction of the other-end side region on an extension line extending in the axial direction from the center XY at the back face side of the central region, an elongation ratio in the circumferential direction of the measurement area XX1 is lower than an elongation ratio in the circumferential direction of the measurement area XT1 and is lower than an elongation ratio in the circumferential direction of the measurement area XS1.

Thereby, it becomes easy to satisfy the relationship: average wear pressure XA>average wear pressure XB, and as a result, the feeling of support and fitting comfort are further enhanced.

Furthermore, for each of the measurement area XX1, the measurement area XT1, and the measurement area XS1, it is preferable that when an elongation ratio in the axial direction is measured by a tensile test, an elongation ratio in the axial direction of the measurement area XX1 is lower than an elongation ratio in the axial direction of the measurement area XT1 and is lower than an elongation ratio in the axial direction of the measurement area XS1. Thereby, it becomes easy to satisfy the relationship: average wear pressure XA>average wear pressure XB, and as a result, the feeling of support and fitting comfort are further enhanced.

The shape of the tubular support section may be a tubular shape having at least two openings, and there are no particular limitations other than that.

The shape as viewed in a planar view in a case in which a tubular supporter section is flattened and squashed into an approximately flat shape, may be symmetric or asymmetric about the axial direction, or may be symmetric or asymmetric about the circumferential direction. The shape as viewed in a planar view may be an approximately rectangular shape, or may also be a shape with a portion being curved. The shape of the tubular supporter section can be selected as appropriate according to the shape of the joint to be applied.

The boundary lines of the various regions included in the tubular supporter section may have a straight line shape, or may have a curved or wavy shape. The knitted fabric of the various regions may be integrally knitted, or may not be necessarily knitted integrally.

The tubular supporter section may further have holes or slits in a portion of the knitted fabrics thereof.

It is preferable that the overall structure of the tubular supporter section is a seamless structure. The seamless structure is similar to the matters explained in connection with the first embodiment.

A tubular supporter section having a seamless structure can be formed by continuously producing this supporter section by circular knitting.

Furthermore, it is preferable that the tubular supporter section further includes a one-end side rib cuff section disposed at an opposite side from the central region as viewed from the one-end side region; and an other-end side rib cuff section disposed at an opposite side from the central region as viewed from the other-end side region. Thereby, slippage upon wearing or rolling up of the supporter section is more effectively suppressed.

In a case in which the tubular supporter section includes a one-end side rib cuff section and an other-end side rib cuff section, the one-end side rib cuff section and the other-end side rib cuff section may be connected to the one-end side region and the other-end side region, respectively, by sewing together, and may be continuously produced together with the one-end side region and the other-end side region, respectively, by circular knitting.

From the viewpoint of securing the fitting comfort upon wearing and the elongation ratio described above, it is a preferred embodiment that the one-end side rib cuff section and the other end-side rib cuff section are continuously produced together with the one-end side region and the other end-side region, respectively, by circular knitting.

Also, from a similar point of view, it is a preferred embodiment that the overall structure of the one-end side rib cuff section, the one-end side region, the central region, the other-end side region, and the other-end side rib cuff section is a seamless structure.

It is also acceptable that at least one of the one-end side rib cuff section or the other-end side rib cuff section has a structure that becomes a tubular shape by wrapping around the body. At least one of the one-end side rib cuff section or the other-end side rib cuff section may have, for example, a fastening belt (for example, a hook-and-loop fastener) attached thereto.

It is preferable that at least a portion of the back surface (that is, the surface facing the body; hereinafter, the same) of at least the one-end side rib cuff section is provided with a resin layer (for example, a silicone rubber layer), from the viewpoint of suppressing slippage upon wearing of the supporter section. The resin layer can be formed by, for example, printing. The resin layer may also be provided on the back surface of the other-end side rib cuff section.

Furthermore, the garment of the fourth embodiment may include other members in addition to the supporter section.

Examples of the other members include a rod-shaped supporting member (stay); a fastening belt for fastening a portion of the supporter section to a part of the body, or for enhancing the feeling of support; a pocket; and a tag. These may be disposed separately from the support section of the fourth embodiment, or may be integrally disposed by being sewn to the supporter section or the like. The other members may be disposed at anywhere of the supporter section.

As another member, a resin may be attached to the surface of the knitted fabric of the supporter section. Examples of the method of attaching a resin include spraying, transfer (for example, thermal transfer), resin impregnation, gravure printing, screen printing, rotary printing, thermocompression bonding, and adhesion. The resin is preferably an elastic resin.

Among these, the slippage upon wearing of the supporter section can be more effectively ameliorated by including a fastening belt on the surface of the one-end side rib cuff section (surface on the opposite side from the surface facing the body). It is preferable that the fastening belt includes a member that adjusts the clamping capacity to a part of the body (for example, a hook-and-loop fastener, a buckle, a side release buckle, or a wire adjuster).

The garment of the fourth embodiment may be worn alone, or after a poultice, a bandage or the like is attached, the garment may be worn over the poultice or bandage.

Specific Example of Fourth Embodiment

In the following description, a supporter as a specific example of the garment of the fourth embodiment will be explained with reference to FIG. 9 to FIG. 12; however, the garment of the fourth embodiment is not intended to be limited to this specific example.

Figure 9:
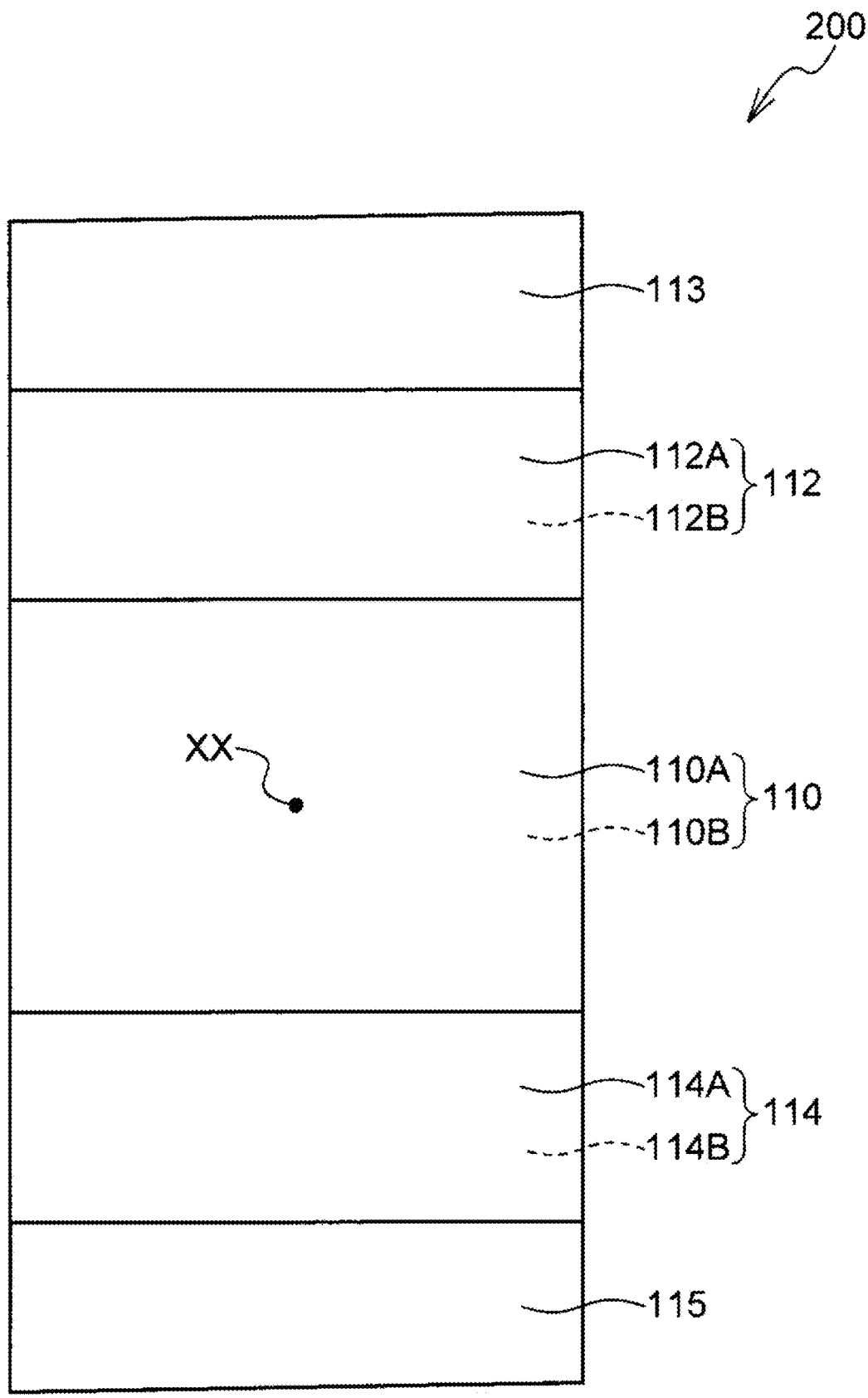
FIG. 9 is a frontal view conceptually illustrating a supporter as a specific example of the garment of the fourth embodiment.
Figure 10:
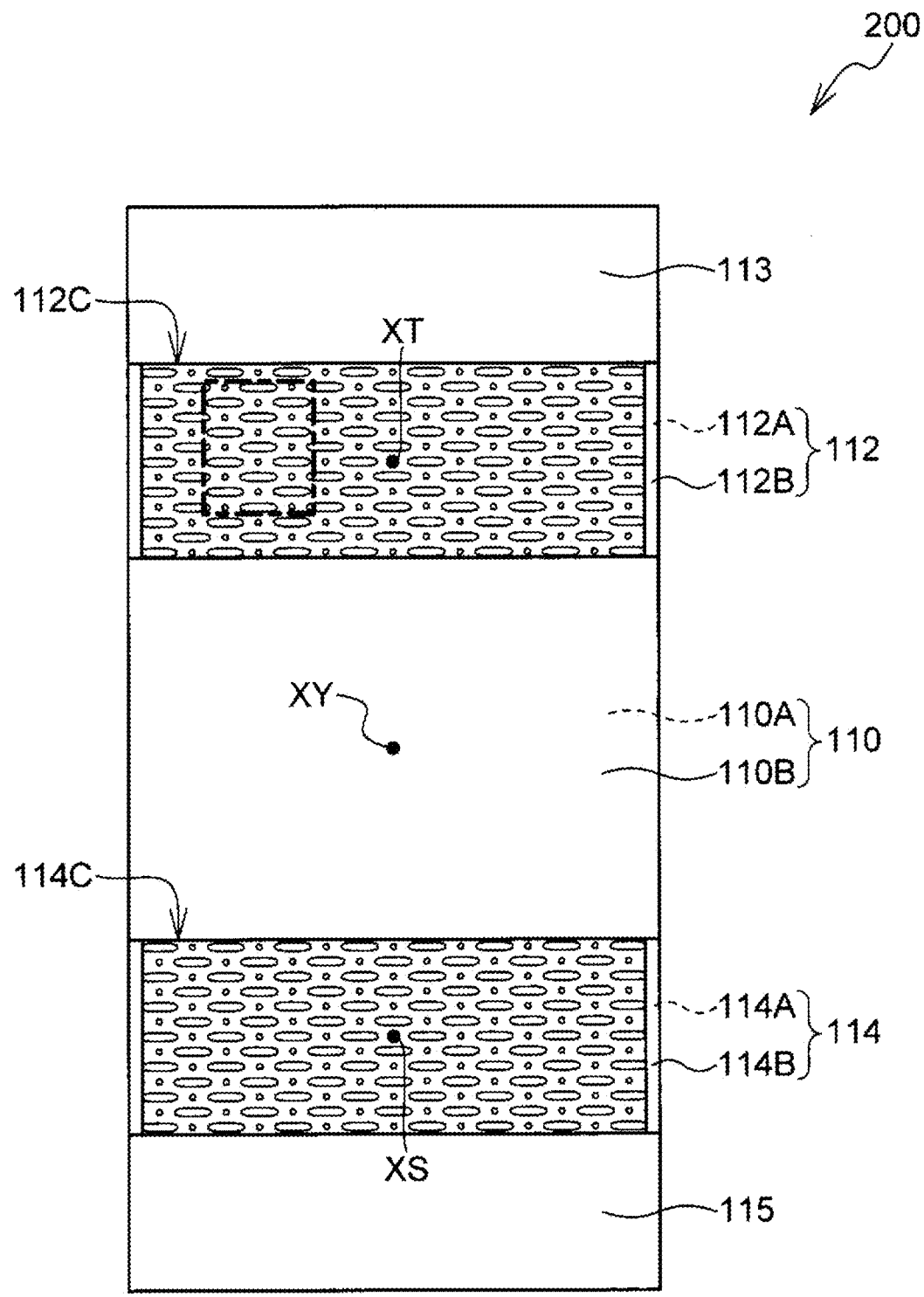
FIG. 10 is a rear view conceptually illustrating a supporter as a specific example of the garment of the fourth embodiment.

FIG. 9 and FIG. 10 are a frontal view (front face view) and a rear view (back face view), respectively, conceptually illustrating a joint supporter (joint supporter having a linear shape), which is a specific example of the garment of the fourth embodiment.

More particularly, FIG. 9 is a frontal view (diagram illustrating the front face side) obtainable by making the shape of the joint supporter into an approximately flat shape by overlapping the front face side and the back face side of the joint supporter as a specific example of the garment of the fourth embodiment, and FIG. 10 is a rear view (diagram illustrating the back face side) in this case.

As illustrated in FIG. 9 and FIG. 10, a joint supporter 200 (tubular joint supporter section) as a specific example of the garment of the fourth embodiment, is configured to include:

a central region 110 in the axial direction of the joint supporter 200;

a one-end side region 112 positioned at the one-end side in the axial direction with respect to the central region 110;

an other-end side region 114 positioned at another end side in the axial direction with respect to the central region 110;

a one-end side rib cuff section 113 disposed at the opposite side from the central region 110 as viewed from the one-end side region 112; and an other-end side rib cuff section 115 disposed at the opposite side from the central region 110 as viewed from the other-end side region 114.

The central region 110 is composed of a front face side 110A of the central region, and a back face side 110B of the central region. In this specific example, the entirety of the front face side 110A of the central region serves as a wear pressure applying region for applying a wear pressure to the joint site.

However, the fourth embodiment is not limited to this example, and only a portion of the front face side 110A of the central region may serve as a wear pressure applying region.

The overall shape of the joint supporter section according to the fourth embodiment as viewed in a planar view in the case of overlapping the front face side and the back face side of the joint supporter section into an approximately flat shape, may be an approximately rectangular shape similarly to the joint supporter 200 illustrated in FIG. 9 and FIG. 10, or may be a curved shape conforming to the shape of the joint. Furthermore, as long as the effects of the fourth embodiment are provided, the knitted fabric may not be integrally knitted, and holes or slits may be provided in a portion of the knitted fabric.

Furthermore, the joint supporter section according to the fourth embodiment may be worn after a poultice, a bandage or the like is attached.

The length in the circumferential direction of the wear pressure applying region according to the fourth embodiment may be any length that covers at least a joint site, and preferably, the length in the circumferential direction is a length equal to ⅓ or more of the total circumferential length of the central region.

The length in the axial direction of the wear pressure applying region according to the fourth embodiment may be any length that covers at least a joint site, and preferably, the length in the axial direction is a length equal to ⅓ or more of the length in the axial direction of the central region.

The wear pressure of the wear pressure applying region is higher than the average wear pressure of the one-end side region 112 and the other-end side region 114. Thereby, the joint supporter 200 has an excellent feeling of support and excellent fitting comfort.

The wear pressure applying region (in this example, the front face side 110A of the central region) is preferably knitted into a knitted fabric composed mainly of a low-stretchable mesh knitted fabric.

In the central region, regions other than the wear pressure applying region may also be knitted into a knitted fabric similar to that of the wear pressure applying region; however, the configuration of the regions other than the wear pressure applying region is not particularly limited.

In the central region, the regions other than the wear pressure applying region can be constructed from a woven fabric, a resin sheet, a knitted fabric different from the wear pressure applying region, or the like. Above all, a knitted fabric or a woven fabric is preferred, and a knitted fabric produced using elastic yarn is more preferred.

In regard to the present specific example, the distinction between the "front face side" and the "back face side" is a distinction made for convenience in order to explain the position in the circumferential direction in the tubular supporter section. Therefore, it is not necessarily essential that the tubular supporter section is physically divided into the front face side and the back face side.

The one-end side region 112 is configured to include a front face side 112A of the one-end side region, and a back face side 112B of the one-end side region.

The other-end side region 114 is configured to include a front face side 114A of the other-end side region, and the back face side 114B of the other-end side region.

As illustrated in FIG. 10, the back face side 112B of the one-end side region is composed of a concave-convex knitted fabric region 112C formed from a concave-convex knitted fabric, except for the two ends in the circumferential direction.

The back face side 114B of the other-end side region is also similarly composed of a concave-convex knitted fabric region 114C formed from a concave-convex knitted fabric, except for the two ends in the circumferential direction.

The entirety of the one-end side region 112 and the other-end side region 114 is knitted using elastic yarn.

The concave-convex knitted fabric of the concave-convex knitted fabric region 112C and the concave-convex knitted fabric of the concave-convex knitted fabric region 114C are knitted by mesh knitting including float knitting using elastic yarn.

In the one-end side region 112, the regions other than the concave-convex knitted fabric region 112C (part of the back face side 112B of the one-end side region, and the front face side 112A of the one-end side region) are regions having a higher elastic modulus in the axial direction than that of the concave-convex knitted fabric region 112C.

In the other-end side region 114, the regions other than the concave-convex knitted fabric region 114C (part of the back face side 114B of the other-end side region, and the front face side 114A of the other-end side region) are regions having a higher elastic modulus in the axial direction than that of the concave-convex knitted fabric region 114C.

The one-end side region 112 and the other-end side region 114 are both examples of an embodiment in which a concave-convex knitted fabric region and the regions having a higher elastic modulus in the axial direction than that of the concave-convex knitted fabric region are disposed in the circumferential direction.

Based on these configurations, a balance is achieved between a reduction of stress on the skin by the concave-convex knitted fabric region and an enhancement of the feeling of stability upon wearing caused by the regions having a higher elastic modulus in the axial direction than that of the concave-convex knitted fabric region, in the one-end side region 112 and the other-end side region 114.

In the one-end side region 112, the regions having a higher elastic modulus in the axial direction than that of the concave-convex knitted fabric region 112C are regions having a lower elongation ratio in the axial direction than that of the concave-convex knitted fabric region 112C.

The other-end side region 114 is configured to have a higher elastic modulus in the axial direction than that of the concave-convex knitted fabric region 114C, and to have a lower elongation ratio in the axial direction than that of the concave-convex knitted fabric region 114C.

Figure 11:
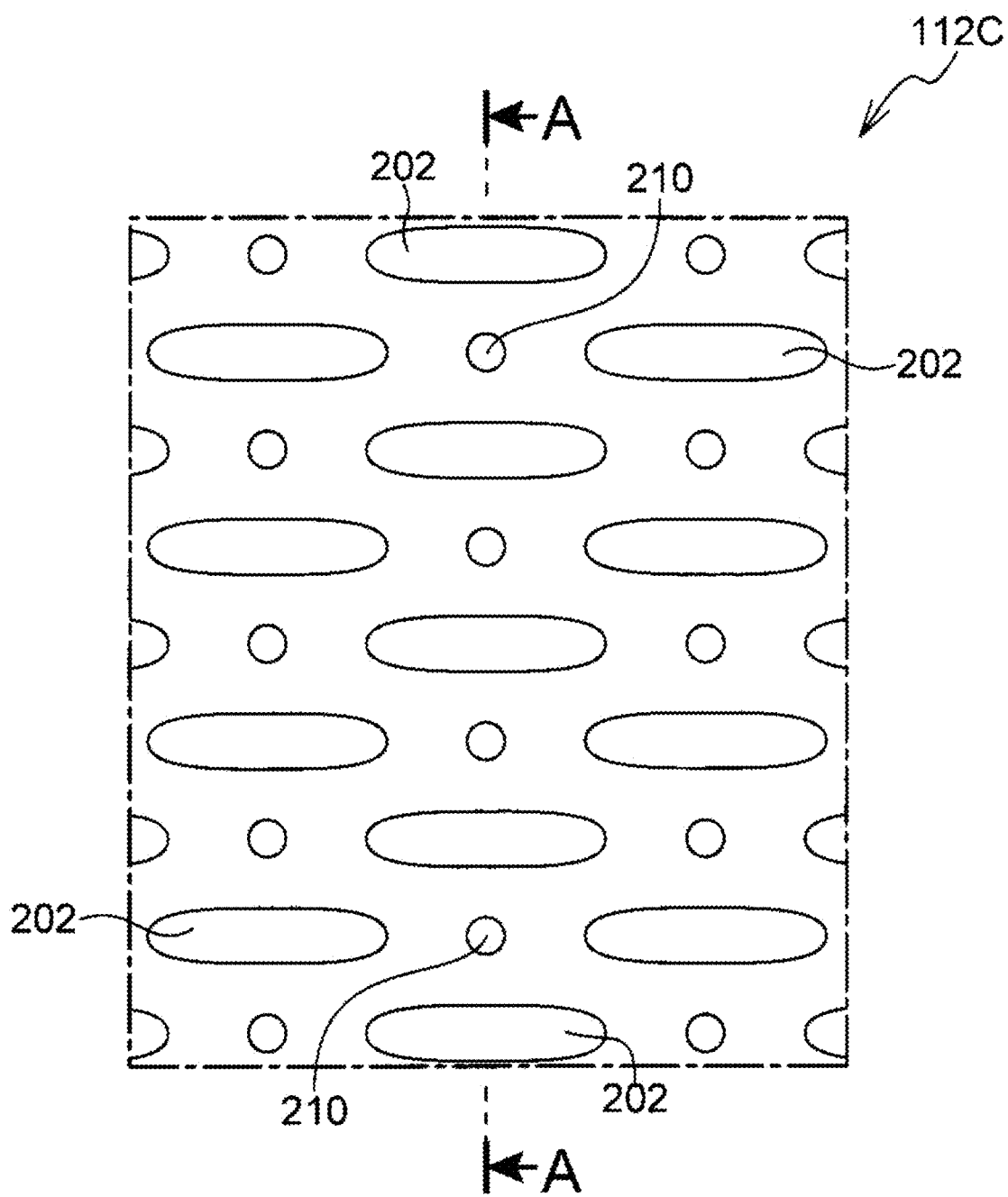
FIG. 11 is a magnified view of the section surrounded by broken lines in FIG. 10 (that is, a magnified view of a concave-convex knitted structure).
Figure 12:
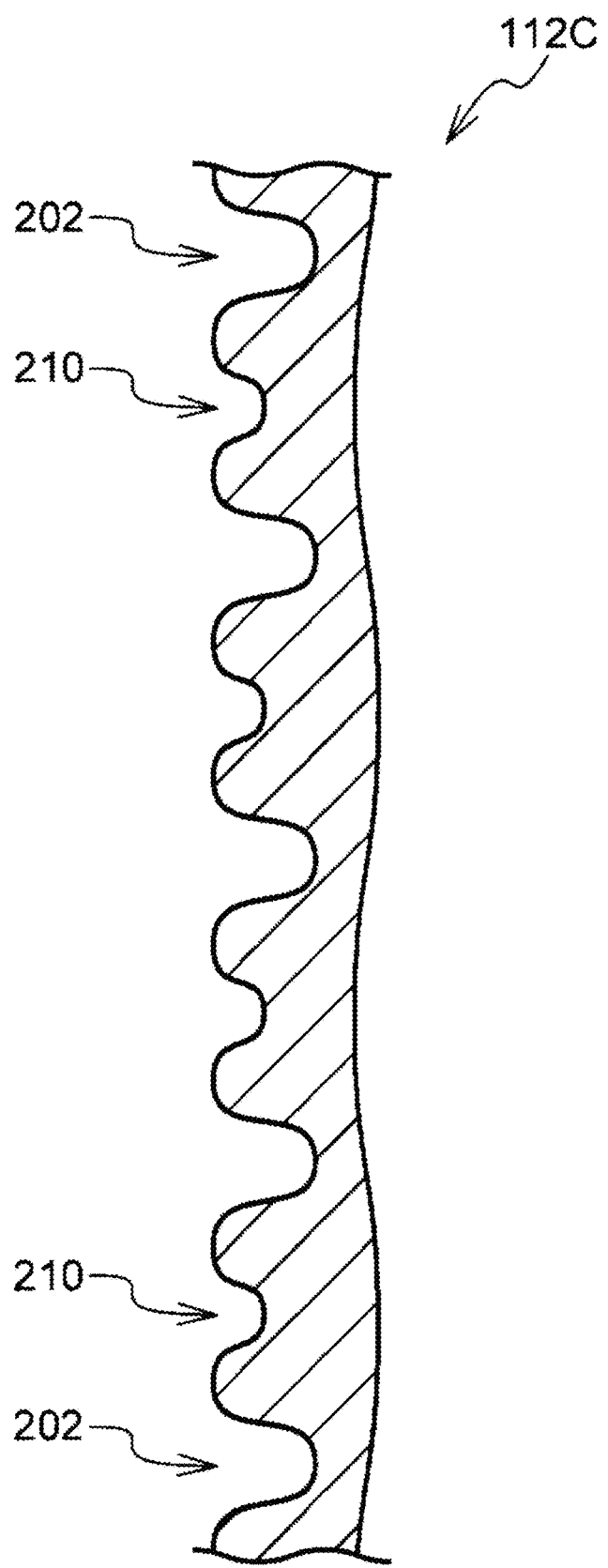
FIG. 12 is a cross-sectional view cut along the line A-A in FIG. 11.

FIG. 11 is a magnified view of the part surrounded by dash-dot lines in FIG. 10 (that is, a magnified view of the concave-convex knitted fabric), and FIG. 12 is a cross-sectional view cut along the line A-A in FIG. 11.

As illustrated in FIG. 11 and FIG. 12, the concave-convex knitted fabric region 112C has a concave-convex structure including a plurality of concavities 202 and a plurality of concavities 210. It is needless to say that the portion other than the plurality of concavities 202 and the plurality of concavities 210 in the concave-convex knitted fabric region 112C relatively constitutes convexities with respect to the bottoms of the plurality of concavities 202 and the plurality of concavities 210. In FIG. 11 and FIG. 12, only some of the concavities are assigned with the reference numeral 202 or 210.

The concavities 202 have a long shape as viewed in a planar view. The longitudinal direction of the long shape of the concavities 202 is approximately parallel to the circumferential direction of the joint supporter 200.

The long-shaped concavities 202 contribute to the ease of stretching (particularly, the ease of stretching in the axial direction) of the concave-convex knitted fabric region 112C.

The concavities 210 have a circular shape as viewed in a planar view. The depth of the concavities 210 is shallower than the depth of the concavities 202. The diameter of the concavities 210 is smaller than the width of the concavities 202. In the concave-convex knitted fabric region 112C, a balance between the ease of stretching of the concave-convex knitted fabric region 112C and the strength is achieved at a superior level, by having the concavities 202 as well as the concavities 210.

The concave-convex shape of the concave-convex knitted fabric region 114C is also similar to the concave-convex shape of the concave-convex knitted fabric region 112C.

The concave-convex shape of the concave-convex knitted fabric region according to the fourth embodiment is not limited in this specific example.

For example, the concave-convex knitted fabric region 112C has a plurality of two kinds of concavities (concavities 202 and concavities 210); however, the concave-convex knitted fabric region according to the fourth embodiment may have a plurality of only one kind of concavities.

The concave-convex knitted fabric region 112C and the concave-convex knitted fabric region 114C respectively have an elastic modulus in the axial direction of less than 0.1 N/mm$^2$.

The concave-convex knitted fabric region 112C and the concave-convex knitted fabric region 114C respectively have an elastic modulus in the circumferential direction of from 0.1 N/mm$^2$ to 0.5 N/mm$^2$.

Therefore, when the joint supporter 200 is used, slippage upon wearing can be suppressed, while stress on the skin is reduced.

Furthermore, in each of the concave-convex knitted fabric region 112C and the concave-convex knitted fabric region 114C, the relationship: elongation ratio in the axial direction>elongation ratio in the circumferential direction is satisfied.

In the wear pressure applying region (in this example, the front face side 110A of the central region) and the concave-convex knitted fabric region 112C, the elongation ratio in the axial direction satisfies the relationship: concave-convex knitted fabric region 112C>wear pressure applying region.

Furthermore, in the wear pressure applying region (in this example, the front face side 110A of the central region) and the concave-convex knitted fabric region 114C, the elongation ratio in the axial direction satisfies the relationship: concave-convex knitted fabric region 114C>wear pressure applying region.

Through these configurations, excellent movement conformity is realized in the joint supporter 200.

In the joint supporter 200, the one-end side rib cuff section 113 and the other-end side rib cuff section 115 have a function of preventing slippage upon wearing and rolling up of the joint supporter 200 during wearing.

In regard to the joint supporter 200, the one-end side rib cuff section 113, the one-end side region 112, the central region 110, the other-end side region 114, and the other-end side rib cuff section 115 are continuously produced by circular knitting, and the overall structure of these becomes a seamless structure. Thereby, especially excellent fitting comfort is obtained during wearing.

However, the garment of the fourth embodiment is not limited to this example, and the garment may be produced by using a circular-knitted fabric and a fabric other than a circular-knitted fabric in combination by sewing them together.

In the joint supporter 200, the average wear pressure XA of the central region 110 and the average wear pressure XB of the one-end side region 112 and the other-end side region 114 satisfy the relationship: wear pressure difference [average wear pressure XA−average wear pressure XB]>0 kPa.

In the joint supporter 200, the average wear pressure XA of the central region 110 and the average wear pressure XB1 of the one-end side region 112 satisfy the relationship: wear pressure difference [average wear pressure XA−average wear pressure XB1]>0 kPa.

In the joint supporter 200, the average wear pressure XA of the central region 110 and the average wear pressure XB2 of the other-end side region 114 satisfy the relationship: wear pressure difference [average wear pressure XA−average wear pressure XB2]>0 kPa.

The respective preferred ranges of the wear pressure difference [average wear pressure XA−average wear pressure XB], the wear pressure difference [average wear pressure XA−average wear pressure XB1], the wear pressure difference [average wear pressure XA−average wear pressure XB2], the average wear pressure XA, the average wear pressure XB, the average wear pressure XB1, and the average wear pressure XB2 are as described above.

In the joint supporter 200, an elongation ratio in the circumferential direction of the central region 110 is smaller than an elongation ratio in the circumferential direction of the one-end side region 112 and is smaller than an elongation ratio in the circumferential direction of the other-end side region 114.

In the joint supporter 200, an elongation ratio in the axial direction of the central region 110 is smaller than an elongation ratio in the axial direction of the one-end side region 112 and is smaller than an elongation ratio in the axial direction of the other-end side region 114.

In regard to the joint supporter 200, in the one-end side region 112 and the other-end side region 114, the relationship: elongation ratio in the axial direction>elongation ratio in the circumferential direction, and the condition of an elongation ratio in the axial direction of 150% or higher are both satisfied.

However, the fourth embodiment is not limited to this example, and it is desirable that in at least a portion of the region between the one-end side region or the other-end side region, at least one of the relationship: elongation ratio in the axial direction>elongation ratio in the circumferential direction, or the condition of an elongation ratio in the axial direction of 150% or higher is satisfied.

In regard to the materials, yarn, and knitted fabrics of the joint supporter 200, the materials, yarn, and knitted fabrics of the supporter body 100 (specific example of the first embodiment) described above can be referred to.

The size of the joint supporter 200 is set as appropriate according to the type of the joint on which the joint supporter 200 is worn.

For example, in a case in which the joint supporter 200 is used as a knee supporter that is worn on the knee joint, the preferred range of the size of the joint supporter 200 is similar to the preferred range of the size of the supporter body 100 described above.

The joint supporter 200 is such that in regard to each of a measurement area XX1 (measurement area XX1 is not shown in the diagram) centering on the center XX on the front face side 110A (wear pressure applying region) of the central region; a measurement area XT1 (measurement area XT1 is not shown in the diagram) centering on the position XT, which is the center in the axial direction in the one-end side region 112 on an extension line extending in the axial direction from the center XY on the back face side 110B of the central region; and a measurement area XS1 (measurement area XS1 is not shown in the diagram) centering on the center XS on the back face side 114B of the other-end side region on an extension line extending in the axial direction from the center XY on the back face side 110B of the central region, when an elongation ratio in the circumferential direction is measured by a tensile test under conditions of a grip width of 15 mm, a distance between grippers of 15 mm, and a tensile load of 20 N, an elongation ratio in the circumferential direction of the measurement area XX1 is lower than an elongation ratio in the circumferential direction of the measurement area XT1 and is lower than an elongation ratio in the circumferential direction of the measurement area XS1.

The joint supporter 200 is such that in regard to the measurement position XX1, the measurement position XT1, and the measurement position XS1, when an elongation ratio in the axial direction is measured by a tensile test under conditions described above, an elongation ratio in the axial direction of the measurement area XX1 is lower than an elongation ratio in the axial direction of the measurement area XT1 and is lower than an elongation ratio in the axial direction of the measurement area XS1.

In the joint supporter 200, when the central region 110 is stretched with a force of 5 kg in a direction in which a distance will increase between the center XX of the wear pressure applying region and a center XY at a back face side 110B of the central region, an elongation percentage of the central region is from 180% to 280%.

Furthermore, in the joint supporter 200, when an elongation ratio in the circumferential direction is measured at each of three points in total, the three points being the center XX of the wear pressure applying region, the center XY at the back face side 110B of the central region, and an intermediate position between the center XX and the center XY, the three measured values are all included in a range of from 100% to 250%, and a difference between a maximum value and a minimum value of the three measured values is from 0% to 80%.

Thus, the joint supporter 200 as a specific example of the garment of the fourth embodiment has been explained;

however, the garment of the fourth embodiment is not intended to be limited to this specific example.

Figure 13:
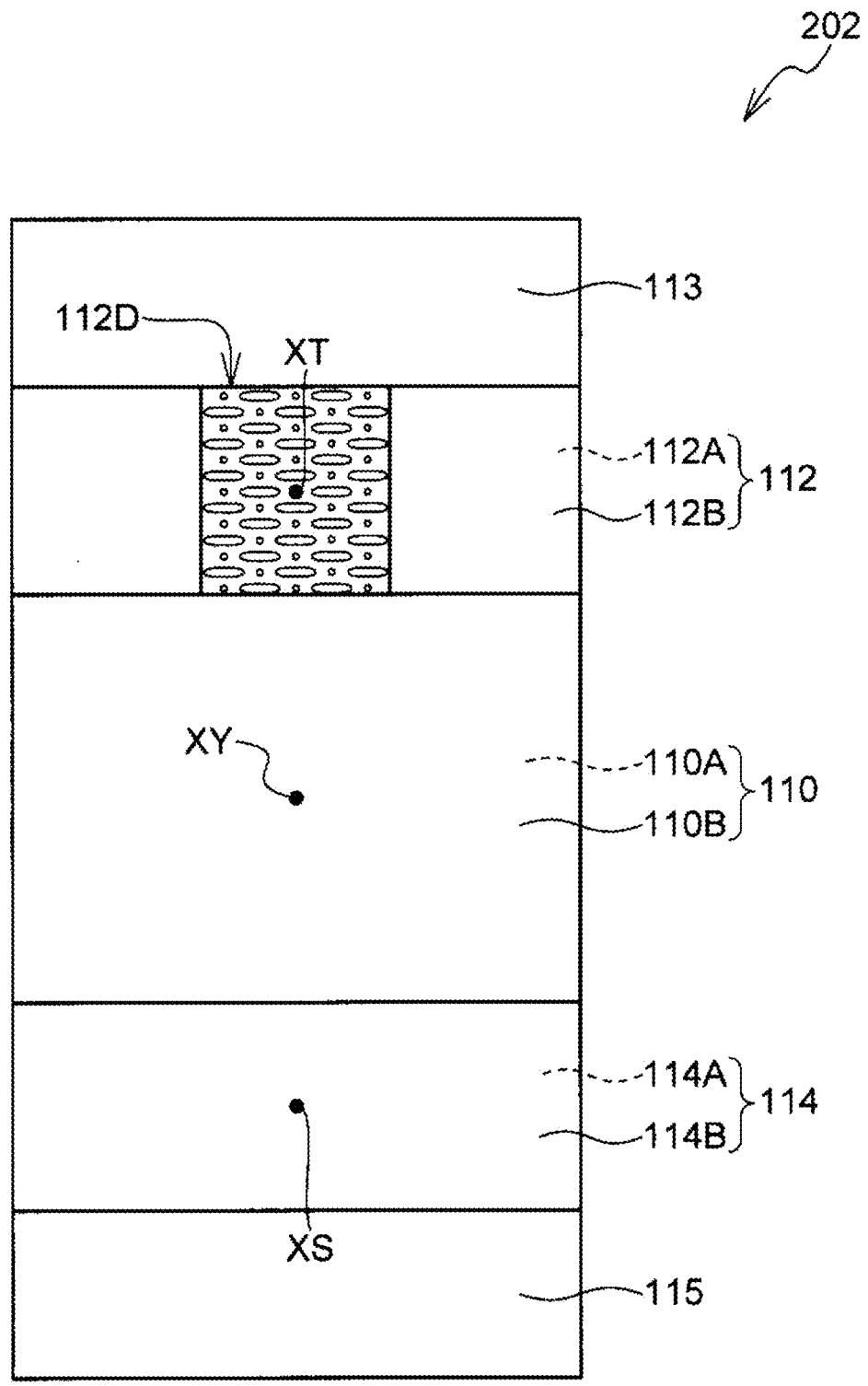
FIG. 13 is a rear view conceptually illustrating a supporter as another specific example of the garment of the fourth embodiment.

FIG. 13 is a rear view conceptually illustrating a joint supporter 202, which is another specific example of the garment of the fourth embodiment.

As illustrated in FIG. 13, in the joint supporter 202, the back face side 112B of the one-end side region includes a concave-convex knitted fabric region 112D, and the length in the circumferential direction of the concave-convex knitted fabric region 112D is a length equal to about ⅙ of the total circumferential length of the one-end side region 112 (that is, a length equal to about ⅓ of the length in the circumferential direction on the back face side 112B of the one-end side region).

Furthermore, in the joint supporter 202, a concave-convex knitted fabric region is not included in the back face side 114B of the one-end side region.

Except for these matters, the configuration of the joint supporter 202 is similar to the configuration of the joint supporter 200.

As illustrated in FIG. 13 (joint supporter 202), it is not necessarily essential that the concave-convex knitted fabric region is included in both of the back face side of the one-end side region and the back face side of the other-end side region, and the concave-convex knitted fabric region may be included in a portion of regions other than the wear pressure applying region. From the viewpoint of reducing stress on the skin, the present preferred embodiment is an embodiment in which the concave-convex knitted fabric region is included in at least one of the back face side of the one-end side region or the back face side of the other-end side region, and a more preferred embodiment is an embodiment in which the length in the circumferential direction of the concave-convex knitted fabric region is a length equal to ⅙ or more of the total circumferential length (for example, the joint supporter 200 and the joint supporter 202).

Figure 14:
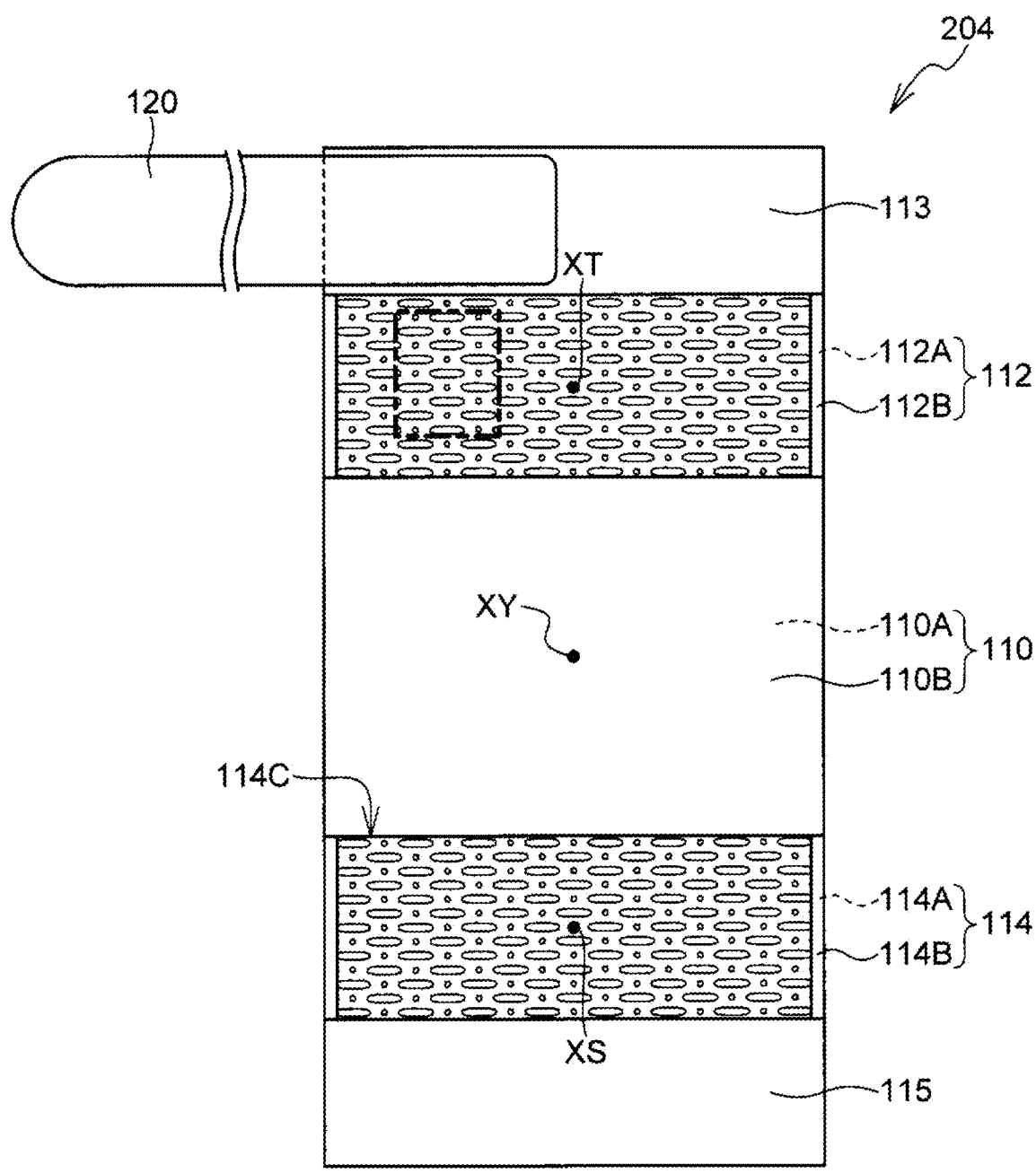
FIG. 14 is a rear view conceptually illustrating a supporter as still another specific example of the garment of the fourth embodiment.

FIG. 14 is a rear view conceptually illustrating a joint supporter 204, which is another specific example of the garment of the fourth embodiment.

As illustrated in FIG. 14, the joint supporter 204 includes a fastening belt 120 for fastening a one-end side rib cuff section 113 to a part of the body. A one-end section of this fastening belt 120 is connected to a portion of the surface on the rear face side of the one-end side rib cuff section 113 (surface on the opposite side from the surface facing the body). The fastening belt 120 includes a hook-and-loop fastener (not shown in the diagram), and thereby, at least the other-end section of the fastening belt 120 can be fastened in an attachable and detachable manner to a portion of the surface on the rear face side of the one-end side rib cuff section 113.

When the joint supporter 204 is used, for example, first, the joint supporter 204 is worn on a part of the body including a joint site, subsequently a fastening belt 120 is wrapped around from above the one-end side rib cuff section 113, and then at least another end side of the fastening belt 120 is fastened in an attachable and detachable manner to a portion of the surface on the rear face side of the one-end side rib cuff section 113. Thereby, slippage upon wearing of the joint supporter 204 can be more effectively suppressed.

In the joint supporter 204, one end of the fastening belt 120 is connected to a portion of the surface on the rear face side of the one-end side rib cuff section 113, and the one end of the fastening belt may also be fastened on the front face of the one-end side rib cuff section 113.

Furthermore, the fastening belt of the joint supporter 204 is an example including a hook-and-loop fastener; however, in addition to the hook-and-loop fastener, a buckle, a side release buckle, a wire adjuster, or the like can also be used.

Specific examples of the garment of the fourth embodiment also include garments incorporated with the joint supporter 200 as a supporter section (bottoms (for example, bottoms for sport applications or innerwear) such as spats, tights (for example, sport tights, compression tights, and medical tights), girdles, panty hoses, leggings, stirrup pants, and leg warmers; tops such as underwear, shirts, and compression shirts; socks; gloves; fingerstalls; and bandages).

Hereinafter, the present embodiments will be explained more specifically by way of Test Examples; however, the present embodiments are not intended to be limited to the following Test Examples.

Test Example 1

Test Example 1 is a specific example of the first embodiment and the second embodiment.

As Test Example 1, tests on the relationships between the wear pressure difference [average wear pressure A−average wear pressure B], the wear pressure difference [average wear pressure A−average wear pressure B1], the wear pressure difference [average wear pressure A−average wear pressure B2] and the elongation ratios of the various sections, and the feeling of support, fitting comfort and movement conformity were carried out using Sample 1, which was a knee supporter having a configuration similar to the supporter body 100 described above.

As a comparison, similar tests were also carried out for each of the comparative samples a to d, which were commercially available knee supporters.

The details will be described below.

(Test of Sample 1)

—Details of Sample 1—

As described above, in Sample 1, a thigh side rib cuff section 13, a thigh side support section 12, a knee support section 10, a shin side support section 14, and a shin side rib cuff section 15 were continuously produced by circular knitting. In this case, the knitted fabric of the knee support section 10 was produced using a low-stretchable mesh knitted fabric as a main constituent, and the knitted fabrics of the thigh side support section 12 and the shin side support section 14 were all produced using a medium-stretchable mesh knitted fabric as a main constituent. The knitted fabrics of the thigh side rib cuff section 13 and the shin side rib cuff section 15 were all produced using a non-run knitted fabric.

The materials for the knee support section 10, the thigh side support section 12, the shin side support section 14, the thigh side rib cuff section 13, and the shin side rib cuff section 15 in Sample 1 were all nylon and polyurethane.

The size of Sample 1 in a non-stretched state was as follows.

Knee support section 10: length in the axial direction 130 mm, average circumferential length 220 mm Thigh side support section 12: length in the axial direction 50 mm, average circumferential length 208 mm Shin side support section 14: length in the axial direction 45 mm, average circumferential length 195 mm Thigh side rib cuff section 13: length in the axial direction 30 mm, average circumferential length 280 mm Shin side rib cuff section 15: length in the axial direction 20 mm, average circumferential length 240 mm Measurement of Average Wear Pressure A, Average Wear Pressure B, Wear Pressure Difference [Average Wear Pressure A−Average Wear Pressure B], Wear Pressure Difference

[Average Wear Pressure A–Average Wear Pressure B1], and Wear Pressure Difference [Average Wear Pressure A–Average Wear Pressure B2]

For Sample 1, the average wear pressure A, the average wear pressure B, the average wear pressure B1, and the average wear pressure B2 were measured according to the "method of measuring average wear pressure A, average wear pressure B, average wear pressure B1, and average wear pressure B2" described above.

As a mannequin M1, a standard size mannequin of a main in the age of 20's (manufactured by Nanasai Co., Ltd., product name "MD-20$_A$") was used. The size of the mannequin MD-20$_A$ was as previously disclosed as the size of mannequin M1.

As a wear pressure measuring apparatus, a contact pressure measuring instrument "AMI3037-10" manufactured by AMI Techno Co., Ltd., which was equipped with a sensor for wear pressure measurement, was used.

Attachment of sensors to positions P1 to P10 of the mannequin M1 was respectively carried out according to a predetermined handling method ("Contact pressure measuring instrument for pressure of clothes, body pressure, and the like/contact pressure•blood flow measurement system by AMI Techno Co., Ltd.", [online], AMI Techno Co., Ltd., [searched on Mar. 20, 2015], Internet <http://www.amitec.co.jp/>).

Specifically, sensors were adhered to the positions P1 to P10 using a cover tape "SB-PTB" for exclusive use with the "AMI3037-10". Next, air was inserted using a syringe attached to the apparatus such that the sensor thickness would be 0.5 mm.

The sensors are referred to as "air packs" in connection with the "AMI3037-10".

Sample 1 was worn, by pulling up straight, on the leg of the mannequin M1 having the positions P1 to P10 attached thereto. At this time, position X corresponding to the center of the kneecap in the knee support section 10 of Sample 1 was overlapped with the position P3 of the mannequin M1, and all of the sensors at the positions P1 to P10 were hidden under Sample 1. This state of wearing was designated as the initial position.

Next, Sample 1 at the initial position was subjected to inversion strain such that the thigh side part of Sample 1 would twist clockwise as viewed from above with respect to the knee side part of Sample 1 (that is, as viewed from the lower side of the leg toward the shin side; hereinafter, the same). At this time, the amount of inversion strain to be applied was set at the maximum amount that could maintain a state in which Sample 1 covered all the sensors and could maintain a state in which Sample 1 would not move while Sample 1 was not touched by hands. The state of wear in which Sample 1 was subjected to inversion strain was maintained for 50 seconds to 60 seconds.

Next, Sample 1 was returned to the initial position and was maintained for 50 seconds to 60 seconds.

Next, Sample 1 at the initial position was subjected to eversion strain such that the thigh side part of Sample 1 would twist anticlockwise as viewed from above with respect to the knee side part of Sample 1. At this time, the amount of eversion strain to be applied was set at the maximum amount that could maintain a state in which Sample 1 covered all the sensors and could maintain a state in which Sample 1 would not move while Sample 1 was not touched by hands. The state of wear in which Sample 1 was subjected to inversion strain was maintained for 50 seconds to 60 seconds.

Next, Sample 1 was returned to the initial position and was maintained for 50 seconds to 60 seconds.

Next, Sample 1 was subjected to tensile strain by stretching Sample 1 in a vertical direction. The amount of tensile strain to be applied was set at the maximum amount that could maintain a state in which Sample 1 would not move while Sample 1 was not touched by hands. The state of wear in which Sample 1 was subjected to tensile strain was maintained for 50 seconds to 60 seconds.

Next, Sample 1 was returned to the initial position and was maintained for 50 seconds to 60 seconds.

Next, the wear pressures at the positions P1 to P10 were measured using "AMI3037-10".

The average value of the various measured values for the positions P1, P5, P7, and P9 was determined, and the average value thus obtained was designated as average wear pressure B.

The average value of the various measured values for the positions P1 and P7 was determined, and the average value thus obtained was designated as average wear pressure B1.

The average value of the various measured values for the positions P5 and P9 was determined, and the average value thus obtained was designated as average wear pressure B2.

The average value of the various measured values for the positions P2, P3, P4, P6, P8, and P10 was determined, and the average value thus obtained was designated as average wear pressure A.

The wear pressure difference [average wear pressure A–average wear pressure B] was determined by subtracting the average wear pressure B from the average wear pressure A.

The wear pressure difference [average wear pressure A–average wear pressure B1] was determined by subtracting the average wear pressure B1 from the average wear pressure A.

The wear pressure difference [average wear pressure A–average wear pressure B2] was determined by subtracting the average wear pressure B2 from the average wear pressure A.

The average wear pressure A, the wear pressure difference [average wear pressure A–average wear pressure B], the wear pressure difference [average wear pressure A–average wear pressure B1], and the wear pressure difference [average wear pressure A–average wear pressure B2] are presented in the following Table 1.

—Measurement of Elongation Ratio (%)—

In regard to Sample 1, for each of a measurement area X1 centering on position X, which corresponds to the center of the kneecap in the knee support section 10; a measurement area T1 centering on the position T, which is the center in the axial direction in the thigh side support section 12 on an extension line 30 extending in the axial direction from position Y corresponding to the center of the popliteal part; and a measurement area S1 centering on the position S, which is the center in the axial direction in the shin side support section on the extension line 30 extending in the axial direction from position Y corresponding to the center of the popliteal part, the elongation ratio (%) in the axial direction and the elongation ratio (%) in the circumferential direction were measured.

The details of the method of measuring the elongation ratio (%) are as described above.

The measurement results are presented in the following Table 1.

—Evaluation of Feeling of Support, Fitting Comfort, and Movement Conformity—

Five test subjects in total, including four male adults and one female adult, were subjected to a sensory evaluation on the feeling of support, fitting comfort, and movement conformity.

Specifically, each test subject was instructed to wear Sample 1 for about 2 days, and after wearing, each test subject was interviewed in connection with the feeling of support, fitting comfort, and conformity to the bending and stretching movement of the knee (movement conformity).

Based on the results of the interviews, scoring was performed according to the following scoring method.

The results are presented in the following Table 1.

(Test for Comparative Samples a to d)

For each of Comparative Samples a to d (details will be described below), which were commercially available knee supporters, a test was carried out in the same manner as the test for Sample 1.

Various measurements made for the Comparative Samples a to d were carried out at the same positions as the measurement positions for Sample 1. However, although it is needless to say, for those comparative samples having a knee hole at the position corresponding to the center of the kneecap, the wear pressure at the position P3 was not used for the calculation of the average wear pressure A.

The results are presented in Table 1.

TABLE 1

|  |  | Sample 1 | Comparative Sample a | Comparative Sample b | Comparative Sample c | Comparative Sample d |
|---|---|---|---|---|---|---|
| Average wear pressure A (kPa) | | 3.5 | 3.4 | 3.1 | 0.7 | 1.2 |
| Wear pressure difference [average wear pressure A − average wear pressure B] (kPa) | | 1.5 | 1.8 | 0.5 | 0.1 | −0.2 |
| Wear pressure difference [average wear pressure A − average wear pressure B1] (kPa) | | 1.5 | 1.6 | 0.9 | 0.4 | −0.7 |
| Wear pressure difference [average wear pressure A − average wear pressure B2] (kPa) | | 1.4 | 2.0 | 0.0 | −0.1 | 0.2 |
| Elongation ratio of thigh side support section (measurement area T1) (%) | Axial direction | 614 | 111 | 75 | 144 | 204 |
| | Circumferential direction | 330 | 218 | 240 | 192 | 143 |
| Elongation ratio of knee support section (measurement area X1) (%) | Axial direction | 66 | 39 | 75 | 144 | N.D. |
| | Circumferential direction | 152 | 60 | 240 | 192 | N.D. |
| Elongation ratio of shin side support section (measurement area S1) (%) | Axial direction | 614 | 111 | 75 | 144 | 204 |
| | Circumferential direction | 330 | 218 | 240 | 192 | 143 |
| Feeling of support total score | | 23 | 17 | 17 | 6 | 7 |
| Fitting comfort total score | | 22 | 13 | 18 | 13 | 11 |
| Movement conformity total score | | 22 | 9 | 14 | 19 | 10 |
| Total score | | 67 | 39 | 49 | 38 | 28 |

—Method of Scoring Feeling of Support—
5 points: A feeling of support was felt noticeably.
4 points: A feeling of support was felt relatively.
3 points: It cannot be said whether a feeling of support could be felt.
2 points: A feeling of support was not much felt.
1 point: A feeling of support was not at all felt.
—Fitting Comfort—
5 points: Fitting comfort was felt noticeably.
4 points: Fitting comfort was felt relatively.
3 points: It cannot be said whether fitting comfort could be felt.
2 points: Fitting comfort was not much felt.
1 point: Fitting comfort was not at all felt.
—Movement Conformity—
5 points: Favorable movement conformity was obtained.
4 points: Movement conformity was relatively felt.
3 points: It cannot be said whether there was movement conformity.
2 points: Movement conformity was not much felt.
1 point: Movement conformity was not at all felt.

Next, for each of the feeling of support, fitting comfort, and movement conformity, the total scores given by the five test subjects was calculated was designated as total score for feeling of support, total score for fitting comfort, and total score for movement conformity, respectively.

Furthermore, the sum of the total score for the feeling of support, the total score for fitting comfort, and the total score for movement conformity was designated as comprehensive points.

In Table 1, "N.D." means no data.

In Table 1, Comparative Samples a to d were as follows.

Comparative Sample a: "OA SEAMLESS PRO" (size M-L) manufactured by Alcare Co., Ltd.

Comparative Sample b: "FUTURO (registered trademark) Knee Supporter" (size M) manufactured by 3M Company Comparative Sample c: "TOMMIE COPPER-KNEE SUPPORTER" (size M) manufactured by Tommie Copper, Inc.

Comparative Sample d: "PRO-FIT (registered trademark) for Knee" (size M) manufactured by PIP Co., Ltd.

As shown in Table 1, in Sample 1 in which the wear pressure difference [average wear pressure A−average wear pressure B] was more than 0 kPa (that is, the relationship: average wear pressure A>average wear pressure B was satisfied), the thigh side support section and the shin side support section both satisfied the relationship: elongation ratio in the axial direction>elongation ratio in the circumferential direction, and the respective elongation ratios in the axial direction of the thigh side support section and the shin side support section were 150% or higher, the feeling of support, fitting comfort, and movement conformity were all excellent.

In contrast, in Comparative Sample d in which the wear pressure difference [average wear pressure A−average wear pressure B] was 0 kPa or less, the feeling of support and fitting comfort were inferior.

In Comparative Samples a to c in which the thigh side support section did not satisfy the relationship: elongation ratio in the axial direction>elongation ratio in the circumferential direction, and the elongation ratio in the axial direction of the thigh side support section was less than 150%, the movement conformity was inferior.

Test Example 2

Test Example 2 is a specific example of the first embodiment and the second embodiment.

In the present specification, the mannequin used for measuring the wear pressure was specifically selected to be the mannequin M1, which is a standard size mannequin for a man in the age of 20's.

In Test Example 2, in order to check the objectiveness of the measurement of wear pressure using the mannequin M1, three kinds of knee supporters (the following Samples 1 to 3) having different sizes were worn on the mannequin M1, and the wear pressure in each case was measured.

Measurement of the wear pressure was carried out in the same manner as in the measurement of wear pressure in Test Example 1.

Sample 1: Sample 1 used in Test Example 1. The assumed size was size M. Stretch size 205 mm.

Sample 2: sample produced in the same manner as in the case of Sample 1, except that the stretch size was changed to 185 mm. The assumed size was size XS.

Sample 3: sample produced in the same manner as in the case of Sample 1, except that the stretch size was changed to 225 mm. The assumed size was size XL.

Here, the stretch size refers to the length in the horizontal direction (that is, length in a direction that orthogonally intersects the axial direction) of the knee supporter (supporter body) measured as described below.

First, the front face side and the back face side of the tubular supporter body are overlapped, and thereby the shape of the supporter body is made into an approximately flat shape (see FIG. 7). The entirety of one end and the entirety of the other end in the horizontal direction of the supporter body that has been made into an approximately flat shape are respectively gripped, and a tensile force of 5 N is applied thereto in the horizontal direction to thereby stretch the supporter body in the horizontal direction (see FIG. 8). The length in the horizontal direction of the stretched supporter body is measured, and this length in the horizontal direction is designated as stretch size.

As a result of the measurement of wear pressure, the wear pressure difference [average wear pressure A−average wear pressure B] was 2.3 kPa for Sample 2 (assumed to be size XS), 1.5 kPa for Sample 1 (assumed to be size M), and 1.2 kPa for Sample 3 (assumed to be size XL).

As described above, it was confirmed that the difference in the wear pressure caused by the difference in size was not so significantly large. Specifically, in all of the three kinds of knee supporters (Samples 1 to 3 described below), the relationship: average wear pressure A>average wear pressure B (furthermore, the relationship: average wear pressure A−average wear pressure B≥0.8 kPa; and the relationship: average wear pressure A−average wear pressure B≥1.0 kPa) was satisfied.

Therefore, it was confirmed that the wear pressures of knee supporters of various sizes can be objectively measured using a mannequin M1 having a particular size.

Test Example 3

Test Example 3 is a specific example of the third embodiment.

For Sample 1 used in Test Example 1, the elongation percentage of the knee support section was measured by the measurement method described above. The measurement of the elongation percentage of the knee support section was carried out using a "new weight-type dimension measuring device (for socks)" manufactured by Ohtake Works, Ltd. The results are presented in Table 2.

Furthermore, at each of position X, position Y, and an intermediate position between position X and position Y in Sample 1, the elongation ratio in the circumferential direction was measured by the measurement method described above. The results are presented in Table 2.

—Evaluation of Ease of Bending and Stretching of Knee Joint—

Five test subjects in total, including four male adults and one female adult, were subjected to a sensory evaluation on the ease of bending and stretching of the knee joint.

Specifically, each test subject was instructed to wear Support 1 for about 2 days, and after wearing, each test subject was interviewed in connection with the ease of bending and stretching of the knee joint.

Based on the results of the interviews, scoring was performed according to the following scoring method.

The results are presented in Table 2. In Table 2, "N.D." means no data.

In Table 2, the wear pressure difference, feeling of support, and fitting comfort obtained in Test Example 1 are presented again.

—Method of Scoring of Ease of Bending and Stretching of Knee Joint—

5 points: The ease of bending and stretching of the knee joint was felt noticeably.

4 points: The ease of bending and stretching of the knee joint was relatively felt.

3 points: It cannot be said whether the ease of bending and stretching of the knee joint could be felt.

2 points: The ease of bending and stretching of the knee joint was hardly felt.

1 point: The ease of bending and stretching of the knee joint was not at all felt.

TABLE 2

|  | | Sample 1 | Comparative Sample a | Comparative Sample b | Comparative Sample c | Comparative Sample d |
|---|---|---|---|---|---|---|
| Wear pressure difference [average wear pressure A − average wear pressure B] (kPa) | | 1.5 | 1.8 | 0.5 | 0.1 | −0.2 |
| Elongation percentage of knee support section (%) | | 211 | 167 | 150 | 123 | 194 |
| Elongation ratio in | Position X | 162 | N.D. | N.D. | N.D. | N.D. |
| | Position Y | 144 | N.D. | N.D. | N.D. | N.D. |

TABLE 2-continued

| | | Sample 1 | Comparative Sample a | Comparative Sample b | Comparative Sample c | Comparative Sample d |
|---|---|---|---|---|---|---|
| circumferential direction (%) | Intermediate position between position X and position Y | 199 | N.D. | N.D. | N.D. | N.D. |
| Feeling of support total score | | 23 | 17 | 17 | 6 | 7 |
| Fitting comfort total score | | 22 | 13 | 18 | 13 | 11 |
| Ease of bending and stretching of knee joint total score | | 24 | 7 | 12 | 22 | 16 |
| Total score | | 69 | 37 | 47 | 41 | 34 |

As disclosed in Table 2, Sample 1 in which the wear pressure difference [average wear pressure A−average wear pressure B] was more than 0 kPa (that is, the relationship: average wear pressure A>average wear pressure B was satisfied), and the elongation percentage of the knee support section was from 180% to 280%, exhibited excellent ease of bending and stretching of the knee joint compared to Comparative Samples a to c, in which the elongation percentage of the knee support section was less than 180%.

Comparative Sample d had an elongation percentage of the knee support section of from 180% to 280%; however, since the wear pressure difference [average wear pressure A−average wear pressure B] was 0 kPa or less, the feeling of support and fitting comfort were inferior.

Test Example 4

Test Example 4 is a specific example of the fourth embodiment.

In Test Example 4, Sample 4 was produced, which is a joint supporter having a configuration similar to that of the joint supporter 200 described above.

In regard to Sample 4, a one-end side rib cuff section 113, a one-end side region 112, a central region 110, an other-end side region 114, and an other-end side rib cuff section 115 were continuously produced by circular knitting.

In this case, the knitted fabric of the central region 110 was produced using a low-stretchable mesh knitted fabric including float knitting and tuck knitting as a main constituent, and the knitted fabrics of the one-end side region 112 and the other-end side region 114 were all produced using a medium-stretchable mesh knitted fabric as a main constituent.

The one-end side region 112 was produced such that almost the entire surface of the back face side 112B of the one-end side region became a concave-convex knitted fabric region 112C, and the front face side 112A of the one-end side region had a higher elastic modulus in the axial direction than that of the concave-convex knitted fabric region 112C. Similarly, the other-end side region 114 was produced such that almost the entire surface of the back face side 114B of the other-end side region became a concave-convex knitted fabric region 114C, and the front face side 114A of the other-end side region had a higher elastic modulus in the axial direction than that of the concave-convex knitted fabric region 114C. Here, almost a semicircular portion that was positioned on the outer side when the joint was bent was designated as the front face side, and the remaining almost semicircular portion was designated as the back face side. In Sample 4, the areas of the concave-convex knitted fabric region 112C and the concave-convex knitted fabric region 114C were produced to be almost equal.

The knitted fabrics of the one-end side rib cuff section 113 and the other-end side rib cuff section 115 were all producing using a non-run knitted fabric. The concavities in the concave-convex knitted fabric region 112C and the concave-convex knitted fabric region 114C were all produced using a knitted fabric formed by skipping one or more stitches in the circumferential direction by float knitting, and knitting in combination with tuck knitting. The front face side 110A of the central region (that is, wear pressure applying region) and the back face side 110B of the central region were dividedly knitted by changing the combination of float knitting and tuck knitting.

The elongation ratio in the axial direction of the front face side 110A of the central region (that is, wear pressure applying region) was 184%, and the elongation ratio in the axial direction of the back face side 110B of the central region was 111%.

The non-stretch size of Sample 4 was set to be similar to the non-stretch size of Sample 1 of Test Example 1.

The one-end side rib cuff section 113, the one-end side region 112, the central region 110, the other-end side region 114, and the other-end side rib cuff section 115 in Sample 4 correspond to the thigh side rib cuff section 13, the thigh side support section 12, the knee support section 10, the shin side support section 14, and the shin side rib cuff section 15 in Sample 1, respectively.

(Measurement of Wear Pressure)

Wear pressures of Sample 4 were measured in the same manner as in Test Example 1, except that the mannequin M1 was changed to the following log, and the positions of measurement were changed as follows.

Specifically, sensors were attached to the respective sensor attachment positions (positions XP1 to XP5) of the log as described below. Sample 4 was worn on the log having the sensors attached thereto. In this case, the sensors at the positions XP1 to XP5 of the log were respectively made to overlap with the following positions of Sample 4 (see "Correlation between sensor attachment positions on log and positions in Sample 4").

—Log—

Shape and size: Cylindrical shape having a circumferential length of 374 mm

Material: Japanese cedar

Processing: Shaving, polishing, varnish processing, and polishing were performed in sequence.

—Sensor Attachment Positions (Five Sites) on Log—

Position XP1 on the log: Reference position

Position XP2 on the log: Position 100 mm upper to the position XP1

Position XP3 on the log: Just behind the position XP2

Position XP4 on the log: Position 100 mm lower to the position XP1

Position XP5 on the log: Just behind the position XP4

—Correlation between Sensor Attachment Positions on Log and Positions in Sample 4—

Position XP1 on the log: Center XX in the wear pressure applying region (front face side 110A of the central region) in Sample 4

Position XP2 on the log: Center of the front face side 112A of the one-end side region in Sample 4

Position XP3 on the log: Center XT of the back face side 112B of the one-end side region (concave-convex knitted fabric region 112C) in Sample 4

Position XP4 on the log: Center of the front face side 114A of the other-end side region in Sample 4

Position XP5 on the log: Center XS of the back face side 114B of the other-end side region in Sample 4 (concave-convex knitted fabric region 114C)

The measured value of wear pressure at position XP1 was designated as the wear pressure (kPa) of the wear pressure applying region.

The average value of the measured value of wear pressure at position XP2 and the measured value of wear pressure at position XP4 was designated as the average wear pressure (kPa) on the front side of the one-end side region and the front face side of the other-end side region.

The average value of the measured value of wear pressure at position XP3 and the measured value of wear pressure at position XP5 was designated as the average wear pressure (kPa) on the back face side of the one-end side region and the back face side of the other-end side region.

Next, the elongation ratio in the circumferential direction (%) of the wear pressure applying region during wearing was measured by the following formula.

Elongation ratio in circumferential direction of wear pressure applying region during wearing (%)= (length in circumferential direction of wear pressure applying region when worn on log/ length in circumferential direction of wear pressure applying region before being worn on log)×100

In Table 3, the elongation ratio (%) in the circumferential direction of the wear pressure applying region during wearing, the wear pressure (kPa) of the wear pressure applying region, the average wear pressure (kPa) of the one-end side region and the other-end side region, the average wear pressure (kPa) on the front face side of the one-end side region and the front face side of the other-end side region, and the average value (kPa) of the back face side of the one-end side region and the back face side of the other-end side region are respectively disclosed.

As shown in Table 3, it was confirmed that in Sample 4, the wear pressure of the wear pressure applying region is higher than the average wear pressure of the one-end side region and the other-end side region. Therefore, when Sample 4 is worn on a joint, an excellent feeling of support and excellent fitting comfort are obtained.

Furthermore, since Sample 4 includes a concave-convex knitted fabric region, an excellent effect of reducing stress on the skin is obtained.

Unlike Sample 4 in which two kinds of knitted fabrics are interlaced at approximately semicircular portions in the circumferential direction, in the case of a knitted fabric in which two kinds of knitted fabrics are not interlaced at approximately semicircular portions in the circumferential direction, the method of measuring the average wear pressure can be determined by the area average.

Specifically, the wear pressure at the area center of each knitted fabric is measured (P11, P12, and P13). The area of each knitted fabric is measured based on the method of measuring the resting size as described above (A1, A2, and A3). The average wear pressure (kPa) can be determined by the following formula using these values.

Average wear pressure=$(P11*A1+P12*A2+P13*A3)/(A1+A2+A3)$

In a case in which a fabric smaller in the axial direction and the circumferential direction than a sensor for measuring the wear pressure is included, an accurate value of the wear pressure can be measured by producing a tubular fabric sample larger than the sensor and performing the measurement of wear pressure.

(Measurement of Elastic Modulus in Axial Direction of Concave-Convex Knitted Fabric Region)

The elastic moduli in the axial direction obtained when the concave-convex knitted fabric region of Sample 4 was stretched at the elongation ratio in the axial direction indicated in the following Table 4, were respectively measured.

As the elastic modulus in the axial direction of the concave-convex knitted fabric region, the average value of the elastic modulus in the axial direction of the concave-convex knitted fabric region 112C (one end side) and the elastic modulus in the axial direction of the concave-convex knitted fabric region 114C (another end side) was employed.

TABLE 3

| Elongation ratio in circumferential direction of wear pressure applying region during wearing (%) | Wear pressure of wear pressure applying region (kPa) | Average wear pressure of one-end side region and other-end side region (kPa) | Average wear pressure of front face side of one-end side region and front face side of other-end side region (kPa) | Average wear pressure of back face side of one-end side region (concave-convex knitted fabric region) and back face side of other-end side region (concave-convex knitted fabric region) (kPa) |
|---|---|---|---|---|
| 82 | 3.8 | 2.8 | 3.4 | 2.2 |

The results are presented in Table 4.

TABLE 4

| Elongation ratio in axial direction (%) | Elastic modulus in axial direction of concave-convex knitted fabric region (N/mm$^2$) |
| --- | --- |
| 80 | 0.03 |
| 100 | 0.02 |
| 150 | 0.03 |
| 200 | 0.04 |

As shown in Table 4, the elastic modulus in the axial direction of the concave-convex knitted fabric region was less than 0.1 N/mm$^2$ over the range of the elongation ratio in the axial direction of from 80% to 200%.

Thereby, it was suggested that even if the concave-convex knitted fabric region is stretched up to 200% upon wearing, an allowance for elongation (that is, concavities and convexities) still remains, and the effect of reducing stress on the skin is suitably retained thereby. It is considered that similar effects are obtained until this elongation ratio in the axial direction reaches the critical elongation ratio.

In regard to the measurement of the elastic modulus in the axial direction of the concave-convex knitted fabric region described above, in a case in which a concave-convex knitted fabric region including a single concave-convex knitted fabric is used in the supporter section, the elastic modulus in the axial direction in this concave-convex knitted fabric region is designated as the elastic modulus in the axial direction of the concave-convex knitted fabric region.

Furthermore, in a case in which two or more kinds of concave-convex knitted fabric regions including concave-convex knitted fabrics of different knitting are used in the supporter section, the elastic moduli in the axial direction for the various regions are determined, and the area average value thereof is designated as the elastic modulus in the axial direction of the concave-convex knitted fabric region.

When the average value of the elastic moduli in the axial direction of the one end side and the concave-convex knitted fabric region and the elastic modulus in the axial direction of the concave-convex knitted fabric region at another end side is calculated, in a case in which the areas of the various regions are different, the average value is calculated in consideration of those areas.

(Measurement of Elastic Modulus in Circumferential Direction of Concave-Convex Knitted Fabric Region)

The elastic modulus in the circumferential direction obtainable when the concave-convex knitted fabric region of Sample 4 was stretched at an elongation ratio in the circumferential direction of 200%, was measured.

Regarding the elastic modulus in the circumferential direction of the concave-convex knitted fabric region, the average value of the elastic modulus in the circumferential direction of the concave-convex knitted fabric region 112C (one end side) and the elastic modulus in the circumferential direction of the concave-convex knitted fabric region 114C (another end side) was employed.

As a result, it was confirmed that the elastic modulus in the circumferential direction obtainable when the sample was stretched at an elongation ratio in the circumferential direction of 200% was 0.35 N/mm$^2$, and this value was in the range of from 0.1 N/mm$^2$ to 0.5 N/mm$^2$. It was also confirmed that knitted fabrics having an elastic modulus in the circumferential direction that is included in the range described above, all tend to have excellent fitting comfort.

Thereby, it was suggested that Sample 4 has excellent effects of enhancement of fitting comfort, suppression of slippage upon wearing, and reduction of stress on the skin.

In regard to the measurement of the elastic modulus in the circumferential direction of the concave-convex knitted fabric region described above, in a case in which a concave-convex knitted fabric region including a single concave-convex knitted fabric is used in the supporter section, the elastic modulus in the circumferential direction in this concave-convex knitted fabric region is designated as the elastic modulus in the circumferential direction of the concave-convex knitted fabric region.

In a case in which two or more kinds of concave-convex knitted fabric regions including concave-convex knitted fabrics of different knitting are used in the supporter section, the elastic moduli in the circumferential direction in the various regions are determined, and the area average value thereof is designated as the elastic modulus in the circumferential direction of the concave-convex knitted fabric region.

Furthermore, when the average value of the elastic moduli in the circumferential direction of the one end side and the concave-convex knitted fabric region and the elastic modulus in the circumferential direction of the concave-convex knitted fabric region at another end side is calculated, in a case in which the areas of the various regions are different, the average value is calculated in consideration of those areas.

(Sensory Test on Slippage Upon Wearing (Wearing Test))

Six test subjects in total, including four male adults and two female adults, were subjected to a sensory test on the disposition of the concave-convex knitted fabric region.

First, the test subjects were instructed to wear Sample 4 backwards for about 2 days. Here, the term backwards refers to a direction in which the concave-convex knitted fabric region 112C (one end side) faces the front side of the thigh, and the concave-convex knitted fabric region 114C (another end side) faces the front side of the shin.

Next, the test subjects were instructed to wear Sample 4 forwards for about 2 days. Here, the term forwards refers to a direction in which the concave-convex knitted fabric region 112C (one end side) faces the back side of the thigh, and the concave-convex knitted fabric region 114C (another end side) faces the back side of the shin (that is, calf side).

Subsequently, the test subjects were interviewed in connection with slippage upon wearing of Sample 4 in the case of being worn backwards and in the case of being worn forwards.

In both cases in which the test subjects were instructed to wear Sample 4 forwards or backwards, the wear pressure of the wear pressure applying region in Sample 4 was higher than the average wear pressures of the one-end side region and the other-end side region.

Based on the results of the interviews, scoring was performed according to the following scoring method.

—Method of Scoring Slippage upon Wearing—

5 points: In the case of wearing forwards, the slippage upon wearing was ameliorated, compared to the case of wearing backwards.

4 points: In the case of wearing forwards, the slippage upon wearing was ameliorated somehow, compared to the case of wearing backwards.

3 points: In the case of wearing forwards, it cannot be said whether the slippage upon wearing was ameliorated, compared to the case of wearing backwards.

2 points: In the case of wearing forwards, the slippage upon wearing was aggravated somehow, compared to the case of wearing backwards.

1 point: In the case of wearing forwards, the slippage upon wearing was aggravated, compared to the case of wearing backwards.

The test results obtained from the six test subjects were such that two people gave 5 points, two people gave 4 points, one person gave 3 points, one person gave 2 points, and none gave 1 point.

Thereby, it was found that in a case in which the sample is worn forwards (that is, in a case in which the concave-convex knitted fabric region faces the back side of the thigh and the shin), slippage upon wearing tends to be ameliorated, compared to a case in which the sample is worn backwards (that is, in a case in which the concave-convex knitted fabric region faces the front side of the thigh and the shin).

The entire disclosures of Japanese Patent Application No. 2015-087593 and Japanese Patent Application No. 2016-020145 are incorporated herein by reference.

All publications, patent applications, and technical standards mentioned in this specification are herein incorporated by reference to the same extent as if each individual publication, patent application, or technical standard was specifically and individually indicated to be incorporated by reference.

The invention claimed is:

1. A knee supporter comprising a tubular supporter body, the tubular support body including:
   a knee support section that is worn on a part of a leg including a knee and that supports the knee;
   a thigh side support section that supports a thigh side with respect to the knee of the leg; and
   a shin side support section that supports a shin side with respect to the knee of the leg, wherein:
   an average wear pressure A of the knee support section and an average wear pressure B of the thigh side support section and the shin side support section satisfy the relationship: average wear pressure A>average wear pressure B; and
   an elongation ratio in an axial direction measured by a tensile test under conditions of a grip width of 15 mm, a distance between grippers of 15 mm, and a tensile load of 20 N, in at least a partial region R in the thigh side support section and the shin side support section, is 150% or higher.

2. The knee supporter according to claim 1, wherein when the knee support section is stretched with a force of 5 kg in a direction in which a distance will increase between a position X, which corresponds to a center of a kneecap in the knee support section, and a position Y, which corresponds to a center of a popliteal part in the knee support section, an elongation percentage of the knee support section is from 180% to 280%.

3. The knee supporter according to claim 1, wherein the average wear pressure A is 2.6 kPa or greater.

4. The knee supporter according to claim 1, wherein:
   the average wear pressure A and an average wear pressure B1 of the thigh side support section satisfy the relationship: average wear pressure A>average wear pressure B1, and
   the average wear pressure A and an average wear pressure B2 of the shin side support section satisfy the relationship: average wear pressure A>average wear pressure B2.

5. The knee supporter according to claim 1, wherein at least the thigh side support section, the knee support section, and the shin side support section are continuously produced by circular knitting.

6. A knee supporter comprising a tubular supporter body, the tubular support body including:
   a knee support section that is worn on a part of a leg including a knee and that supports the knee;
   a thigh side support section that supports a thigh side with respect to the knee of the leg; and
   a shin side support section that supports a shin side with respect to the knee of the leg, wherein:
   an average wear pressure A of the knee support section and an average wear pressure B of the thigh side support section and the shin side support section satisfy the relationship: average wear pressure A>average wear pressure B; and
   an elongation ratio in an axial direction and an elongation ratio in a circumferential direction measured by a tensile test under conditions of a grip width of 15 mm, a distance between grippers of 15 mm, and a tensile load of 20 N, in at least a partial region R in the thigh side support section and the shin side support section, satisfy the relationship: elongation ratio in axial direction>elongation ratio in circumferential direction.

* * * * *